(12) United States Patent
Phillips

(10) Patent No.: US 6,699,885 B2
(45) Date of Patent: *Mar. 2, 2004

(54) SUBSTITUTED BENZIMIDAZOLE DOSAGE FORMS AND METHODS OF USING SAME

(75) Inventor: Jeffrey O. Phillips, Ashland, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/054,350

(22) Filed: Jan. 19, 2002

(65) Prior Publication Data

US 2003/0191159 A1 Oct. 9, 2003

Related U.S. Application Data

(63) Continuation-in-part of application No. 09/901,942, filed on Jul. 9, 2001, which is a continuation-in-part of application No. 09/481,207, filed on Jan. 11, 2000, now Pat. No. 6,489,346, which is a continuation-in-part of application No. 09/183,422, filed on Oct. 30, 1998, now abandoned, which is a continuation-in-part of application No. 08/680,376, filed on Jul. 15, 1996, now Pat. No. 5,840,737.
(60) Provisional application No. 60/009,608, filed on Jan. 4, 1996.

(51) Int. Cl.[7] .......................................... A61K 31/4439
(52) U.S. Cl. .................... 514/338; 514/395; 424/717
(58) Field of Search ................ 514/338, 395

(56) References Cited

U.S. PATENT DOCUMENTS

| | | |
|---|---|---|
| 4,045,564 A | 8/1977 | Berntsson et al. |
| 4,182,766 A | 1/1980 | Krasso et al. |
| 4,255,431 A | 3/1981 | Junggren et al. |
| 4,337,257 A | 6/1982 | Junggren et al. |
| 4,359,465 A | 11/1982 | Ruwart |
| 4,414,216 A | 11/1983 | Kawakita et al. |
| 4,472,409 A | 9/1984 | Senn-Bilfinger |
| 4,508,905 A | 4/1985 | Junggren et al. |
| 4,544,750 A | 10/1985 | Brandstrom et al. |
| 4,620,008 A | 10/1986 | Brandstrom et al. |
| 4,636,499 A | 1/1987 | Brandstrom et al. |
| 4,738,974 A | 4/1988 | Brandstrom et al. |
| 4,786,505 A | 11/1988 | Lovgren et al. |
| 4,853,230 A | 8/1989 | Lovgren et al. |
| 4,965,351 A | 10/1990 | Caruso et al. |
| 5,008,278 A | 4/1991 | Brandstrom et al. |
| 5,013,743 A | 5/1991 | Iwahi et al. |
| 5,019,584 A | 5/1991 | Brandstrom et al. |
| 5,025,024 A | 6/1991 | Brandstrom et al. |
| 5,039,806 A | 8/1991 | Brandstram et al. |
| 5,045,321 A | 9/1991 | Makino et al. |
| 5,075,323 A | 12/1991 | Fain et al. |
| 5,093,132 A | 3/1992 | Makino et al. |
| 5,093,342 A | 3/1992 | Tomoi et al. |
| 5,106,862 A | 4/1992 | Briving et al. |
| 5,124,158 A | 6/1992 | Ruwart et al. |
| 5,215,974 A | 6/1993 | Alminger et al. |
| 5,219,870 A | 6/1993 | Kim |
| 5,232,706 A | 8/1993 | Coll |
| 5,244,670 A | 9/1993 | Upson et al. |

(List continued on next page.)

FOREIGN PATENT DOCUMENTS

| | | |
|---|---|---|
| CA | 1234118 | 3/1988 |
| DK | 19752843 | 7/1999 |
| EP | 0005129 A1 B1 | 10/1979 |
| EP | 0244380 A2 B1 | 11/1987 |
| EP | 0247983 A2 B1 | 12/1987 |
| EP | 0308515 A1 B1 | 3/1989 |
| EP | 0315964 A1 B1 | 5/1989 |
| EP | 0394471 A1 | 10/1990 |
| EP | 0414847 B1 | 3/1991 |
| EP | 0436620 B1 | 7/1991 |
| EP | 0452697 A1 B1 | 10/1991 |
| EP | 0465254 A1 | 1/1992 |
| EP | 0237200 B1 | 7/1992 |
| EP | 0496437 A2 B1 A3 | 7/1992 |
| EP | 0502556 A1 B1 | 9/1992 |
| EP | 0338861 B1 | 1/1993 |
| EP | 0248634 A2 B1 | 7/1993 |
| EP | 0565210 A2 A3 B1 | 10/1993 |
| EP | 0567201 A2 A3 B1 | 10/1993 |
| EP | 0567643 A1 | 11/1993 |
| EP | WO94/02140 * | 2/1994 |
| EP | 0587659 B1 | 3/1994 |
| EP | 0652751 B1 | 5/1995 |
| EP | 0654471 A1 B1 | 5/1995 |
| EP | 0696921 B1 | 2/1996 |

(List continued on next page.)

OTHER PUBLICATIONS

Tabata, T., et al., Stabilization of a New Antiulcer Drug (Lansoprazole) in the Solid Dosage Forms, *Drug Development and Industrial Pharmacy*, 18(13), 1437–1447, (1992).

Kromer, et al., Differences in pH–Dependent Activation Rate of Substituted Benzimidazoles and Biological in vitro Correlates, *Pharmacology*, Vol. 56, pp. 57–70, (1998).

"Agents for Control of Gastric Acidity and Treatment of Peptic Ulcers", Chapter 37, pp. 907–909, 1768.

"Buffered and Isotonic Solutions", *Physical Pharmacy*, Chapter 8, pp. 169–189.

"Gastrointestinal Drugs", *The American Medical Association Drug Evaluation*, Vol. 2, The American Medical Association, Chicago, 1:8 (Bennett & Dickson, eds.).

Adams, S. P., et al., "Comments on the Report of 'association' of Omeprazole with DNA by Phillips, et al.", *Mutagenesis*, Vol. 7, No. 5, p. 395–396 (Sep. 1992).

(List continued on next page.)

*Primary Examiner*—Jane Fan
(74) *Attorney, Agent, or Firm*—Joseph A. Mahoney; Mayer, Brown, Rowe & Maw LLP

(57) ABSTRACT

Disclosed herein are methods, kits, combinations, and compositions for treating gastric acid disorders employing pharmaceutical compositions comprising a proton pump inhibiting agent (PPI) and a buffering agent in a pharmaceutically acceptable carrier.

51 Claims, 7 Drawing Sheets

U.S. PATENT DOCUMENTS

| | | | |
|---|---|---|---|
| 5,288,506 A | 2/1994 | Spickett et al. |
| 5,339,700 A | 8/1994 | Wright et al. |
| 5,374,730 A | 12/1994 | Slemon et al. |
| 5,385,739 A | 1/1995 | Debregeas et al. |
| 5,386,032 A | 1/1995 | Brandstrom |
| 5,391,752 A | 2/1995 | Hoerrner et al. |
| 5,395,323 A | 3/1995 | Berglund |
| 5,399,700 A | 3/1995 | Min et al. |
| 5,417,980 A | 5/1995 | Goldman et al. |
| 5,430,042 A | 7/1995 | Lindberg et al. |
| 5,447,918 A | 9/1995 | McCullough |
| 5,447,923 A | 9/1995 | Castrenich et al. |
| 5,470,983 A | 11/1995 | Slemon et al. |
| 5,504,082 A | 4/1996 | Kawakita et al. |
| 5,589,491 A | 12/1996 | Nakanishi et al. |
| 5,599,794 A | 2/1997 | Eek et al. |
| 5,629,305 A | 5/1997 | Eek et al. |
| 5,633,244 A | 5/1997 | Eek et al. |
| 5,639,478 A | 6/1997 | Makino et al. |
| 5,690,960 A | 11/1997 | Bengtsson et al. |
| 5,693,818 A | 12/1997 | Von Unge |
| 5,714,504 A | 2/1998 | Lindberg et al. |
| 5,714,505 A | 2/1998 | Hasselkus |
| 5,731,002 A | 3/1998 | Olovson et al. |
| 5,753,265 A | 5/1998 | Bergstrand et al. |
| 5,766,622 A | 6/1998 | Nelson |
| 5,776,765 A | 7/1998 | Graham et al. |
| 5,798,120 A | 8/1998 | Tomohisa et al. |
| 5,814,338 A | 9/1998 | Veronesi |
| 5,817,338 A | 10/1998 | Bergstrand et al. |
| 5,840,737 A | 11/1998 | Phillips |
| 5,876,759 A | 3/1999 | Gowan, Jr. |
| 5,877,192 A | 3/1999 | Lindberg et al. |
| 5,879,708 A | 3/1999 | Makino et al. |
| 5,883,102 A | 3/1999 | Hamley et al. |
| 5,885,594 A | 3/1999 | Nilsen et al. |
| 5,900,424 A | 5/1999 | Kallstrom et al. |
| 5,929,244 A | 7/1999 | Von Unge |
| 5,939,091 A | 8/1999 | Eoga et al. |
| 5,948,789 A | 9/1999 | Larsson et al. |
| 5,955,107 A | 9/1999 | Augello et al. |
| 5,958,955 A | 9/1999 | Gustavsson et al. |
| 5,962,022 A | 10/1999 | Bolt et al. |
| 5,965,162 A | 10/1999 | Fuisz et al. |
| 5,972,389 A | 10/1999 | Shell et al. |
| 5,979,515 A | 11/1999 | Olsson |
| 6,013,281 A | 1/2000 | Lundberg et al. |
| 6,017,560 A | 1/2000 | Makino et al. |
| 6,090,827 A | 7/2000 | Erickson et al. |
| 6,123,962 A | 9/2000 | Makino et al. |
| 6,124,464 A | 9/2000 | Hogberg et al. |
| 6,132,770 A | 10/2000 | Lundberg |
| 6,132,771 A | 10/2000 | Depui et al. |
| 6,136,344 A | 10/2000 | Depui et al. |
| 6,143,771 A | 11/2000 | Lindberg et al. |
| 6,147,103 A | 11/2000 | Anousis et al. |
| 6,150,380 A | 11/2000 | Lovqvist et al. |
| 6,162,816 A | 12/2000 | Bohlin et al. |
| 6,166,213 A | 12/2000 | Anousis et al. |
| 6,183,776 B1 | 2/2001 | Depui et al. |
| 6,248,363 B1 * | 6/2001 | Patel et al. .................. 424/497 |
| 6,274,173 B1 | 8/2001 | Sachs et al. |
| 6,284,271 B1 | 9/2001 | Lundberg et al. |
| ,192,299 A1 * | 12/2002 | Taneja et al. ................ 424/717 |
| 2002/0025342 A1 | 2/2002 | Linder et al. |
| 2002/0192299 A1 | 12/2002 | Taneja et al. |

FOREIGN PATENT DOCUMENTS

| | | |
|---|---|---|
| EP | 1004305 A1 | 5/2000 |
| EP | 0636364 B1 | 9/2000 |
| ES | 2024993 | 12/1990 |
| GB | 2189698 | 11/1987 |
| JP | 45 039541 | 12/1970 |
| JP | 45 039543 | 12/1970 |
| JP | 46 009580 | 11/1971 |
| JP | 46 009581 | 11/1971 |
| JP | 48 103567 | 12/1973 |
| JP | 49 005967 | 1/1974 |
| JP | 49 013172 | 2/1974 |
| JP | 49 020173 | 2/1974 |
| JP | 49 020174 | 2/1974 |
| JP | 49 041198 | 7/1974 |
| JP | 49 093537 | 9/1974 |
| JP | 49 095997 | 9/1974 |
| JP | 50 052065 | 5/1975 |
| JP | 50 112373 | 9/1975 |
| JP | 50 142565 | 11/1975 |
| JP | 51 016669 | 2/1976 |
| JP | 51 131875 | 11/1976 |
| JP | 52 005769 | 1/1977 |
| JP | 52 014776 | 2/1977 |
| JP | 52 097978 | 8/1977 |
| JP | 52 102416 | 8/1977 |
| JP | 53 059675 | 5/1978 |
| JP | 55 019211 | 5/1980 |
| JP | 56 061311 | 5/1981 |
| JP | 61 221117 | 10/1986 |
| JP | 62 145083 A | 6/1987 |
| JP | 62 258316 A | 11/1987 |
| JP | 62 258320 A | 11/1987 |
| JP | 62 277322 A | 12/1987 |
| JP | 62 283964 | 12/1987 |
| JP | 02 022225 | 1/1990 |
| JP | 03 163018 | 11/1990 |
| JP | 03 034967 | 2/1991 |
| JP | 03 048680 | 3/1991 |
| JP | 03 052887 | 3/1991 |
| JP | 05 117268 | 5/1993 |
| JP | 05 194225 | 8/1993 |
| JP | 05 255088 | 10/1993 |
| JP | 05 294831 | 11/1993 |
| JP | 06 092853 | 4/1994 |
| JP | 06 100449 | 4/1994 |
| JP | 07 033659 | 2/1995 |
| JP | 09 087110 | 3/1997 |
| JP | 10 017470 | 1/1998 |
| JP | 10 017471 | 1/1998 |
| JP | 2000 212180 | 2/2000 |
| JP | 2000 355540 | 12/2000 |
| KR | 9603605 B1 | 3/1996 |
| KR | 9611238 B1 | 8/1996 |
| KR | 9611390 B1 | 8/1996 |
| RO | 88351 | 4/1986 |
| WO | WO 9204898 A1 | 4/1992 |
| WO | WO 9208716 A1 | 5/1992 |
| WO | WO 9305770 A1 | 4/1993 |
| WO | WO 9400112 | 1/1994 |
| WO | WO 9402140 A1 | 2/1994 |
| WO | WO 9402141 A1 | 2/1994 |
| WO | WO 9501783 A1 | 1/1995 |
| WO | WO 9507913 A1 | 3/1995 |
| WO | WO 9515962 A1 | 6/1995 |
| WO | WO 9523594 A1 | 9/1995 |
| WO | WO 9532957 A1 | 12/1995 |
| WO | WO 9532959 A1 | 12/1995 |
| WO | WO 9601612 A1 | 1/1996 |
| WO | WO 9601622 A1 | 1/1996 |
| WO | WO 9601623 A1 | 1/1996 |
| WO | WO 9601624 A1 | 1/1996 |
| WO | WO 9601625 A1 | 1/1996 |

| | | |
|---|---|---|
| WO | WO 9602236 A1 | 2/1996 |
| WO | WO 9616959 A1 | 6/1996 |
| WO | WO 9624338 A1 | 8/1996 |
| WO | WO 9624375 A1 | 8/1996 |
| WO | WO 9638175 A1 | 12/1996 |
| WO | WO 9702020 | 1/1997 |
| WO | WO 9702021 | 1/1997 |
| WO | WO 9709964 A1 | 3/1997 |
| WO | WO 9725030 A1 | 7/1997 |
| WO | WO 9725064 A1 | 7/1997 |
| WO | WO 9725065 A1 | 7/1997 |
| WO | WO 9725066 A1 | 7/1997 |
| WO | WO 9741114 A1 | 11/1997 |
| WO | WO 9748380 A1 | 12/1997 |
| WO | WO 9800114 A2 | 1/1998 |
| WO | WO 9802368 A1 | 1/1998 |
| WO | WO 9816228 A1 | 4/1998 |
| WO | WO 9828294 Al | 7/1998 |
| WO | WO 9840054 A1 | 9/1998 |
| WO | WO 9850019 A1 | 11/1998 |
| WO | WO 9853803 A1 | 12/1998 |
| WO | WO 9854171 A1 | 12/1998 |
| WO | WO 9900380 A1 | 1/1999 |
| WO | WO 9908500 A2 | 2/1999 |
| WO | WO 9925323 A1 | 5/1999 |
| WO | WO 9925711 A1 | 5/1999 |
| WO | WO 9927917 A1 | 6/1999 |
| WO | WO 9929299 A1 | 6/1999 |
| WO | WO 9929320 A1 | 6/1999 |
| WO | WO 9932091 A1 | 7/1999 |
| WO | WO 9932093 A1 | 7/1999 |
| WO | WO 9945004 A1 | 9/1999 |
| WO | WO 9953918 A1 | 10/1999 |
| WO | WO 9955705 A1 | 11/1999 |
| WO | WO 9955706 A1 | 11/1999 |
| WO | WO 0001372 A1 A3 | 1/2000 |
| WO | WO 0009092 A1 | 2/2000 |
| WO | WO 0015195 A1 | 3/2000 |
| WO | WO 0010999 A2 A3 | 3/2000 |
| WO | WO 0027366 A1 | 5/2000 |
| WO | WO 0026185 A2 A3 | 5/2000 |
| WO | WO 0028975 A2 A3 | 5/2000 |
| WO | WO 0030612 A1 | 6/2000 |
| WO | WO 0035448 A1 | 6/2000 |
| WO | WO 0044744 A1 | 8/2000 |
| WO | WO 0045817 A1 | 8/2000 |
| WO | WO 0050038 A1 | 8/2000 |
| WO | WO 0069438 A1 | 11/2000 |
| WO | WO 0078293 A1 | 12/2000 |
| WO | WO 0103707 A1 | 1/2001 |
| WO | WO 0124780 A2 | 4/2001 |
| WO | WO 0134573 A1 | 5/2001 |
| WO | WO 03017980 A1 | 3/2003 |

OTHER PUBLICATIONS

Al–Assi, et al., "Treatment of *Helicobacter Pylori* Infection with Omeprazole–Amoxicillin Combination Therapy Versus Ranitidine/Sodium Bicarbonate–Amoxicillin", *The American Journal of Gastroenterology*, Vol. 90, No. 9, pp. 1411–1414 (Sep. 1995).

Andersson, et al., "Pharmacokinetic Studies with Esomeprazole, the (S)–Isomer of Omeprazole", *Clinical Pharmacokinetics*, Vol. 40, No. 6, pp. 411–426 (2001).

Andersson, T., "Pharmacokinetics, Metabolism and Interactions of Acid Pump Inhibitors: Focus on Omeprazole, Lansoprazole and Pantoprazole", *Clin. Pharacokinet.*, Vol. 31, No. 1, pp. 9–28 (Jul. 1996).

Andersson, T., et al., "Pharmacokinetics and Bioavailability of Omeprazole After Single and Repeated Oral Administration in Healthy Subjects", *Br. J. Clin. Pharmac.*, Vol. 29, pp. 557–563 (1990).

Andersson, T., et al., "Pharmacokinetics of [$^{14}$C]Omeprazole in Patients with Liver Cirrhosis", *Clin Pharmacokinet.*, Vol. 24, No. 1, pp. 71–78 (1993).

Andersson, T., et al., "Pharmacokinetics of Various Single Intravenous and Oral Doses of Omeprazole", *European Journal of Clinical Pharmacology*, Vol. 39, pp. 195–197 (1990).

Arvidsson, et al., "Peak Distortion in the Column Liquid Chromatographic Determination of Omeprazole Dissolved in Borax Buffer",*Journal of Chromatography*, Vol. 586, Part 2, pp. 271–276 (1991).

Balaban, D., et al., "Nasogastic Omeprazole: Effects on Gastric pH in Critically Ill Patients", *The American Journal of Gastroenterology*, Vol. 92, No. 1, pp. 79–83 (1997).

Ballard, E., et al., "Bioequivalence Between Lansoprazole Sachet for Suspension and Intact Capsule," *Gastroenterology*, Vol. 120 (No. %, Suppl. 1), p. A–245 (2001).

Ballesteros, et al., "Bolus or Intravenous Infusion of Rantidine: Effects on Gastric pH and Acid Secreation. A Comparison of Relative Efficacy and Cost"., *Annals of Internal Medicine*, Vol. 112, No. 5, pp. 334–339 (1990).

Barie & Hariri, "Theraueptic Use of Omeprazole for Refractory Stress–Induced Gastric Mucosal Hemorrage", *Critical Care Medicine*, Vol. 20, No. 6, pp. 899–901 (1992).

Beekman, S. M., "Preparation and Properties of New Gastric Antacids I", *J. Pharm Assoc.* Vol. 49, pp. 191–200, (1960).

Blum, A., "Therapeutic Approach to Ulcer Healing," *The Americal Journal of Medicine*, Volume 79 (Suppl. 2C), pp. 8–14 (Aug. 30, 1985).

Bone, "Let's Agree on Terminology: Definition of Sepsis", *Critical Care Medicine*, Vol. 19, No. 7, pp. 973–976 (Jul. 1991).

Borrero, et al., "Antacids vs. Sucralfate in Preventing Acute Gastrointestional Tract Bleeding in Abdominal Aortic Surgery. A Randomized Trial in 50 Patients", *Arch. Surg.*, Vol. 121, pp. 810–812 (Jul. 1986).

Brunton, *The Pharmacologic Basis of Therapeutics*, p. 907 (1990).

Cantu & Korek, "Central Nervous System Reactions to Histamine–2 Receptor Blockers", *Annals of Internal Medicine*, Vol. 114, No. 12, pp. 1027–1034 (1991).

Caos, A., et al., "Rabeprazole for the Prevention of Pathologic and Symptomatic Relapse of Erosive or Ulcerative Gastroesophageal Reflux Disease", *The Americal Journal of Gastroenterology*, Vol. 95, No. 11, pp. 3081–3088 (2000).

Carroll, M., et al., "Nasogastric Administration of Omeprazole for Control of Gastric pH" *10$^{th}$ World Congresses of Gastroenterology*, Abstracts (Oct. 2–7, 1994).

Cedergerg, C., et al., "Omeprazole: Pharmacokinetics and Metabolism in Man", *Scand. J. Gastroenterol.*, Vol. 24, Suppl. 166, pp. 33–40 (1989).

Cedergerg, et al., "Effect of Once Daily Intravenous and Oral Omeprazole on 24–Hour Intragastric Acidity in Healthy Subjects", *Scand. J. Gastroenterol.*, Vol. 28, No, 2, pp. 179–184 (Feb. 1993).

Ching, et al., "Antacids—Indications and Limitations", *Drugs*, Vol. 47, No. 2, pp. 305–317 (Feb. 1994).

Cioffi, et al., "Comparison of Acid Neutralizing and Non-acid Neutralizing Stress Ulcer Prophylaxis in Thermally Injured Patients", *The Journal of Trauma*, Vol. 36, pp. 541–547 (1994).

Cook, et al., "Nosocomial Pneumonia and the Role of Gastric pH: A Meta Analysis", *Chest*, Vol. 100, No. 1, pp. 7–13 (Jul. 1991).

Cook, et al., "Risk Factors for Gastrointestinal Bleeding in Critically Ill Patients. Canadian Critical Care Trial Groups", *The New England Journal of Medicine*, Vol. 330, No. 6, pp. 377–381 (Feb. 10, 1994).

Cook, et al., "Stress Ulcer Prophylaxis in the Critically Ill: A Meta Analysis", *The Americal Journal of Medicine*, Vol. 91, pp. 519–527 (Nov. 1991).

Crill, et al., "Upper Gastrointestinal Tract Bleeding in Critically Ill Pediatric Patients", *Pharmacotherapy*, Vol. 19, No, 2, pp. 162–180 (Feb. 1999).

Czaja, et al., "Acute Gastroduodenal Disease After Thermal Injury: An Endoscopic Evaluation of Incidence and Natural History", *The New England Journal of Medicine*, Vol. 291, pp. 925–929 (Oct. 31, 1974).

Deakin, et al., "Therapeutic Progress—Review XXXIII: Are We Making Progress in the Drug Treatment of Oesophageal Disease?", *Journal of Clinical Pharmacy and Therapeutics*, Vol. 13, No. 6, pp. 365–374 (Dec. 1988).

Diiorio, et al., "Aluminum and Phosphorus Urinary Excretion After Modifying Gastric Acid Secretion in Chronic Renal Failure", *Trace Elements and Electrolytes*, Vol. 13, No, 2, pp. 96–101 (1996).

Diiorio, et al., "Aluminum and Phosphorus Urinary Excretion After Modifying Gastirc Acid Secretion in Normal Subjects", *Trace Elements and Electrolytes*, Vol. 13, No. 1, pp. 47–49 (1996).

Digiacinto, et al., "Stability of Suspension Formulations of Lansoprazole and Omeprazole Stored in Amber–Colored Plastic Oral Syringes", *Annals of Pharmacotherapy*, Vol. 34, No. 5, pp. 600–605 (May 2000).

Doan, et al., "Comparative Pharmacokinetics and Pharmacodynamics of Lansoprazole Oral Capsules and Suspension in Healthy Subjects", *American Journal of Health–System Pharmacists*, Vol. 58, No. 16, pp. 1512–1519 (Aug. 15, 2001).

Dobkin, et al., "Does pH Paper Accurately Reflect Gastric pH?", *Critical Care Medicine*, Vol. 18, pp. 985–988 (Sep. 1990).

Driks, et al., "Nosocomial Pneumonia in Intubated Patients Given Sucralfate as Compared with Antacids or Histamine Type 2 Blockers. The Role of Gastric Colonization", New England Journal Medicine, Vol. 317, pp. 1376–1382 (1987).

Eisenberg, et al., "Prospective Trial Comparing a Combination pH Probe–Nasogastric Tube with Aspirated Gastric pH in Intensive Care Unit Patients", *Critical Care Medicine*, Vol. 18, No. 10, 1092–1095 (1990).

Epke, A., et al., "Effect of Various Salts on the Stability of Lansoprazole, Omeprazole, and Pantoprazole as Determined by High–Performance Liquid Chromatography", *Drug Development and Industrial Pharmacy*, Vol. 25, No. 9, pp. 1057–1065 (1999).

Fabian, et al., "Pneumonia and Stress Ulceration in Severely Injured Patients. A Prospective Evaluation of the Effects of Stress Ulcer Prophylaxis", *Arch. Surg.*, Vol. 128, pp. 185–191 (1993).

Fellenius, et al., "Substituted Benzimidazoles Inhibit Gastric Acid Secretions by Blocking H+/K+–ATPase", *Nature*, Vol. 290, Part 5802, pp. 159–161 (1981).

Fiddian–Green, et al., Predictive Value of Intramural pH and Other Risk Factors for Massive Bleeding from Stress Ulceration, *Gastroenterology*, Vol. 85, No. 3, pp. 613–620 (1983).

Fitton, A., et al., "Pantoprazole, A Review of its Pharmacological Properties and Therapeutic Use in Acid–Related Disorders", *Drugs*, Vol. 51, No. 3, pp. 460–482 (Mar. 1996).

Fryklund, et al., Function and Structure of Parietal Cells After H+/K+–ATPase Blockade, *Americal Journal of Physiology*, Vol. 254, pp. G399–407 (1988).

Fuchs, C., "Antacids, Their Function, Formulation and Evaluation", *Drug and Cosmetic Industry*, Vol. 64, pp. 692–773, (1949).

Gafter, et al., "Thrombocytopenia Associated with Hypersensitivity to Rantidine: Possible Cross–Reactivity with Cimetidine", Americal Journal of Gastroenterology, Vol. 84, No. 5, pp. 560–562 (1989).

Garner, et al., "CDC Definitions for Noscomial Infections", *American Journal Infection Control*, Vol. 16, No. 7, pp. 128–140 (1988).

Garnett, "Efficacy, Safety, and Cost Issues in Managing Patients with Gastroesophageal Reflux Disease", *Am. J. Hosp. Pharm.*, Vol. 50, No. 4 (Suppl. 1), pp. S11–18 (Apr. 1993).

Gray, et al., "Influence of Insulin Antibodies on Pharmacokinetics and Bioavailability of Recombinant Human and Highly Purified Beef Insulins in Insulin Dependent Diabetics", *British Medical Journal*, Vol. 290, pp. 1687–1691 (Jun. 8, 1985).

Gray, et al., "Influence of Insulin Antibodies on Pharmacokinetics and Bioavailability of Recombinant Human . . . ", *British Medical Journal*, 290: 1687–1690 (1985).

Hardy, et al., "Inhibition of Gastric Secretion by Omeprazole and Efficiency of Calcium Carbonate on the Control of Hyperphosphatemia in Patients on Chronic Hemodialysis", *Artificial Organs*, Vol. 22, No. 7, pp. 569–573 (Jul. 1998).

Hatlebakk, J., et al., "Lansoprazole Capsules and Amoxicillin Oral Suspension in the Treatment of Peptic Ulcer Disease", *Scand. J. Gastroenterol.*, Vol. 30, No. 11, pp. 1053–1057 (1995).

Heath, et al., "Intragastic pH Measurement Using a Novel Disposable Sensor", *Intesive Care Medicine*, Vol. 14, No. 3, pp. 232–235 (1988).

Hixson, et al., "Current Trends in the Pharmacotherapy for Gastroesophageal Reflux Disease", *Arch. Intern. Med.*, Vol. 152, No. 4, pp. 717–723 (Apr. 1992).

HIXSON, et al., "Current Trends in the Pharmacotherapy for Peptic Ulcer Disease", *Arch. Intern. Med.*, Vol. 152, No. 4, pp. 726–732 (Apr. 1992).

Holbert, J. et al., "A Study of Antacid Buffers: I. The Time Factor in Neutralization of Gastric Acidity", *Journal of The American Pharmaceutical Association (Scientific Edition)*, Vol. 36, pp. 149–151 (1947).

Holt, S., et al., "Omeprazole, Overview and Opinion", *Digestive Diseases and Sciences*, Vol. 36, No. 4, pp. 385–393 (Apr. 1991).

Horn, J., "The Proton–Pump Inhibitors: Similarities and Differences", *Clinical Therapeutics*, Vol. 22, No. 3, pp. 266–280 (2000).

Howden, et al., "Oral Pharmacokinetics of Omeprazole", *European Journal of Clinical Pharmacology*, Vol. 26, pp. 641–643 (1984).

Humphries, et al., "Review Article: Drug Interactions with Agents Used to Treat Acid–Related Diseases", *Alimentary Pharmacology & Therapeutics*, Vol. 13, Suppl. 3, pp. 18–26 (Aug. 1999).

Jungnickel, P., "Pantoprazole: A New Proton Pump Inhibitor", *Clinical Therapeutics*, Vol. 22, No. 11, pp. 1268–1293 (2000).

Karol, M. et al., "Pharmacokinetics of Lansoprazole in Hemodialysis Proteins", *J. Clin. Pharmacol*, Vol. 35, pp. 815–820 (Aug. 1995).

Kihira, K., et al., "Endoscopic Topical Therapy for the Treatment of *Heliobacter Pylori* Infection", *Journal of Gastroenterology*, Vol. 31, Suppl. 9, pp. 66–68 (Nov. 1996).

Kiilrich, et al., "Effect of Intravenous Infusion of Omeprazole and Rantidine on Twenty–Four–Hour Intragastric pH", *Digestion*, Vol. 56, pp. 25–30 (1995).

Korponay–Szabo, I.,et al., "High Acid Buffering Capacity of Protein Hydrolysate Infant Formulas", *Journal of Pediatric Gastroenterology and Nutrition*, Vol. 31, Supplement 2, Abstract 956 (Aug. 5–9, 2000).

Kromer, "Similarities and Differences in the Properties of Substituted Benzimidazoles: A Comparison Between Pantoprazole and Related Compounds", *Digestion*, Vol. 56, No. 6, pp. 443–454 (1995).

Kromer, et al., "Differences in pH–Dependent Activation Rate of Substituted Benzimidazoles and Biological in vitro Correlates", *Pharmacology*, Vol. 56, pp. 57–70 (1998).

Laggner, et al., "Prevention of Upper Gastrointestinal Bleeding in Long Term Ventilated Patients", *American Journal of Medicine*, Vol. 86, Suppl. 6A, pp. 81–84 (Jun. 9, 1989).

Landahl, S., et al., "Pharmacokinetic Study of Omeprazole in Elderly Healthy Volunteers", *Clin. Pharmacokinet.*, Vol. 23, No. 6, pp. 469–476 (1992).

Larson, C., et al., "Bioavailability and Efficacy of Omeprazole Given Orally and By Nasogastric Tube", *Digestive Diseases and Sciences*, Vol. 41, No. 3, pp. 475–479 (Mar. 1996).

Larson, et al., "Gastric Response to Severe Head Injury", *Americal Journal of Surgery*, Vol. 147, pp. 97–105 (Jan. 1984).

Larsson, et al., "Gastric Acid Antisecretory Effect of Two Different Dosage Forms of Omeprazole During Prolonged Oral Treatment in the Qastric Fistula Dog", Vol. 23, No. 8, pp. 1013–1019 (1988).

Lasky, M., et al., "A Prospective Study of Omeprazole Suspension to Prevent Clinically Significant Gastrointestinal Bleeding from Stress Ulcers in Mechanically Ventilated Trauma Patients", *The Journal of Trauma: Injury Infection, and Critical Care*, Vol. 44, No. 3, pp. 527–533 (Mar. 1998).

Lin, M., et al., "Evaluation of Buffering Capacity and Acid Neutralizing pH Time Profile of Antacids", *J Formos Med Assoc*, Vol. 97, No. 10, pp. 704–710 (1998).

Lind, et al., "Inhibition of Basal and Betazole—and Sham–Feeding–Induced Acid Secretion by Omeprazole in Man", *Scand. J. Gastroenterol*, Vol. 21, No. 8, pp. 1004–1010 (1986).

Lockhart, S. et al., "A Lansoproazole Suspension Formulation as an Alternative to Capsules for Oral Administration", *World Congresses of Gastroenterology*, Abstract Exh A2074 (Sep. 6–11, 1998).

Londong, et al., "Dose–Response Study of Omeprazole on Meal–Stimulated Gastric–Acid Secretion and Gastrin Release", *Gastroenterology*, Vol. 85, No. 6, pp. 1373–1378 (1983).

Maconi, et al., "Prolonging Proton Pump Inhibitor–Based Anti–*Helicobacter Pylori* Treatment from One to Two Weeks in Duodenal Ulcer: Is it Worthwhile?", *Digest Liver Disease*, Vol. 32, pp. 275–280 (May 2000).

Marrone & Silen, "Pathogenesis, Diagnosis and Treatment of Acute Gastric Mucosa Lesions", *Clinics Gastroenterology*, Vol. 13, No. 2, pp. 635–650 (May 1984).

Martin, A., et al., *Physical Pharmacy—Physical Chemicals Principles in the Pharmaceutical Sciences*, Fourth Edition, (1993).

Martin, L., et al., "Continuous Intravenous Cimetidine Decreases Stress–Related Upper Gastrointestinal Hemorrhage Without Promoting Pneumonia", *Critical Care Medicine*, Vol. 21, Vol. 1, pp. 19–30 (1993).

Maxwell, et al., "Control of Gastric pH in a Critical Care Unit: Physician Behavior and Pharmacologic Effectiveness",*Am. Rev. Respir. Dis.*, Vol. 143, No. 4 (Part 2), p. A482 (1991).

McAndrews, et al., "Omeprazole and Lansoprazole Suspensions for Nasogastric Administration", *American Journal of Health–System Pharm.*, Vol. 56, p. 81 (Jan. 1, 1999).

McTavish, D., et al., "Omeprazole, An Updated Review of its Pharmacology and Therapeutic Use in Acid–Related Disorders" by *Drugs*, Vol. 42, No. 1, pp. 138–170 (1991).

Meiners, et al., "Evaluation of Various Techniques to Monitor Intragastric pH", *Arch. Surg.*, Vol. 117, No. 3, pp. 288–291 (1982).

Metzler, M., Advances in the Use of PPI's from Efficacy to Effectiveness, *Presentation: Simplified Omeprazole Suspension* (1999).

Mohiuddin, M. A., et al., "Effective Gastric Acid Suppression After Oral Administration of Enteric–Coated Omeprazole Granules", *Digestive Diseases and Sciences*, Vol. 42, No. 4, pp. 715–719 (Apr. 1997).

Nakagawa, et al., "Lansoprazole—Phase I Study of Lansoprazole (AG–1749)—Antiulcer Agent", *Journal of Clinical Therapeutics & Medicines*, Vol. 7, No. 1, pp. 33–50 (1991).

Nakamura, M, et al., "Effect of Combined Administration of Lansoprazole and Sofalcone on Microvascular and Connective Tissue Regeneration After Ethanol–induced Mucosal Damage", *Journal of Clinical Gastroenterology*, Vol. 27, Supp. 1, pp. 170–177 (1998).

Naunton, M., et al., "Overuse of Proton Pump Inhibitors", *Journal of Clinical Pharmacy and Therapeutics*, Vol. 25, pp. 333–340 (2000).

On & Carroll, "Electrolyte and Acid–base Disorders", *The Pharmacologic Approach to the Critically Ill Patient*, pp. 957–968 (Chernow, B. ed. 1994).

Oosterhuis, et al. "Omeprazole: Pharmacology, Pharmacokinetics and Interactions", *Digestion*, Vol. 44, Suppl. 1, pp. 9–17 (1989).

Osler, et al., "Effect of Omeprazole on the Phosphate–Binding Capacity of Calcium Carbonate", *Nephron*, Vol. 69, pp. 89–90 (1995).

Ostro, et al., "Control of Gastric pH with Cimetidine: Boluses Versus Primed Infusions", *Gastroenterology*, Vol. 89, No. 3, pp. 532–537 (1985).

Paul, J., et al., "Pantoprazole Bicarbonate Suspension (PBS) Provides Oral Bioavailability Comparable to Tablet", *Critical Care Medicine*, (Feb. 2001).

Peckman, H., "Alternative method for administering proton–pump inhibitors through nasogastric tubes" *Am. J. Health–Syst Pharm* Vol. 56, p. 1020, (May 15, 1999).

Peura & Johnson, "Cimetidine for Prevention and Treatment of Gastroduodenal Mucosal Lesions in Patients in an Intensive Care Unit", *Ann. Intern. Med.,* Vol. 103, pp. 173–177 (1985).

Phillips, D. H., "Interaction of Omperazole with DNA in Rat Tissues", *Mutagenesis,* Vol. 7, No. 4, pp. 277–283 (Jul. 1992).

Phillips, J. & Metzler, M., Poster Presentation presented at the Society for Critical Care Medicine Annual Meeting relating to SOS, (Jan. 1999).

Phillips, J., et al., "A Multicenter, Prospective, Randomized Clinical Trial of Continuous Infusion I.V. Ranitidine vs. Omeprazole Suspension in the Prophylaxis of Stress Ulcers", *Critical Care Medicine,* Vol. 26, No. 1 (Suppl.) p. A101, No. 222 (1998).

Phillips, J., et al., "A Prospective Study of Simplified Omeprazole Suspension for the Prophylaxis of Stress-related Mucosal Damage", *Critical Care Medicine,* Vol. 24, No. 11, pp. 1793–1800 (1996).

Phillips, J., et al., "Simplified Omeprazole Solution for the Prophylaxis of Stress-Related Mucosal Damage in Critically Ill Patients", *Critical Care Medicine,* Vol. 22, No. 1, p. A53 (Jan. 1994).

Phillips, J., et al., "The Stability of Simplified Lansoprazole Suspension (SLS)", *Gastroenterology,* Vol. 116, No. 4, p. G0382 (Apr. 1999).

Phillips, J., et al., "The Stability of Simplified Omeprazole Suspension (SOS)", *Critical Care Medicine,* Vol. 26, No. 1 (Suppl.) p. A101, No. 221 (1998).

Phillips, J., Presentation: "Problems with Administering Granules", *Overview of Omeprazole Suspension,* (1999/2000).

Phillips, J., Presentation: From Efficacy to Effectiveness Alternative Dosing of PPI's, *Overview of Omeprazole Suspension,* (Aug. 1998).

Phillips, J., Presentation: "Simplified Omeprazole Suspension (SOS)", (1998).

Phillips, J., Presentation: Stress–related Mucosal Damage, Optimizing Drug Therapy, *Prophylaxis of Stress Ulcers,* (1997).

Phillips, J., Presentation: Stress–related Mucosal Damage, Optimizing Drug therapy in the 1990's, *The University of Missouri Surgical Society Scientific Program,* (Jun. 1994).

Phillips, J., Presentation: Update on Acid–related Disorders, Optimizing Pharmacotherapy for the 1990's, *A Model for Optimizing Pharmacotherapy,* (1996).

Phillips, Project #5122: "Simplified Omeprazole Solution (S.O.S.)—Pharmacokinetic/Pharmacodynamic Study in Patients at Risk for Stress Related Mucosal Damage (SRMD)" (Approved Apr. 28, 1994).

Pickworth, et al., "Occurrence of Nosocomial Pneumonia in Mechanically Ventilated Trauma Patients: A Comparison of Sucralfate and Ranitidine", *Critical Care Medicine,* Vol. 21, No. 12, , pp. 1856–1862 (1993).

Pilbrant, "Principles for Development of Antacids", *Scand. J. Gastroenterol Suppl.,* Vol. 75, pp. 32–36 (1982).

Pilibrant, A., et al., "Development of an Oral Formulation of Omeprazole", *Scand. J. Gastrolenterol,* Vol. 20, (Suppl. 108) pp. 113–120 (1985).

Pipkin, et al., "Onset of Action of Antisecretory Drugs: Beneficial Effects of a Rapid Increase in Intragastric pH in Acid Reflux Disease", *Scand. J. Gastroenterol. Supp.,* Vol. 230, pp. 3–8 (1999).

Presentation on Overview of Omeprazole Suspension, Pharmacotherapy Related Outcomes Group Researching Effective Stress Ulcer Strategies, (2000).

Presentation on Overview of Omeprazole Suspension, Stress Ulcer Prophylaxis in the $21^{st}$ Century, (2001).

Prichard, et al., "Omeprazole: A Study of Its Inhibition of Gastric pH and Oral Pharmacokinetics After Morning or Evening Dosage", *Gastroenterology,* Vol. 88, Part 1, pp. 64–69 (1985).

Priebe & Skillman, "Methods of Prophylaxis in Stress Ulcer Disease", *World J. Surg.,* Vol. 5, Part 2, pp. 223–233 (Mar. 1981).

Quercia, R. A., et al., "Stability of Omeprazole in an Extemporaneously Prepared Oral Liquid", *American Journal of Health–System Pharmacy,* Vol. 54, pp. 1833–1936 (Aug. 15, 1997).

Regardh, C., et al., "The Pharmacokinetics of Omeprazole in Humans—A Study of Single Intravenous and Oral Doses", *Therapeutic Drug Monitoring,* Vol. 12, No. 2, pp. 163–172 (1990).

Regardh, et al., "Pharmacokinetics and Metabolism of Omeprazole in Animals and Man—An Overview", *Scand. J. Gastroenterology,* Vol. 108, pp. 79–94 (1985).

Rodrigo, et al., "Therapeutic Approach to Peptic Ulcer Relapse", *Methods Find Exp. Clinical Pharmacology,* Vol. 11 (Supp. 1), pp. 131–155 (1989).

Rohan, E., "Nasogastric Administration of Omeprazole", *The Australian Journal of Hospital Pharmacy,* Vol. 28, No. 3, pp. 174–176 (1998).

Roy, P., et al., "Zollinger–Ellison Syndrome—Clinical Presentation in 261 Patients", *Medicine,* Vol. 79, No. 6, pp. 379–411 (2000).

Ryan, et al., "Nosocomial Pneumonia During Stress Ulcer Prophylaxis with Cimetidine and Sucralfate", *Arch. Surg.,* Vol. 128, pp. 1353–1357 (Dec. 1993).

Sax, "Clinically Important Adverse Effects and Drug Interactions with H2–receptor Antagonists: An Update", *Pharmacotherapy,* Vol. 7, No. 6, Part 2, pp. 110S–115S (1987).

Schepp, "Stress Ulcer Prophylaxis: Still a Valid Option in the 1990's?", *Digestion,* Vol. 54, No. 4, pp. 189–199 (1993).

Schmassmann, et al., "Antacid Provides Better Restoration of Glandular Structures Within the Gastric Ulcer Scar Than Omeprazole", *Gut,* Vol. 35, No. 7, pp. 896–904 (Jul. 1994).

Schmassmann, et al., "Antacids in Experimental Gastric Ulcer Healing: Pharmacokinetics of Aluminum and Quality of Healing", *European Journal of Gastroenterology & Hepatology,* Vol. 5, Suppl. 3, pp. S111–S116 (1993).

Schuster, "Stress Ulcer Prophylaxis: In Whom? with What?", *Critical Care Medicine,* Vol. 21, Part 1, pp. 4–6 (Jan. 1993).

Sechet, et al., "Inhibition of Gastric Secretion by Omeprazole and Efficacy of Calcium Carbonate in the Control of Hyperphosphatemia in Patients on Maintenance Hemodialysis", *Nephrologie,* Vol. 20, No. 4, pp. 213–216 (1999).

Sechet, et al., Role of the Time of Administration of Calcium Carbonate in the Control of Hyperphophatemia in Patients on Maintenance Hemodialysis, *Nephrologie,* Vol. 20, No. 4, pp. 209–212 (1999).

Sharma, et al., "Oral Pharmacokinetics of Omerprazole and Lansoprazole After Single and Repeated Doses as Intact Capsules or as Suspensions in Sodium Bicarbonate", *Alimentary Pharmacology & Therapeutics,* Vol. 14, No. 7, pp. 887–892 (Jul. 2000).

Sharma, et al., "The Pharmacodynamics of Lansoprazole Administered Via Gastrostomy as Intact, Non–Encapsulated Granules", *Alimentary Pharmacology Therapy*, Vol. 12, pp. 1171–1174 (1998).

Sharma, V. et al., "Effect on 24–hour Intragastric Acidity of Simplified Omeprazole Solution (SOS) Administered Via Gastrostomy", *AJG*, Vol. 92, No. 9, p. 1625, Section 169 (1997).

Sharma, V., et al., "Simplified Lansoprazole Suspension—A Liquid Formulation of Lansoprazole—Effectively Suppresses Intragastric Acidity When Administered Through a Gastrostomy", *The American Journal of Gastroenterology*, Vol. 94, No. 7, pp. 1813–1817 (Jul. 1999).

Sharma, V., et al., "Simplified Lansoprazole Suspension (SLS): A Proton Pump Inhibitor (PPI) In a Liquid Formulation That Works", *AJG*, p. 1647, Section 153 (Sep. 1998).

Sharma, V., et al., "The Effects on Intragastric Acidity of Per–Gastrostomy Administration of An Alkaine Suspension of Omeprazole", *Aliment Pharmacol Ther*, Vol. 13, pp. 1091–1095 (1999).

Sharma, V., "Comparison of 24–hour Intragastric pH Using Four Liquid Formulations of Lansoprazole and Omeprazole", *American Journal of Health–System Pharmacists*, Vol. 56, Suppl 4, pp. S18–S21 (Dec. 1, 1999).

Shuman, et al., "Prophylactic Therapy for Acute Ulcer Bleeding: A Reappraisal", *Annals of Internal Medicine*, Vol. 106, Vol. 4, pp. 562–567 (1987).

Siepler, "A Dosage Alternative for H–2 Receptor Antagonists, Continuous–Infusion", *Clinical Therapy*, Vol. 8, Suppl. A, pp. 24–33 (1986).

Siepler, et al., "Selecting Drug Therapy for Patients With Duodenal Ulcers", *Clinical Pharmacy*, Vol. 9, No. 6, pp. 463–467 (Jun. 1990).

Sih, J., et al., "Studies on (H(+)–K+)–ATPase Inhibitors of Gastric Acid Secretion. Prodrugs of 2–[(2–Pyridinylmethyl)sulfinyl]benzimidazole Proton–Pump Inhibitors", *Journal of Medicine Chemistry*, Vol. 34, No. 3, pp. 1049–1062 (Mar. 1991).

Simms, et al., "Role of Gastric Colonization in the Development of Pneumonia in Critically Ill Trauma Patients: Results of a Prospective Randomized Trial", *The Journal of Trauma*, Vol. 31, No. 4, pp. 531–536 (1991).

Skillman, et al., "Respiratory Failure, Hypotension, Sepsis and Jaundice: A Clinical Syndrome Associated with Lethal . . . ", *Am. J. Surg.*, Vol. 117,Vol. 4, pp. 523–530 (1969).

Skillman, et al., "The Gastric Mucosal Barrier: Clinical and Experimental Studies in Critically Ill and Normal Man . . . ", *Am. Surg.*, Vol. 172, Vol. 4, pp. 564–584 (1970).

Smythe & Zarowitz, "Changing Perspectives of Stress Gastritis Prophylaxis", *The Annals of Pharmacotherapy*, Vol. 28, pp. 1073–1084 (Sep. 1994).

Spencer, C., et al., "Esomeprazole", *Drugs* 2000, Vol. 60, No. 2, pp. 321–329 (Aug. 2000).

Spychal & Wickman, "Thrombocytopenia Associated with Rantidine", *British Medical Journal*, Vol. 291, p. 1687 (Dec. 14, 1985).

Stratford, M. R., et al., "Nicotinamide Pharmacokinetics in Humans: Effect of Gastric Acid Inhibition, Comparison of Rectal vs Oral Administration and the Use of Saliva for Drug Monitoring", *Br. J. Cancer*, Vol. 74, No. 1, pp. 16–21 (Jul. 1996).

Takeuchi, et al., "Effects of Pantoprazole, A Novel H+/K+–ATPase Inhibitor, on Duodenal Ulcerogenic and Healing Responses in Rats: A Comparative Study with Omeprazole and Lansoprazole", *Journal of Gastroenterology and Hepatology.*, Vol. 14, No. 3, pp. 251–257 (1999).

Tanaka, et al., "Pathogenesis of the Earliest Epithelial Cell Damage Induced by Mepirizole and Cysteamine in the Rat Duodenum", *Japanese Journal of Pharmacology*, Vol. 51, No. 4, pp. 509–519 (Dec. 1989).

Tanaka, M., et al., "Differential Stereoselective Pharmacolkinetics of Pantoprazole, a Proton Pump Inhibitor in Extensive and Poor Metabolizers of Pantoprazole—A Preliminary Study", *Chirality*, Vol. 9, pp. 17–21 (1997).

Thomson, "Are the Orally Administered Proton Pump Inhibitors Equivalent? A Comparison of Lansoprazole, Omeprazole, Pantoprazole, and Rabeprazole", *Current Gastroenterology Reports*, Vol. 2, No. 6, pp. 482–493 (Dec. 2000).

Tryba, "Risk of Acute Stress Bleeding and Nosocomial Pneumonia in Ventilated Intensive Care Patients. Sucralfate vs. Antacids", *American Journal of Medicine*, Vol. 87 (3B) 117–24 (1987).

Tryba, "Stress Ulcer Prophylaxis—Quo Vadis?", *Intensive Care Medicine*, Vol. 20, pp. 311–313 (1994).

Tytgat, G., "Drug Therapy of Reflux Oesophagitis: An Update," *Scand. J. Gastroenterol.*, Vol. 24 (Suppl. 168), pp. 38–49 91989).

Vial, et al., "Side Effects of Ranitidine", *Drug Safety*, Vol. 6, pp. 94–117 (Mar./Apr. 1991).

Vincent, et al., "Concurrent Administration of Omeprazole and Antacid Does Not Alter the Pharmacokinetics and Pharmacodynamics of Dofetilide in Healthy Subjects", *Clinical Pharmacology & Therapeutics*, Vol. 59, No. 2 (PII–93), p. 182 (Feb. 1996).

Wade, Organic Chemistry, Pritice–Hall, Inc., Chapter 8, p. 349 (1987).

Walan, "Pharmacological Agents for Peptic Ulcer Disease", *Scand. J. Gastroenterol. Suppl.*, Vol. 19, No. 98, p. 1 (1984).

Wallmark, et al., "The Relationship Between Gastric Acid Secretion and Gastric H+/K+–ATPase Activity", *Journal of Biological Chemistry*, Vol. 260, No. 25, pp. 13681–13684 (1985).

Watanabe, K., et al., "Pharmacokinetic Evaluation of Omeprazole Suspension Following Oral Administration in Rats: Effect of Neutralization of Gastric Acid", *Acta Med Okayama*, Vol. 50, No. 4, pp. 219–222 (Aug. 1996).

Whipple, J., et al., "The Effect of Omeprazole/Sodium Bicarbonate Solution Administration on the Accuracy of Subsequent pH Measurements through the Nasogastric Tube", *Clinical Care Medicine*, Vol. 23, No. 1 Supplement, p. A69.

Whipple, J., et al., "The Effect of Omeprazole/Sodium Bicarbonate Solution Administration on the Accuracy of Subsequent pH Measurements through the Nasogastric Tube", *Critical Care Medicine*, Vol. 23, No. 1 Supplement, p. A69 (Jan. 1995).

Whipple, J., et al., "The Effect of Omeprazole/Sodium Bicarbonate Solution Administration on the Accuracy of Subsequent pH Measurements through the Nasogastric Tube", *Critical Care Medicine*, Vol. 23, No. 1 Supplement, p. A69 (Jan. 1995).

Whipple, J., et al., "The Effect of Omeprazole/Sodium Bicarbonate Solution Administration on the Accuracy of Subsequent pH Measurements through the Nasogastric Tube", *Critical Care Medicine,* Vol. 23, No. 1 Supplement, p. A69 (Jan. 1995).

Whipple, J., et al., "The Effect of Omeprazole/Sodium Bicarbonate Solution Administration on the Accuracy of Subsequent pH Measurements through the Nasogastric Tube", *Critical Care Medicine,* Vol. 23, No. 1 Supplement, p. A69 (Jan. 1995).

Whipple, J., et al., "The Effect of Omeprazole/Sodium Bicarbonate Solution Administration on the Accuracy of Subsequent pH Measurements through the Nasogastric Tube", *Critical Care Medicine,* Vol. 23, No. 1 Supplement, p. A69 (Jan. 1995).

Whipple, J., et al., "The Effect of Omeprazole/Sodium Bicarbonate Solution Administration on the Accuracy of Subsequent pH Measurements through the Nasogastric Tube", *Critical Care Medicine,* Vol. 23, No. 1 Supplement, p. A69 (Jan. 1995).

Whipple, J., et al., "The Effect of Omeprazole/Sodium Bicarbonate Solution Administration on the Accuracy of Subsequent pH Measurements through the Nasogastric Tube", Vol. 23, No. 1 (Suppl), p. A69 (Jan. 1995).

Wilder–Smith & Merki, "Tolerance During Dosing with H2 Receptor Antagonists: An Overview", *Scand. J. Gastroenterol.,* Vol. 193, pp. 14–19 (1992).

Yamakawa, T., "Synthesis and Structure–Activity Relationships of Substituted 2-[2-imidazolylsulfinyl)methyl] Anilines as a New Class of Gastric H+/K+(+)–ATPase Inhibitors, II.", *Chem Pharm Bull* (Tokyo), Vol. 40, No. 3, pp. 675–682 (Mar. 1992).

Yasuda, et al., "Antacids Have No Influence on the Pharmacokinetics of Rabeprazole, A New Proton Pump Inhibitor, In Healthy Volunteers", *International Journal of Clinical Pharmacology and Therapeutics,* Vol. 37, No. 5, pp. 249–253 (1999).

Zinner, et al., "The Prevention of Upper Gastro–Intestional Tract Bleeding in Patients in an Intensive Care Unit", *Surgery, Gynecology and Obstetrics,* Vol. 153, pp. 214–220 (Aug. 1981).

* cited by examiner

OVERALL PATIENT ENROLLMENT SCHEME

Graph 1

Graph 2

Graph 3

SUBSTITUTED BENZIMIDAZOLE DOSAGE FORMS AND METHODS OF USING SAME

This application is a continuation-in-part of U.S. patent application Ser. No. 09/901,942, filed on Jul. 9, 2001, which is a continuation-in-part of U.S. patent application Ser. No. 09/481,207, filed on Jan. 11, 2000, now U.S. Pat. No. 6,489,346, which is a continuation-in-part of U.S. patent application Ser. No. 09/183,422, filed on Oct. 30, 1998, now abandoned, which is a continuation-in-part of U.S. patent application Ser. No. 08/680,376, filed on Jul. 15, 1996, now U.S. Pat. No. 5,840,737, which claims priority to U.S. Provisional Application Serial No. 60/009,608, filed on Jan. 4, 1996. This application claims priority to all such previous applications, and such applications are hereby incorporated herein by reference.

TECHNICAL FIELD

The present invention relates to pharmaceutical preparations comprising substituted benzimidazole proton pump inhibiting agents.

BACKGROUND OF THE INVENTION

Omeprazole is a substituted benzimidazole, 5-methoxy-2-[(4-methoxy-3,5-dimethyl-2-pyridinyl) methyl]sulfinyl]-1H-benzimidazole, that inhibits gastric acid secretion. Omeprazole belongs to a class of anti secretory compounds called proton pump inhibitors proton pump inhibiting agents ("PPIs") that do not exhibit aniti-cholinergic or $H_2$ histamine antagonist properties. Drags of this class suppress gastric acid secretion by the specific inhibition of the $H^+$, $K^+$-ATPase enzyme system (proton pump) at the secretory surface of the gastric parietal cell.

Typically, omeprazole, lansoprazole and other proton pump inhibitors are formulated in an enteric-coated solid dosage form (as either a delayed-release capsule or tablet) or as an intravenous solution (as a product for reconstitution), and are prescribed for short-term treatment of active duodenal ulcers, gastric ulcers, gastroesophageal reflux disease (GERD), severe erosive esophagitis, poorly responsive symptomatic gastroesophageal reflux disease, and pathological hypersecretory conditions such as Zollinger Ellison syndrome. These conditions are caused by an imbalance between acid and pepsin production, called aggressive factors, and mucous, bicarbonate, and prostaglandin production, called defensive factors. These above-listed conditions commonly arise in healthy or critically ill patients, and may be accompanied by significant upper gastrointestinal bleeding.

$H_2$-antagonists, antacids, and sucralfate are commonly administered to minimize the pain and the complications related to these conditions. These drugs have certain disadvantages associated with their use. Some of these drugs are not completely effective in the treatment of the aforementioned conditions and/or produce adverse side effects, such as mental confusion, constipation, diarrhea, and thrombocytopenia. $H_2$-antagonists, such as ranitidine and cimetidine, are relatively costly modes of therapy, particularly in NPO patients, which frequently require the use of automated infusion pumps for continuous intravenous infusion of the drug.

Patients with significant physiologic stress are at risk for stress-related gastric mucosal damage and subsequent upper gastrointestinal bleeding (Marrone and Silen, *Pathogenesis, Diagnosis and Treatment of Acute Gastric Mucosa Lesions,* CLIN GASTROENTEROL 13:635–650 (1984)). Risk factors that have been clearly associated with the development of stress-related mucosal damage are mechanical ventilation, coagulopathy, extensive burns, head injury, and organ transplant (Zinner et al., *The Prevention of Gastrointestinal Tract Bleeding in Patients in an Intensive Care Unit,* SURG. GYNECOL. OBSTET., 153:214–220 (1981); Larson et al., *Gastric Response to Severe Head Injury,* AM. J. SURG. 147:97–105 (1984); Czaja et al., *Acute Gastroduodenal Disease After Thermal Injury: An Endoscopic Evaluation of Incidence and Natural History,* N ENGL. J. MED, 291:925–929 (1974); Skillman et al., *Respiratory Failure, Hypotension, Sepsis and Jaundice: A Clinical Syndrome Associated with Lethal Hemorrhage From Acute Stress Ulceration,* AM. J. SURG., 117:523–530 (1969); and Cook et al., *Risk Factors for Gastrointestinal Bleeding in Critically Ill Patients,* N. ENGL. J. MED., 330:377–381 (1994)). One or more of these factors are often found in critically ill, intensive care unit patients. A recent cohort study challenges other risk factors previously identified such as acid-base disorders, multiple trauma, significant hypertension, major surgery, multiple operative procedures, acute renal failure, sepsis, and coma (Cook et al., *Risk Factors for Gastrointestinal Bleeding in Critically Ill Patients,* N. ENGL. J. MED., 330:377–381 (1994)). Regardless of the risk type, stress-related mucosal damage results in significant morbidity and mortality. Clinically significant bleeding occurs in at least twenty percent of patients with one or more risk factors who are left untreated (Martin et al., *Continuous Intravenous cimetidine Decreases Stress-related Upper Gastro-intestinal Hemorrhage Without Promoting Pneumonia,* CRIT. CARE MED., 21:19–39 (1993)). Of those who bleed, approximately ten percent require surgery (usually gastrectomy) with a reported mortality of thirty percent to fifty percent (Czaja et al., *Acute Gastroduodenal Disease After Thermal Injury: An Endoscopic Evaluation of Incidence and Natural History,* N ENGL. J. MED, 291:925–929 (1974); Peura and Johnson, *Cimetidine for Prevention and Treatment of Gastroduodenal Mucosal Lesions in Patients in an Intensive Care Unit,* ANN INTERN MED., 103:173–177 (1985)). Those who do not need surgery often require multiple transfusions and prolonged hospitalization. Prevention of stress-related upper gastrointestinal bleeding is an important clinical goal.

Omeprazole (Prilosec(®), lansoprazole (Prevacid®) and other proton pump inhibitors reduce gastric acid production by inhibiting $H^{30}$, $K^+$-ATPase of the parietal cell—the final common pathway for gastric acid secretion (Fellenius et al., *Substituted Benzimidazoles Inhibit Gastric Acid Secretion by Blocking $H^+$, $K^+$-ATPase,* NATURE, 290:159–161 (1981); Wallmark et al, *The Relationship Between Gastric Acid Secretion and Gastric $H^+$, $K^+$-ATPase Activity,* J. BIOL.CHEM., 260:13681–13684 (1985); Fryklund et al., *Function and Structure of Parietal Cells After $H^+$, $K^+$-ATPase Blockade,* AM. J. PHYSIOL., 254 (3 PT 1); G399–407 (1988)).

Proton pump inhibitors contain a sulfinyl group in a bridge between substituted benzimidazole and pyridine rings, as illustrated below.

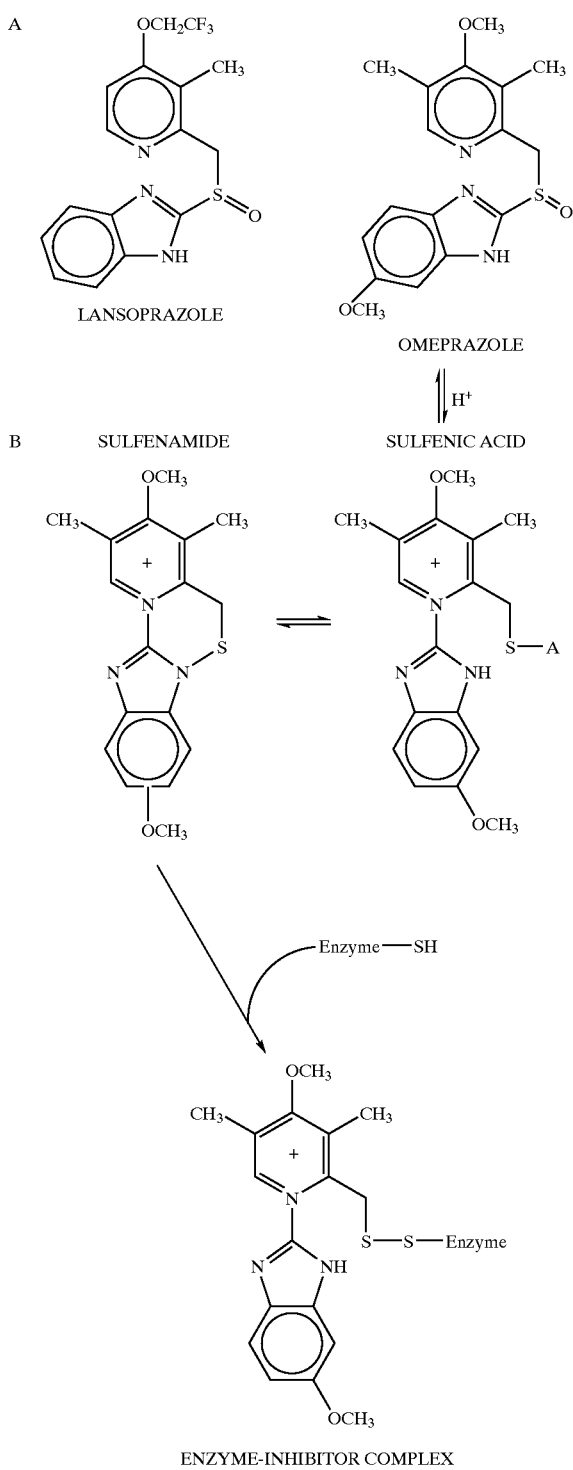

At neutral pH, omeprazole, lansoprazole and other proton pump inhibitors are chemically stable, lipid-soluble, weak bases that are devoid of inhibitory activity. These neutral weak bases reach parietal cells from the blood and diffuse into the secretory canaliculi, where the drugs become protonated and thereby trapped. The protonated agent rearranges to form a sulfenic acid and a sulfenamide. The sulfenamide interacts covalently with sulfhydryl groups at critical sites in the extracellular (luminal) domain of the membrane-spanning $H^+$, $K^+$-ATPase (Hardman et al., *Good-*

*man & Gilman's The Pharmacological Basis of Therapeutics*, p. 907 ($9^{th}$ ed. 1996)). Omeprazole and lansoprazole, therefore, are prodrugs that must be activated to be effective. The specificity of the effects of proton pump inhibitors is also dependent upon: (a) the selective distribution of $H^+$, $K^+$-ATPase; (b) the requirement for acidic conditions to catalyze generation of the reactive inhibitor; and (c) the trapping of the protonated drug and the cationic sulfenamide within the acidic canaliculi and adjacent to the target enzyme. (Hardman et al., 1996).

Omeprazole and lansoprazole are available for oral administration as enteric-coated granules in gelatin capsules. Other proton pump inhibitors such as rabeprazole and pantoprazole are supplied as enteric-coated dosage forms. The enteric dosage forms of the prior art have been employed because they are acid labile; thus, it is important that these drugs not be exposed to low pH gastric acid prior to absorption. Although these drugs are stable at alkaline pH, they are destroyed rapidly as pH falls (e.g., by gastric acid). Therefore, if the micro-encapsulation or the enteric coating is disrupted (e.g., trituration to compound a liquid, or chewing the capsule), the dosage forms of the prior art will be exposed to degradation by the gastric acid in the stomach.

The absence of an intravenous or oral liquid dosage form in the United States has limited the testing and use of omeprazole, lansoprazole and rabeprazole in the critical care patient population. Barie et al., *Therapeutic Use of Omeprazole for Refractory Stress-induced Gastric Mucosal Hemorrhage*, CRIT. CARE MED., 20:899–901 (1992) have described the use of omeprazole enteric-coated pellets administered through a nasogastric tube to control gastrointestinal hemorrhage in a critical care patient with multi-organ failure. However, such pellets are not ideal as they can aggregate and occlude such tubes, and they are not suitable for patients who cannot swallow the pellets. AM J. HEALTH-SYST PHARM 56:2327–30 (1999).

Proton pump inhibitors such as omeprazole represent an advantageous alternative to the use of $H_2$-antagonists, antacids, and sucralfate as a treatment for complications related to stress-related mucosal damage. However, in their current form (capsules containing enteric-coated granules or enteric-coated tablets), proton pump inhibitors can be difficult or impossible to administer to patients who are either unwilling or unable to swallow tablets or capsules, such as critically ill patients, children, the elderly, and patients suffering from dysphagia. Therefore, it would be desirable to formulate a proton pump inhibitor solution or suspension which can be enterally delivered to a patient thereby providing the benefits of the proton pump inhibitor without the drawbacks of the current enteric-coated solid dosage forms.

Omeprazole, the first proton pump inhibitor introduced into use, has been formulated in many different embodiments such as in a mixture of polyethylene glycols, adeps solidus and sodium lauryl sulfate in a soluble, basic amino acid to yield a formulation designed for administration in the rectum as taught by U.S. Pat. No. 5,219,870 to Kim.

U.S. Pat. No. 5,395,323 to Berglund ('323) discloses a device for mixing a pharmaceutical from a solid supply into a parenterally acceptable liquid form for parenteral administration to a patient. The '323 patent teaches the use of an omeprazole tablet which is placed in the device and dissolved by normal saline, and infused parenterally into the patient. This device and method of parenteral infusion of omeprazole does not provide the omeprazole solution as an enteral product, nor is this omeprazole solution directly administered to the diseased or affected areas, namely the stomach and upper gastrointestinal tract, nor does this omeprazole formulation provide the immediate antacid effect of the present formulation.

U.S. Pat. No. 4,786,505 to Lovgren et al. discloses a pharmaceutical preparation containing omeprazole together with an alkaline reacting compound or an alkaline salt of omeprazole optionally together with an alkaline compound as a core material in a tablet formulation. The core is then enterically coated. The use of the alkaline material, which can be chosen from such substances as the sodium salt of carbonic acid, are used to form a "micro-pH" around each omeprazole particle to protect the omeprazole which is highly sensitive to acid pH. The powder mixture is then formulated into enteric-coated small beads, pellets, tablets and may be loaded into capsules by conventional pharmaceutical procedures. This formulation of omeprazole does not teach a non-enteric-coated omeprazole dosage form which can be enterally administered to a patient who may be unable and/or unwilling to swallow capsules, tablets or pellets, nor does it teach a convenient form which can be used to make an omeprazole or other proton pump inhibitor solution or suspension.

Several buffered omeprazole oral solutions/suspensions have been disclosed. For example, Pilbrant et al., *Development of an Oral Formulation of Omeprazole*, SCAND. J. GASTROENT. 20(Suppl. 108): 113–120 (1985) teaches a suspension of micronized omeprazole, 60 mg, in 50 ml of water also containing 8 mmoles of sodium bicarbonate. The suspension was administered as follows: After fasting for at least 10 hours, patients were given a solution of 8 mmoles of sodium bicarbonate in 50 ml of water. Five minutes later the patients took the omeprazole suspension and rinsed it down with another 50 ml of sodium bicarbonate solution. Ten (10), 20 and 30 minutes later, a further 50 ml of sodium bicarbonate solution was administered.

Andersson et el., *Pharmacokinetics of Various Single Intravenous and Oral Doses of Omeprazole*, EUR J. CLIN. PHARMACOL. 39:195–197 (1990) discloses 10 mg, 40 mg, and 90 mg of oral omeprazole dissolved in PEG 400, sodium bicarbonate and water. The concentration of omeprazole cannot be determined, as volumes of diluent are not disclosed. Nevertheless, it is apparent from this reference that multiple doses of sodium bicarbonate were administered with and after the omeprazole suspension.

Andersson et al., *Pharmacokinetics and Bioavailability of Omeprazole After Single and Repeated Oral Administration in Healthy Subjects*, BR. J. CLIN. PHARMAC. 29:557–63 (1990) teaches the oral use of 20 mg of omeprazole, which was dissolved in 20 g of PEG 400 (sp. gravity=1.14) and diluted with 50 ml of water containing 8 mmoles of sodium bicarbonate. In order to protect the omeprazole from gastric acid, the buffered solution was given with 48 mmoles of sodium bicarbonate in 300 ml of water.

Regardh et al., *The Pharmacokinetics of Omeprazole in Humans—A Study of Single Intravenous and Oral Doses*, THER. DRUG MON. 12:163–72 (1990) discloses an oral dose of omeprazole at a concentration 0.4 mg/ml after the drug was dissolved in PEG 400, water and sodium bicarbonate (8 mmoles). A solution containing 16 mmoles of sodium bicarbonate in 100 ml of water was concomitantly given with the omeprazole solution. That dose was followed by a solution of 50 ml of 0.16 mol/L sodium bicarbonate that was used for rinsing the vessel. In both the IV and oral experiment, 50 ml of 0.16 mol/L sodium bicarbonate was administered 5 minutes before administration, and 10, 20 and 30 minutes post-dose.

Landahl et al., *Pharmacokinetics Study of Omeprazole in Elderly Healthy Volunteers*, CLIN. PHARMACOKINETICS 23 (6): 469–476 (1992) teaches the use of an oral dose of 40 mg of omeprazole dissolved in PEG 400, sodium bicarbonate and water. This reference does not disclose the final concentrations utilized. Again, this reference teaches the multiple administration of sodium bicarbonate (8 mmol/L and 16 mmol/L) after the omeprazole solution.

Andersson et al., *Pharmacokinetics of [$^{14}C$] Omeprazole in Patients with Liver Cirrhosis*, CLIN. PHARMACOKINETICS 24(1): 71–78 (1993) discloses the oral administration of 40 mg of omeprazole, which was dissolved in PEG 400, water and sodium bicarbonate. This reference does not teach the final concentration of the omeprazole solution administered, although it emphasizes the need for pre, concomitant and post sodium bicarbonate dosing with a total of 48 mmoles to prevent acid degradation of the drug.

Nakagawa, et al., *Lansoprazole: Phase I Study of lansoprazole (AG-1749) Anti-ulcer Agent*, J. CLIN. THERAPEUTICS & MED.(1991) teaches the oral administration of 30 mg of lansoprazole suspended in 100 ml of sodium bicarbonate, which was administered to patients through a nasogastric tube.

All of the buffered omeprazole solutions described in these references were administered orally, and were given to healthy subjects who were able to ingest the oral dose. In all of these studies, omeprazole was suspended in a solution including sodium bicarbonate, as a pH buffer, in order to protect the acid sensitive omeprazole during administration. In all of these studies, repeated administration of sodium bicarbonate both prior to, during, and following omeprazole administration were required in order to prevent acid degradation of the omeprazole given via the oral route of administration. In the above-cited studies, as much as 48 mmoles of sodium bicarbonate in 300 ml of water must be ingested for a single dose of omeprazole to be orally administered.

The buffered omeprazole solutions of the above cited prior art require the ingestion of large amounts of sodium bicarbonate and large volumes of water by repeated administration. This has been considered necessary to prevent acid degradation of the omeprazole. In the above-cited studies, basically healthy volunteers, rather than sick patients, were given dilute buffered omeprazole utilizing pre-dosing and post-dosing with large volumes of sodium bicarbonate.

The administration of large amounts of sodium bicarbonate can produce at least six significant adverse effects, which can dramatically reduce the efficacy of the omeprazole in patients and reduce the overall health of the patients. First, the fluid volumes of these dosing protocols would not be suitable for sick or critically ill patients who must receive multiple doses of omeprazole. The large volumes would result in the distention of the stomach and increase the likelihood of complications in critically ill patients such as the aspiration of gastric contents.

Second, because bicarbonate is usually neutralized in the stomach or is absorbed, such that belching results, patients with gastroesophageal reflux may exacerbate or worsen their reflux disease as the belching can cause upward movement of stomach acid (Brunton, *Agents for the Control of Gastric Acidity and Treatment of Peptic Ulcers*, IN, Goodman AG, et al. *The Pharmacologic Basis of Therapeutics.* (New York, p. 907 (1990)).

Third, patients with conditions such as hypertension or heart failure are standardly advised to avoid the intake of excessive sodium as it can cause aggravation or exacerbation of their hypertensive conditions (Brunton, supra). The ingestion of large amounts of sodium bicarbonate is inconsistent with this advice.

Fourth, patients with numerous conditions that typically accompany critical illness should avoid the intake of excessive sodium bicarbonate as it can cause metabolic alkalosis that can result in a serious worsening of the patient's condition.

Fifth, excessive antacid intake (such as sodium bicarbonate) can result in drug interactions that produce serious adverse effects. For example, by altering gastric and urinary pH, antacids can alter rates of drug dissolution and absorption, bioavailability, and renal elimination (Brunton, supra).

Sixth, because the buffered omeprazole solutions of the prior art require prolonged administration of sodium bicarbonate, it makes it difficult for patients to comply with the regimens of the prior art. For example, Pilbrant et al. disclose an oral omeprazole administration protocol calling for the administration to a subject who has been fasting for at least ten hours, a solution of 8 mmoles of sodium bicarbonate in 50 ml of water. Five minutes later, the subject ingests a suspension of 60 mg of omeprazole in 50 ml of water that also contains 8 mmoles of sodium bicarbonate. This is rinsed down with another 50 ml of 8 mmoles sodium bicarbonate solution. Ten minutes after the ingestion of the omeprazole dose, the subject ingests 50 ml of bicarbonate solution (8 mmoles). This is repeated at twenty minutes and thirty minutes post omeprazole dosing to yield a total of 48 mmoles of sodium bicarbonate and 300 ml of water in total that are ingested by the subject for a single omeprazole dose. Not only does this regimen require the ingestion of excessive amounts of bicarbonate and water, which is likely to be dangerous to some patients, it is unlikely that even healthy patients would comply with this regimen.

It is well documented that patients who are required to follow complex schedules for drug administration are non-compliant and, thus, the efficacy of the buffered omeprazole solutions of the prior art would be expected to be reduced due to non-compliance. Compliance has been found to be markedly reduced when patients are required to deviate from a schedule of one or two (usually morning and night) doses of a medication per day. The use of the prior art buffered omeprazole solutions which require administration protocols with numerous steps, different drugs (sodium bicarbonate+omeprazole+PEG 400 versus sodium bicarbonate alone), and specific time allotments between each stage of the total omeprazole regimen in order to achieve efficacious results is clearly in contrast with both current drug compliance theories and human nature.

The prior art (Pilbrant et al., 1985) teaches that the buffered omeprazole suspension can be stored at refrigerator temperatures for a week and deep frozen for a year while still maintaining 99% of its initial potency. It would be desirable to have an omeprazole or other proton pump inhibitor solution or suspension that could be stored at room temperature or in a refrigerator for periods of time which exceed those of the prior art while still maintaining 99% of the initial potency. Additionally, it would be advantageous to have a form of the omeprazole and bicarbonate which can be utilized to instantly make the omeprazole solution/suspension of the present invention which is supplied in a solid form which imparts the advantages of improved shelf-life at room temperature, lower cost to produce, less expensive shipping costs, and which is less expensive to store.

It would, therefore, be desirable to have a proton pump inhibitor formulation, which provides a cost-effective means for the treatment of the aforementioned conditions without the adverse effect profile of $H_2$ receptor antagonists, antacids, and sucralfate. Further, it would be desirable to have a proton pump inhibitor formulation which is convenient to prepare and administer to patients unable to ingest solid dosage forms such as tablets or capsules, which is rapidly absorbed, and can be orally or enterally delivered as a liquid form or solid form. It is desirable that the liquid formulation not clog indwelling tubes, such as nasogastric tubes or other similar tubes, and which acts as an antacid immediately upon delivery.

It would further be advantageous to have a potentiator or enhancer of the pharmacological activity of the proton pump inhibitors. It has been theorized by applicant that the proton pump inhibitors can only exert their effects on $H^+$, $K^+$-ATPase when the parietal cells are active. Accordingly, applicant has identified, as discussed below, parietal cell activators that are administered to synergistically enhance the activity of the proton pump inhibitors.

Additionally, the intravenous dosage forms of proton pump inhibitors of the prior art are often administered in larger doses than the oral forms. For example, the typical adult IV dose of omeprazole is greater than 100 mg/day whereas the adult oral dose is 20 to 40 mg/day. Large IV doses are necessary to achieve the desired pharmacologic effect because, it is believed, many of the parietal cells are in a resting phase (mostly inactive) during an IV dose given to patients who are not taking oral substances by mouth (npo) and, therefore, there is little active (that which is inserted into the secretory canalicular membrane) $H^+$, $K^+$-ATPase to inhibit. Because of the clear disparity in the amount of drug necessary for IV versus oral doses, it would be very advantageous to have compositions and methods for IV administration where significantly less drug is required.

SUMMARY OF THE INVENTION AND ADVANTAGES

The foregoing advantages and objects are accomplished by the present invention. The present invention provides an oral solution/suspension comprising a proton pump inhibiting agent and at least one buffering agent. The proton pump inhibiting agent can be any substituted benzimidazole compound having $H^+$, $K^+$-ATPase inhibiting activity and being unstable to acid.

The inventive composition can alternatively be formulated as a powder, tablet, suspension tablet, chewable tablet, capsule, two-part tablet or capsule, effervescent powder, effervescent tablet, pellets and granules. Such dosage forms are advantageously devoid of any enteric coating or delayed or sustained-release delivery mechanisms, and comprise a proton pump inhibiting agent and at least one buffering agent to protect the proton pump inhibiting agent against acid degradation. Both the liquid and dry dosage forms can further include anti-foaming agents, parietal cell activators and flavoring agents.

In another embodiment, oral dosage forms are disclosed comprising a combination of enteric-coated or delayed-released proton pump inhibiting agent with an antacid(s). Such forms may optionally comprise a non-enteric-coated proton pump inhibiting agent.

Kits utilizing the inventive dry dosage forms are also disclosed herein to provide for the easy preparation of a liquid composition from the dry forms.

In accordance with the present invention, there is further provided a method of treating gastric acid disorders by orally administering to a patient a pharmaceutical composition(s) and/or dosage form(s) disclosed herein.

Additionally, the present invention relates to a method for enhancing the pharmacological activity of an intravenously administered proton pump inhibiting agent in which at least one parietal cell activator is orally administered to the patient before, during and/or after the intravenous administration of the proton pump inhibiting agent.

Finally, the present invention relates to a method for optimizing the type and amount of buffer desirable for individual proton pump inhibiting agents.

BRIEF DESCRIPTION OF THE DRAWINGS

Other advantages of the present invention will be readily appreciated as the same becomes better understood by reference to the following detailed description when considered in connection with the accompanying drawing wherein.

DETAILED DESCRIPTION OF THE INVENTION

I. Introduction

Figure 1:
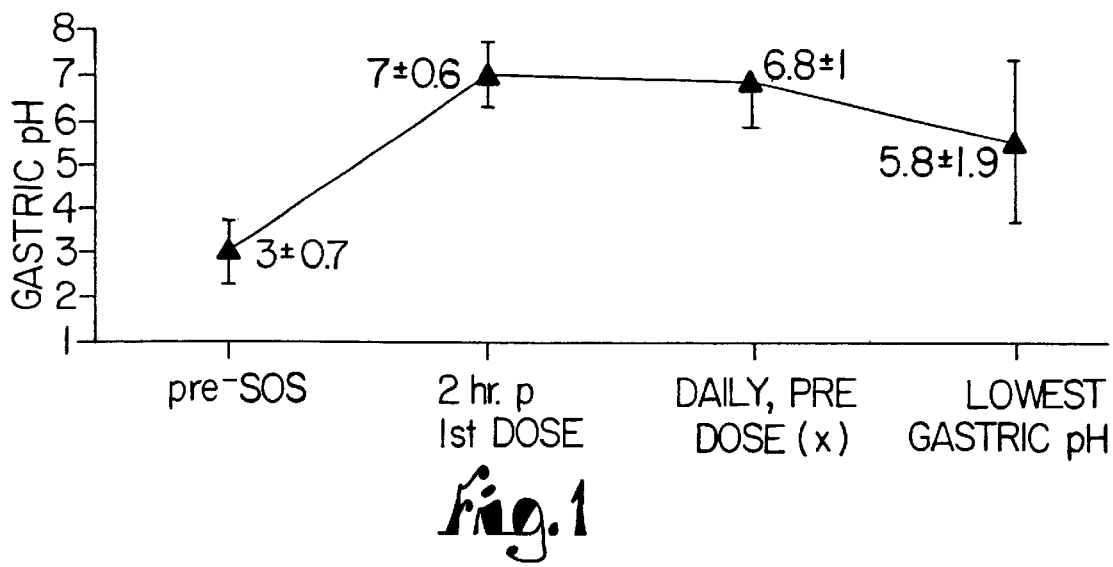
FIG. 1 is a graph showing the effect of the omeprazole solution of the present invention on gastric pH in patients at risk for upper gastrointestinal bleeding from stress-related mucosal damage.

The present invention is directed to methods, kits, combinations, and compositions for treating, preventing or reducing the risk of developing a gastrointestinal disorder or disease, or the symptoms associated with, or related to a gastrointestinal disorder or disease in a subject in need thereof.

While the present invention may be embodied in many different forms, several specific embodiments are discussed herein with the understanding that the present disclosure is to be considered only as an exemplification of the principles of the invention, and it is not intended to limit the invention to the embodiments illustrated. For example, where the present invention is illustrated herein with particular reference to omeprazole, lansoprazole, pantoprazole, rabeprazole, esomeprazole, pariprazole, or leminoprazole, it will be understood that any other proton pump inhibiting agent, if desired, can be substituted in whole or in part for omeprazole, lansoprazole, pantoprazole, rabeprazole, esomeprazole, pariprazole, or leminoprazole in the methods, kits, combinations, and compositions herein described.

The present invention provides a method of increasing absorption of a proton pump inhibiting agent into the blood serum of a subject. The method comprises administering to the subject a solid pharmaceutical composition comprising a proton pump inhibiting agent and a buffering agent for oral administration and ingestion by the subject. Upon administration the composition contacts the gastric fluid of the stomach and thereby increases the absorption of the proton pump inhibiting agent into the blood serum greater than the absorption of the proton pump inhibiting agent in the absence of the buffering agent. The amount of buffering agent present in the composition is sufficient to increase the gastric fluid pH of the stomach to a pH that prevents or inhibits acid degradation of the proton pump inhibiting agent in the gastric fluid of the stomach, and to allow a measurable serum concentration of the proton pump inhibiting agent to be absorbed into the blood serum of the subject. The concentration of the proton pump inhibiting agent can be determined using pharmacokinetic testing procedures known to those skilled in the art.

The present invention also provides for a method of treating a gastrointestinal disorder in a subject in need thereof, by orally administering to the subject a solid pharmaceutical composition comprising a proton pump inhibiting agent and a buffering agent. The buffering agent is in an amount sufficient to increase the pH of the stomach content of the subject to a pH that prevents or inhibits acid degradation of the proton pump inhibiting agent in the stomach and to allow blood serum absorption of the proton pump inhibiting agent greater than the blood serum absorption of the proton pump inhibiting agent in the absence of the buffering agent when the composition is administered orally to the subject. A therapeutically effective amount of proton pump inhibiting agent is thus absorbed into the blood serum of the subject.

The present invention also provides a method of treating an acid related gastrointestinal disorder in a subject in need thereof, by orally administering to the subject a pharmaceutical composition in an oral dosage form for immediate release into an absorption pool of the subject. In one embodiment of the present invention, the absorption pool is highly acidic pH. The composition comprises a proton pump inhibiting agent and a buffering agent. The buffering agent is in an amount sufficient to increase the pH of the absorption pool of the subject to a pH that prevents or inhibits acid degradation of the proton pump inhibiting agent and to allow absorption of the proton pump inhibiting agent from the absorption pool into blood serum of the subject greater than the absorption of the proton pump inhibiting agent in the absence of the buffering agent when the composition is administered orally to the subject. The amount of proton pump inhibiting agent is sufficient to achieve a measurable serum concentration of the proton pump inhibiting agent in the blood serum of the subject after oral administration of the composition.

The present invention also provides a method of making a pharmaceutical composition for oral administration to a subject and for immediate release of a proton pump inhibiting agent and a buffering agent into an absorption pool of the subject. In one embodiment of the present invention the absorption pool is highly acidic pH. The method comprises admixing the proton pump inhibiting agent and the buffering agent. The buffering agent is in an amount sufficient to increase the pH of the absorption pool of the subject to a pH that prevents or inhibits acid degradation of the proton pump inhibiting agent in the absorption pool and to allow absorption of the proton pump inhibiting agent from the absorption pool into blood serum of the subject greater than the absorption of the proton pump inhibiting agent in the absence of the buffering agent when the composition is administered orally to the subject. The amount of the proton pump inhibiting agent is sufficient to achieve a measurable serum concentration in the blood serum of the subject after oral administration of the composition.

In one embodiment of the present invention, the composition is administered in an amount to achieve a measurable serum concentration of the proton pump inhibiting agent greater than about 0.1 µg/ml within about 15 minutes after administration of the composition.

In another embodiment of the present invention, the composition is administered to the subject in an amount to achieve a measurable serum concentration of the proton pump inhibiting agent greater than about 0.1 µg/ml from about 15 minutes to about 6 hours after administration of the composition.

In yet another embodiment of the present invention, the composition is administered to the subject in an amount to achieve a measurable serum concentration of the proton pump inhibiting agent greater than about 0.15 µg/ml from about 15 minutes to about 1.5 hours after administration of the composition.

In still another embodiment of the present invention, the composition is administered to the subject in an amount to achieve a measurable serum concentration of the proton pump inhibiting agent greater than about 0.2 µg/ml within about 15 minutes after administration of the composition.

Besides being useful for human treatment, the present invention is also useful for veterinary treatment of companion mammals, exotic animals and farm animals, including mammals, rodents, and the like. In one embodiment, the mammal includes a horse, dog, or cat.

For the purposes of this application, the term "proton pump inhibitor," or "PPI," or "proton pump inhibiting agent" means any agent possessing pharmacological activity as an inhibitor of $H^+$, $K^+$-ATPase. A class of proton pump inhibiting agents useful in the methods, kits, combinations, and compositions of the present invention includes substituted benzimidazole compounds possessing such pharmacological activity as an inhibitor of $H^+$, $K^+$-ATPase. In one embodiment of the present invention, the proton pump inhibiting agent is acid sensitive. In another aspect of the invention, the substituted benzimidazole compound employed in the methods, kits, combinations, and compositions can include, for example, omeprazole, lansoprazole, pantoprazole, rabeprazole, esomeprazole, pariprazole, or leminoprazole. The definition of "PPI," or "proton pump inhibitor," or "proton pump inhibiting agent" as used herein can also mean that the agent possessing pharmacological activity as an inhibitor of $H^+$, $K^+$-ATPase may, if desired, be in the form of a salt, ester, amide, enantiomer, isomer, tautomer, prodrug, derivative or the like, provided the salt, ester, amide, enantiomer, isomer, tautomer, prodrug, or derivative is suitable pharmacologically, that is, effective in the present methods, combinations, kits, and compositions. Substituted benzimidazole compounds and the salts, esters, amides, enantiomers, isomers, tautomers, prodrugs and derivatives thereof may be prepared using standard procedures known to those skilled in the art of synthetic organic chemistry and described, for example, by J. March, *Advanced Organic Chemistry; Reactions, Mechanisms and Structure*, 4th Ed. (New York: Wiley-Interscience, 1992).

As explained further herein, the proton pump inhibiting agents generally inhibit ATPase in the same way. Differences in onset and relative potencies are largely due to differences in the acid instability of the parent compounds.

In one embodiment, the therapeutic agents of the present invention can be formulated as a single pharmaceutical composition or as independent multiple pharmaceutical dosage forms. Pharmaceutical compositions according to the present invention include those suitable for oral, rectal, buccal (for example, sublingual), or parenteral (for example, intravenous) administration, although the most suitable route in any given case will depend on the nature and severity of the condition being treated and on the nature of the particular compound which is being used. Such dosage forms include, but are not limited to, a tablet, a powder, a suspension tablet, a chewable tablet, a capsule, an effervescent powder, an effervescent tablet, a pellet, or a granule.

In one embodiment of the present invention, the compositions comprise a dry formulation, or a solution and/or a suspension of the proton pump inhibiting agent. As used herein, the terms "suspension" and "solution" are interchangeable with each other and generally mean a solution and/or suspension of the substituted benzimidazole in an aqueous medium. Such dry formulations, solutions and/or suspensions may also include, for example, a suspending agent (for example, gums, xanthans, cellulosics and sugars), a humectant (for example, sorbitol), a solubilizer (for example, ethanol, water, PEG and propylene glycol), a surfactant (for example, sodium lauryl sulfate, Spans, Tweens, and cetyl pyridine), a preservative, an antioxidant (for example, parabens, and vitamins E and C), an anti-caking agent, a coating agent, a chelating agent (for example, EDTA), a stabalizer, an antimicrobial agent, an antifungal or antibacterial agent (for example, parabens, chlorobutanol, phenol, sorbic acid), an isotonic agent (for example, sugar, sodium chloride), a thickening agent (for example, methyl cellulose), a flavoring agent (for example, chocolate, thalmantin, aspartame, root beer or watermelon or other flavorings stable at pH 7 to 9), an anti-foaming agent (e.g., simethicone, Mylicon®), a disintegrant, a flow aid, a lubricant, an adjuvant, an excipient, a colorant, a diluent, a moistening agent, a preservative, a pharmaceutically compatible carrier, or a parietal cell activator.

In one embodiment, the present invention relates to a pharmaceutical composition comprising a proton pump inhibiting agent, a buffering agent, and optionally a parietal cell activator. The proton pump inhibitor of the present invention may or may not be enteric coated, or sustained or delayed-release depending on the context in which the proton pump inhibiting agent in utilized. In one embodiment of the present invention the proton pump inhibiting agent is not enteric coated, or sustained or delayed-release. In yet another embodiment the proton pump inhibitor is enteric coated, or sustained or delayed-release. And in another embodiment the composition may contain both an enteric coated proton pump inhibiting agent and a non-enteric coated proton pump inhibiting agent. Such a composition is contemplated where both an immediate release of the proton pump inhibiting agent into the absorption pool is desired as well as a delayed release of the proton pump inhibiting agent is desired providing an extended therapeutic effect.

In still another example, a pharmaceutical formulation is prepared by mixing enteric coated granules of a proton pump inhibiting agent with one or more buffering agents (e.g., omeprazole 20 mg granules plus 500 mg sodium bicarbonate and 500 mg calcium carbonate) in a solid dosage form. Upon oral administration, the buffering agents elevate the gastric pH such that all or part of the enteric coating is dissolved in the gastric fluid (rather than, for example, in the higher pH environment of the duodenum), and the omeprazole is available for immediate release in the gastric fluid for absorption into the bloodstream. Many variations in this type of formulation (i.e., higher or lower amounts of inhibiting agent and/or buffering agent) may be utilized in the present invention.

After administration to the subject and absorption of the proton pump inhibiting agent (or administration intravenously), the agent is delivered via the blood serum to various tissues and cells of the body including the parietal cells. Not intending to be bound by any one theory, research suggests that when the proton pump inhibiting agent is in the form of a weak base and is non-ionized, it freely passes through physiologic membranes, including the cellular membranes of the parietal cell. It is believed that the non-ionized proton pump inhibiting agent moves into the acid-secreting portion of the parietal cell, the secretory canaliculus. Once in the acidic milieu of the secretory canaliculus, the proton pump inhibiting agent is apparently protonated (ionized) and converted to the active form of the drug. Generally, ionized proton pump inhibiting agents are membrane impermeable and form disulfide covalent bonds with cysteine residues in the alpha subunit of the proton pump. Such active forms are included within the definition of "PPI," "proton pump inhibitor," or "proton pump inhibiting agent" herein.

The proton pump inhibiting agent is administered and dosed in accordance with good medical practice, taking into account the clinical condition of the individual patient, the site and method of administration, scheduling of administration, and other factors known to medical practitioners.

For the purposes of this application, the term "buffering agent" or "buffer" means any pharmaceutically appropriate weak base or strong base (and mixtures thereof) that, when formulated or delivered with (e.g., before, during and/or after) the proton pump inhibiting agent, functions to substantially prevent or inhibit the acid degradation of the proton pump inhibiting agent by gastric acid sufficient to preserve the bioavailability of the proton pump inhibiting agent administered. A buffering agent useful in the methods, kits, combinations, and compositions of the present invention include a bicarbonate salt of Group IA metal, such as, for example, magnesium hydroxide, magnesium lactate, magnesium gluconate, magnesium oxide, magnesium carbonate, or magnesium silicate. Other buffering agents include, but are not limited to, potassium bicarbonate, magnesium hydroxide, magnesium lactate, magnesium gluconate, other magnesium salts, aluminum hydroxide, aluminum hydroxide/sodium bicarbonate coprecipitate, a mixture of an amino acid and a buffer, a mixture of aluminum glycinate and a buffer, a mixture of an acid salt of an amino acid and a buffer, and a mixture of an alkali salt of an amino acid and a buffer. Other buffering agents that may be used in the methods, kits, combinations, and compositions of the present invention include, but are not limited to, sodium citrate, sodium tartarate, sodium acetate, sodium carbonate, sodium polyphosphate, potassium polyphosphate, sodium pyrophosphate, potassium pyrophosphate, disodium hydrogenphosphate, dipotassium hydrogenphosphate, trisodium phosphate, tripotassium phosphate, sodium acetate, potassium metaphosphate, magnesium oxide, magnesium hydroxide, magnesium carbonate, magnesium silicate, calcium acetate, calcium glycerophosphate, calcium cholride, calcium hydroxide, calcium lactate, calcium carbonate, calcium bicarbonate, and other calcium salts. Mixtures of any of the foregoing can also be used in the methods, kits, combinations, and compositions of the present invention.

The buffering agent is administered in an amount sufficient to substantially prevent or inhibit the acid degradation of the proton pump inhibiting agent by gastric acid sufficient to preserve the bioavailability of the proton pump inhibiting agent administered, and preserve the ability of the proton pump inhibiting agent to elicit a therapeutic effect. Therefore, the buffering agent of the present invention, when in the presence of the biological fluids of the stomach, must only elevate the pH of these biological fluids sufficiently to achieve adequate bioavailability of the drug to effect therapeutic action.

In one embodiment, the buffering agent is present in the methods, kits, combinations, and compositions of the present invention in an amount of about 0.05 mEq to about 5.0 mEq per mg of proton pump inhibiting agent. In another embodiment of the present invention the buffering agent is present in an amount of about 0.1 mEq to about 2.5 mEq per mg of proton pump inhibiting agent. In yet another embodiment of the present invention the buffering agent is present in an amount of at least 10 mEq. In yet another embodiment of the present invention the buffering agent is present in an amount of about 10 mEq to about 70 mEq. In still another embodiment, the buffering agent is present in an amount of about 20 mEq to about 40 mEq. And in yet another embodiment of the present invention, the amount of the buffering agent is present in an amount more than about 20 times the amount of the proton pump inhibiting agent on a weight to weight basis in the composition.

In one embodiment of the present invention, the buffering agent is sodium bicarbonate and is present in the methods, kits, combinations and compositions in an amount of at least 250 mg. In another embodiment, the sodium bicarbonate is present in an amount of at least 800 mg. In yet another embodiment, the sodium bicarbonate is present in an amount from about 250 mg to about 4000 mg. And in still another embodiment, the sodium bicarbonate is present in an amount from about 1000 mg to about 1680 mg.

In one embodiment of the present invention, the buffering agent is calcium carbonate and is present in the methods, kits, combinations and compositions in an amount of at least 250 mg. In another embodiment, the calcium carbonate is present in an amount of at least 800 mg. In yet another embodiment, the calcium carbonate is present in an amount from about 250 mg to about 4000 mg. And in still another embodiment, the calcium carbonate is present in an amount from about 500 mg to about 1000 mg.

The term "effective amount" means, consistent with considerations known in the art, the amount of proton pump inhibiting agent or other agent effective to elicit a pharmacologic effect or therapeutic effect (including, but not limited to, raising of gastric pH, reducing gastrointestinal bleeding, reducing in the need for blood transfusion, improving survival rate, more rapid recovery, parietal cell activation and $H^+$, $K^+$-ATPase inhibition or improvement or elimination of symptoms, and other indicators as are selected as appropriate measures by those skilled in the art), without undue adverse side effects.

The term "measurable serum concentration" means the serum concentration (typically measured in mg, $\mu$g, or ng of therapeutic agent per ml, dl, or 1 of blood serum) of a therapeutic agent absorbed into the bloodstream after administration. Illustratively, the serum concentration of a proton pump inhibiting agent of the present invention that corresponds to a measurable serum concentration for an adult subject is greater than about 5 ng/ml. In another embodiment of the present invention, the serum concentration of the proton pump inhibiting agent that corresponds to a measurable serum concentration for an adult human is less than about 10.0 $\mu$g/ml. In yet another embodiment of the present invention, the serum concentration of the proton pump inhibiting agent that corresponds to a measurable serum concentration for an adult human is from about 0.01 μg/ml to about 5 μg/ml. And in still another embodiment of the present invention, the serum concentration of the proton pump inhibiting agent that corresponds to a measurable serum concentration for an adult human is from about 0.25 μg/ml to about 2.5 μg/ml.

In one embodiment of the present invention, the composition is administered to a subject in a therapeutically-effective amount, that is, the composition is administered in an amount that achieves a therapeutically-effective dose of a proton pump inhibiting agent in the blood serum of a subject for a period of time to elicit a desired therapeutic effect. Illustratively, in a fasting adult human (fasting for generally at least 10 hours) the composition is administered to achieve a therapeutically-effective dose of a proton pump inhibiting agent in the blood serum of a subject from about 5 minutes after administration of the composition. In another embodiment of the present invention, a therapeutically-effective dose of the proton pump inhibiting agent is achieved in the blood serum of a subject at about 10 minutes from the time of administration of the composition to the subject. In another embodiment of the present invention, a therapeutically-effective dose of the proton pump inhibiting agent is achieved in the blood serum of a subject at about 20 minutes from the time of administration of the composition to the subject. In yet another embodiment of the present invention, a therapeutically-effective dose of the proton pump inhibiting agent is achieved in the blood serum of a subject at about 30 minutes from the time of administration of the composition to the subject. In still another embodiment of the present invention, a therapeutically-effective dose of the proton pump inhibiting agent is achieved in the blood serum of a subject at about 40 minutes from the time of administration of the composition to the subject. In one embodiment of the present invention, a therapeutically-effective dose of the proton pump inhibiting agent is achieved in the blood serum of a subject at about 20 minutes to about 12 hours from the time of administration of the composition to the subject. In another embodiment of the present invention, a therapeutically-effective dose of the proton pump inhibiting agent is achieved in the blood serum of a subject at about 20 minutes to about 6 hours from the time of administration of the composition to the subject. In yet another embodiment of the present invention, a therapeutically-effective dose of the proton pump inhibiting agent is achieved in the blood serum of a subject at about 20 minutes to about 2 hours from the time of administration of the composition to the subject. In still another embodiment of the present invention, a therapeutically-effective dose of the proton pump inhibiting agent is achieved in the blood serum of a subject at about 40 minutes to about 2 hours from the time of administration of the composition to the subject. And in yet another embodiment of the present invention, a therapeutically-effective dose of the proton pump inhibiting agent is achieved in the blood serum of a subject at about 40 minutes to about 1 hour from the time of administration of the composition to the subject.

In general, a composition of the present invention is administered at a dose suitable to provide an average blood serum concentration of a proton pump inhibiting agent of at least about 1.0 μg/ml in a subject over a period of about 1 hour after administration. Contemplated compositions of the present invention provide a therapeutic effect as proton pump inhibiting agent medications over an interval of about 5 minutes to about 24 hours after administration, enabling once-a-day or twice-a-day administration if desired. In one embodiment of the present invention, the composition is administered at a dose suitable to provide an average blood serum concentration of a proton pump inhibiting agent of at least about 1.0 μg/ml in a subject about 10, 20, 30, or 40 minutes after administration of the composition to the subject.

The amount of therapeutic agent necessary to elicit a therapeutic effect can be experimentally determined based on, for example, the absorption rate of the agent into the blood serum, the bioavailability of the agent, and the amount of protein binding of the agent. It is understood, however, that specific dose levels of the therapeutic agents of the present invention for any particular patient depends upon a variety of factors including the activity of the specific compound employed, the age, body weight, general health, sex, and diet of the subject (including, for example, whether the subject is in a fasting or fed state), the time of A administration, the rate of excretion, the drug combination, and the severity of the particular disorder being treated and form of administration. Treatment dosages generally may be titrated to optimize safety and efficacy. Typically, dosage-effect relationships from in vitro and/or in vivo tests initially can provide useful guidance on the proper doses for subject administration. Studies in animal models generally may be used for guidance regarding effective dosages for treatment of gastrointestinal disorders or diseases in accordance with the present invention. In terms of treatment protocols, it should be appreciated that the dosage to be administered will depend on several factors, including the particular agent that is administered, the route administered, the condition of the particular subject, etc. Generally speaking, one will desire to administer an amount of the compound that is effective to achieve a serum level commensurate with the concentrations found to be effective in vitro for a period of time effective to elicit a therapeutic effect. Thus, where a compound is found to demonstrate in vitro activity at, for example, 10 ng/ml, one will desire to administer an amount of the drug that is effective to provide at least about a 10 ng/ml concentration in vivo for a period of time that elicits a desired therapeutic effect, for example, raising of gastric pH, reducing gastrointestinal bleeding, reducing the need for blood transfusion, improving survival rate, more rapid recovery, parietal cell activation and $H^+$, $K^+$-ATPase inhibition or improvement or elimination of symptoms, and other indicators as are selected as appropriate measures by those skilled in the art. Determination of these parameters is well within the skill of the art. These considerations are well known in the art and are described in standard textbooks.

In order to measure and determine the gastrointestinal disorder- or disease-effective amount of a proton pump inhibiting agent to be delivered to a subject, serum proton pump inhibiting agent concentrations can be measured using standard assay techniques.

"Therapeutic window" refers to the range of plasma concentrations, or the range of levels of therapeutically active substance at the site of action, with a high probability of eliciting a therapeutic effect.

It will be understood that a therapeutically effective amount of a proton pump inhibiting agent and/or a buffering agent that is administered to a subject is dependent inter alia on the body weight of the subject. Illustratively, where the agent is a substituted benzimidazole such as, for example, omeprazole, lansoprazole, pantoprazole, rabeprazole, esomeprazole, pariprazole, or leminoprazole, and the subject is a child or a small animal (e.g., a dog), for example, a relatively low amount of the agent in the dose range of about 1 mg to about 20 mg is likely to provide blood serum concentrations consistent with therapeutic effectiveness. Where the subject is an adult human or a large animal (e.g., a horse), achievement of such blood serum concentrations of the agent are likely to require dose units containing a relatively greater amount of the agent. For example, in an adult human the methods, kits, combinations, and compositions of the present invention comprise a proton pump inhibiting agent, for example, omeprazole, lansoprazole, pantoprazole, rabeprazole, esomeprazole, pariprazole, or leminoprazole, in a dosage amount of about 5 mg to about 1000 mg, or of about 7.5 mg to about 300 mg, or of about 10 mg to about 100 mg, or of about 15 mg to about 80 mg.

The solid compositions of the present invention are generally in the form of discrete unit dose articles, such as in a tablet, powder, suspension tablet, chewable tablet, capsule, effervescent powder, effervescent tablet, pellet, or granule. Such unit dose articles typically contain about 1 mg to about 1000 mg of the proton pump inhibiting agent, or about 5 mg to about 300 mg, or about 10 mg to about 100 mg, or about 15 mg to about 80 mg. Illustratively, these unit dose articles may contain a 5 mg, 10 mg, 15 mg, 20 mg, 25 mg, 30 mg, 40 mg, 50 mg, 60 mg, 75 mg, 80 mg, or 100 mg dose of a proton pump inhibiting agent. In one embodiment, the buffering agent is present in compositions of the present invention in an amount of about 0.05 mEq to about 5.0 mEq per mg of proton pump inhibiting agent, or about 0.1 mEq to about 2.5 mEq per mg of proton pump inhibiting agent, or about 0.5 mEq to about 1.0 mEq per mg of proton pump inhibiting agent. Such dosage units may be given at least once or twice a day, or as many times as needed to elicit a therapeutic response. A particular unit dosage form can be selected to accommodate the desired frequency of administration used to achieve a specified daily dosage.

A pharmaceutical formulation of the proton pump inhibiting agents utilized in the present invention can be administered orally or enterally to the subject. This can be accomplished, for example, by administering the solution via a nasogastric (ng) tube or other indwelling tubes placed in the GI tract. In one embodiment of the present invention, in order to avoid the critical disadvantages associated with administering large amounts of sodium bicarbonate, the proton pump inhibiting agent solution of the present invention is administered in a single dose which does not require any further administration of bicarbonate, or other buffer following the administration of the proton pump inhibiting agent solution, nor does it require a large amount of bicarbonate or buffer in total. That is, unlike the prior art proton pump inhibiting agent solutions and administration protocols outlined above, the formulation of the present invention is given in a single dose, which does not require administration of bicarbonate either before or after administration of the proton pump inhibiting agent. The present invention eliminates the need to pre-or post-dose with additional volumes of water and sodium bicarbonate. The amount of bicarbonate administered via the single dose administration of the present invention is less than the amount of bicarbonate administered as taught in the prior art references cited above.

The term "immediate release" is intended to refer to any proton pump inhibiting agent containing formulation in which release of the proton pump inhibiting agent is immediate, i.e., with an "immediate release" formulation, oral administration results in immediate release of the proton pump inhibiting agent into an absorption pool. See also, Remington: The Science and Practice of Pharmacy, Nineteenth Ed. (Easton, Pa.: Mack Publishing Company, 1995).

As discussed herein, immediate and nonimmediate release (or controlled release) can be defined kinetically by reference to the following equation:

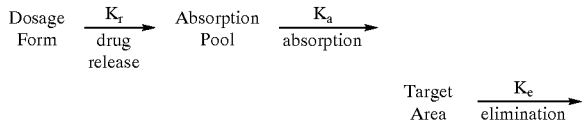

The absorption pool represents a solution of the drug administered at a particular absorption site, and $K_r$, $K_a$, and $K_e$ are first-order rate constants for (1) release of the drug from the formulation, (2) absorption, and (3) elimination, respectively. For immediate release dosage forms, the rate constant for drug release $K_r$, is generally equal to or greater than the absorption rate constant $K_a$. For controlled release formulations, the opposite is generally true, i.e., $K_r <<K_a$, such that the rate of release of drug from the dosage form is the rate-limiting step in the delivery of the drug to the target area. The term "controlled release" includes any nonimmediate release formulation, including but not limited to enteric coated formulations and sustained release, delayed release and pulsatile release formulations. The term "sustained release" is used in its conventional sense to refer to a drug formulation that provides for gradual release of a drug over an extended period of time, and, may sometimes, although not necessarily, result in substantially constant blood levels of a drug over an extended time period.

"Plasma concentration" refers to the concentration of a substance in blood plasma or blood serum.

"Drug absorption" or "absorption" refers to the process of movement from the site of administration of a drug toward the systemic circulation.

"Bioavailability" refers to the extent to which an active moiety (drug or metabolite) is absorbed into the general circulation and becomes available at the site of drug action in the body.

"Drug elimination" or "elimination" refers to the sum of the processes of drug loss from the body.

"Metabolism" refers to the process of chemical alteration of drugs in the body.

"Pharmacodynamics" refers to the factors which determine the biologic response observed relative to the concentration of drug at a site of action.

"Pharmacokinetics" refers to the factors which determine the attainment and maintenance of the appropriate concentration of drug at a site of action.

"Half-life" refers to the time required for the plasma drug concentration or the amount in the body to decrease by 50% from its maximum concentration.

The use of the term "highly acidic pH" in the present disclosure means a pH in the range of about 1 to 4. The use of the term "less acidic to basic pH" in the present disclosure means a pH greater than about 4 up to approximately about 8.0.

The use of the term "about" in the present disclosure means "approximately," and illustratively, the use of the term "about" indicates that dosages slightly outside the cited ranges may also be effective and safe, and such dosages are also encompassed by the scope of the present claims.

The phrase "pharmaceutically acceptable" is used adjectivally herein to mean that the modified noun is appropriate for use in a pharmaceutical product. Pharmaceutically acceptable cations include metallic ions and organic ions. More preferred metallic ions include, but are not limited to, appropriate alkali metal salts, alkaline earth metal salts and other physiological acceptable metal ions. Exemplary ions include aluminum, calcium, lithium, magnesium, potassium, sodium and zinc in their usual valences. Preferred organic ions include protonated tertiary amines and quaternary ammonium cations, including in part, trimethylamine, diethylamine, N,N'-dibenzylethylenediamine, chloroprocaine, choline, diethanolamine, ethylenediamine, meglumine (N-methylglucamine) and procaine. Exemplary pharmaceutically acceptable acids include without limitation hydrochloric acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid oxalacetic acid, fumaric acid, propionic acid, aspartic acid, glutamic acid, benzoic acid, and the like.

The phrase "gastrointestinal disorder" or "gastrointestinal disease" refers generally to a disorder or disease that occurs in a mammal due an imbalance between acid and pepsin production, called aggressive factors, and mucous, bicarbonate, and prostaglandin production, called defensive factors. In mammals, such disorders or diseases include, but are not limited to, duodenal ulcer, gastric ulcer, acid dyspepsia, gastroesophageal reflux disease (GERD), severe erosive esophagitis, poorly responsive symptomatic gastroesophageal reflux disease, heartburn, other esophageal disorders, and a gastrointestinal pathological hypersecretory condition such as Zollinger Ellison Syndrome. Treatment of these conditions is accomplished by administering to a subject a therapeutically effective amount of a pharmaceutical composition according to the present invention.

The term "treat" or "treatment" as used herein refers to any treatment of a disorder or disease associated with gastrointestinal disorder, and includes, but is not limited to, preventing the disorder or disease from occurring in a mammal which may be predisposed to the disorder or disease, but has not yet been diagnosed as having the disorder or disease; inhibiting the disorder or disease, for example, arresting the development of the disorder or disease; relieving the disorder or disease, for example, causing regression of the disorder or disease; or relieving the condition caused by the disease or disorder, for example, stopping the symptoms of the disease or disorder.

The term "prevent" or "prevention," in relation to a gastrointestinal disorder or disease, means no gastrointestinal disorder or disease development if none had occurred, or no further gastrointestinal disorder or disease development if there had already been development of the gastrointestinal disorder or disease.

The present invention also relates to administration kits to ease mixing and administration. Illustratively, a month's supply of powder or tablets, for example, can be packaged with a separate month's supply of diluent, and a re-usable plastic dosing cup. More specifically, the package could contain thirty (30) suspension tablets containing 20 mg omeprazole each, 1 L sodium bicarbonate 8.4% solution, and a 30 ml dose cup. The user places the tablet in the empty dose cup, fills it to the 30 ml mark with the sodium bicarbonate, waits for it to dissolve (gentle stirring or agitation may be used), and then ingests the suspension. One skilled in the art will appreciate that such kits may contain many different variations of the above components. For example, if the tablets or powder are compounded to contain proton pump inhibiting agent and buffering agent, the diluent may be water, sodium bicarbonate, or other compatible diluent, and the dose cup can be larger or smaller than 30 ml in size. Also, such kits can be packaged in unit dose form, or as weekly, monthly, or yearly kits, etc.

In human therapy, it is important to provide a dosage form that delivers the required therapeutic amount of the drug in vivo, and renders the drug bioavailable in a rapid manner. The formulations of the present invention satisfy these needs.

II. Preparation of Oral Liquids

As described in Phillips U.S. Pat. No. 5,840,737, the liquid oral pharmaceutical composition of the present invention is prepared by mixing omeprazole enteric-coated granules (Prilosec® AstraZeneca), or omeprazole base, or other proton pump inhibitor or derivatives thereof with a solution including at least one buffering agent (with or without a parietal cell activator, as discussed below). In one embodiment, omeprazole or other proton pump inhibitor, which can be obtained from powder, capsules, and tablets or obtained from the solution for parenteral administration, is mixed with a sodium bicarbonate solution to achieve a desired final omeprazole (or other proton pump inhibitor) concentration. As an example, the concentration of omeprazole in the solution can range from approximately 0.4 mg/ml to approximately 10.0 mg/ml. The preferred concentration for the omeprazole in the solution ranges from approximately 1.0 mg/ml to approximately 4.0 mg/ml, with 2.0 mg/ml being the standard concentration. For lansoprazole (Prevacid® TAP Pharmaceuticals, Inc.) the concentration can range from about 0.3 mg/ml to 10 mg/ml with the preferred concentration being about 3 mg/ml.

The pharmaceutically acceptable carrier of the oral liquid may comprise a bicarbonate salt of Group IA metal as buffering agent, and can be prepared by mixing the bicarbonate salt of the Group IA metal, preferably sodium bicarbonate, with water. The concentration of the bicarbonate salt of the Group IA metal in the composition generally ranges from approximately 5.0 percent to approximately 60.0 percent. In one embodiment, the content of the bicarbonate salt of the Group IA metal ranges from about 3 mEq to about 45 mEq per oral dose.

In another embodiment, the amount of sodium bicarbonate 8.4% used in the solution of the present invention is approximately 1 mEq (or mmole) sodium bicarbonate per 2 mg omeprazole, with a range of approximately 0.2 mEq (mmole) to 5 mEq (mmole) per 2 mg of omeprazole.

In an embodiment of the present invention, enterically-coated omeprazole particles are obtained from delayed release capsules (Prilosec® AstraZeneca). Alternatively, omeprazole base powder can be used. The enterically coated omeprazole particles are mixed with a sodium bicarbonate (NaHCO$_3$) solution (8.4%), which dissolves the enteric coating and forms an omeprazole solution.

The inventive solutions and other dosage forms of the present invention have pharmacokinetic advantages over standard enteric-coated and time-released proton pump inhibitor dosage forms, including: (a) more rapid drug absorbance time (about 10 to 60 minutes) following administration for the proton pump inhibitor solution or dry form versus about 1 to 3 hours following administration for the enteric-coated pellets; (b) the buffer solution protects the proton pump inhibitor from acid degradation prior to absorption; (c) the buffer acts as an antacid while the proton pump inhibitor is being absorbed for rapid antacid relief; and (d) the solutions can be administered through an existing indwelling tube without clogging, for example, nasogastric or other feeding tubes jejunal or duodenal), including small bore needle catheter feeding tubes.

Solutions, suspensions and powders for reconstitutable delivery systems include vehicles such as suspending agents (for example, gums, xanthans, celluloses and sugars), humectants (for example, sorbitol), solubilizers (for example, ethanol, water, PEG and propylene glycol), surfactants (for example, sodium lauryl sulfate, Spans, Tweens, and cetyl pyridine), preservatives and antioxidants (for example, parabens, vitamins E and C, and ascorbic acid), anti-caking agents, coating agents, and chelating agents (for example, EDTA).

Additionally, various additives can be incorporated into the inventive solution to enhance its stability, sterility and isotonicity. Antimicrobial preservatives, such as ambicin, antioxidants, chelating agents, and additional buffers can be added. However, microbiological evidence shows that this formulation inherently possesses antimicrobial and antifungal activity. Various antibacterial and antifungal agents such as, for example, parabens, chlorobutanol, phenol, sorbic acid, and the like can enhance prevention of the action of microorganisms.

In many cases, it would be desirable to include isotonic agents, for example, sugars, sodium chloride, and the like. Additionally, thickening agents such as methyl cellulose are desirable to use in order to reduce the settling of the omeprazole or other proton pump inhibitor or derivatives thereof from the suspension.

The liquid oral solution may further comprise flavoring agents (e.g., chocolate, thalmantin, aspartame, root beer or watermelon) or other flavorings stable at pH 7 to 9, anti-foaming agents (e.g., simethicone 80 mg, Mylicon®) and parietal cell activators (discussed below).

The present invention further includes a pharmaceutical composition comprising omeprazole or other proton pump inhibitor and derivatives thereof and at least one buffering agent in a form convenient for storage, whereby when the composition is placed into an aqueous solution, the composition dissolves and/or disperses yielding a suspension suitable for enteral administration to a subject. The pharmaceutical composition is in a solid form prior to dissolution or suspension in an aqueous solution. The omeprazole or other proton pump inhibiting agents and buffering agent can be formed into a tablet, capsule, pellets or granules, by methods well known to those skilled in the art.

The resultant omeprazole solution is stable at room temperature for several weeks and inhibits the growth of bacteria or fungi as shown in Example X below. Indeed, as established in Example XIII, the solution maintains greater than 90% of its potency for 12 months. By providing a pharmaceutical composition including omeprazole or other proton pump inhibitor with buffer in a solid form, which can be later dissolved or suspended in a prescribed amount of aqueous solution to yield the desired concentration of omeprazole and buffer, the cost of production, shipping, and storage are greatly reduced as no liquids are shipped (reducing weight and cost), and there is no need to refrigerate the solid form of the composition or the solution. Once mixed the resultant solution can then be used to provide dosages for a single subject over a course of time, or for several subjects.

III. Tablets and Other Solid Dosage Forms

As mentioned above, and as described in part in Phillips U.S. Pat. No. 5,840,737, the formulations of the present invention can also be manufactured in concentrated forms, such as powders, capsules, tablets, suspension tablets and effervescent tablets or powders, which can be swallowed whole or first dissolved such that upon reaction with water, gastric secretions or other diluent, the aqueous form of the present invention is produced.

The present pharmaceutical tablets or other solid dosage forms disintegrate rapidly in aqueous media and form an aqueous solution of the proton pump inhibitor and buffering agent with minimal shaking or agitation. Such tablets utilize commonly available materials and achieve these and other desirable objectives. The tablets or other solid dosage forms of this invention provide for precise dosing of a proton pump inhibitor that may be of low solubility in water. They may be particularly useful for medicating children and the elderly and others in a way that is much more acceptable than swallowing or chewing a tablet. The tablets that are produced have low friability, making them easily transportable.

The term "suspension tablets" as used herein refers to compressed tablets which rapidly disintegrate after they are placed in water, and are readily dispersible to form a suspension containing a precise dosage of the proton pump inhibitor. The suspension tablets of this invention comprise, in combination, a therapeutic amount of a proton pump inhibitor, a buffering agent, and a disintegrant. More particularly, the suspension tablets comprise about 20 mg omeprazole and about 4–30 mEq of sodium bicarbonate.

Croscarmellose sodium is a known disintegrant for tablet formulations, and is available from FMC Corporation, Philadelphia, Pa. under the trademark Ac-Di-Sol®. It is frequently blended in compressed tableting formulations either alone or in combination with microcrystalline cellulose to achieve rapid disintegration of the tablet.

Microcrystalline cellulose, alone or co processed with other ingredients, is also a common additive for compressed tablets and is well known for its ability to improve compressibility of difficult to compress tablet materials. It is commercially available under the Avicel® trademark. Two different Avicel® products are utilized, Avicel® PH which is microcrystalline cellulose, and Avicel® AC-815, a co processed spray dried residue of microcrystalline cellulose and a calcium-sodium alginate complex in which the calcium to sodium ratio is in the range of about 0.40:1 to about 2.5:1. While AC-815 is comprised of 85% microcrystalline cellulose (MCC) and 15% of a calcium-sodium alginate complex, for purposes of the present invention this ratio may be varied from about 75% MCC to 25% alginate up to about 95% MCC to 5% alginate. Depending on the particular formulation and active ingredient, these two components may be present in approximately equal amounts or in unequal amounts, and either may comprise from about 10% to about 50% by weight of the tablet.

The suspension tablet composition may, in addition to the ingredients described above, contain other ingredients often used in pharmaceutical tablets, including flavoring agents, sweetening agents, flow aids, lubricants or other common tablet adjuvants, as will be apparent to those skilled in the art. Other disintegrants, such as crospovidone and sodium starch glycolate may be employed, although croscarmellose sodium is preferred.

In addition to the suspension tablet, the solid formulation of the present invention can be in the form of a powder, a tablet, a capsule, or other suitable solid dosage form (e.g., a pelleted form or an effervescing tablet, troche or powder), which creates the inventive solution in the presence of diluent or upon ingestion. For example, the water in the stomach secretions or water, which is used to swallow the solid dosage form, can serve as the aqueous diluent.

Compressed tablets are solid dosage forms prepared by compacting a formulation containing an active ingredient and excipients selected to aid the processing and improve the properties of the product. The term "compressed tablet" generally refers to a plain, uncoated tablet for oral ingestion, prepared by a single compression or by pre-compaction tapping followed by a final compression.

Dry oral formulations can contain excipients such as binders (for example, hydroxypropylmethylcellulose, polyvinyl pyrilodone, other cellulosic materials and starch), diluents (for example, lactose and other sugars, starch, dicalcium phosphate and cellulosic materials), disintegrating agents (for example, starch polymers and cellulosic materials) and lubricating agents (for example, stearates and talc).

Such solid forms can be manufactured as is well known in the art. Tablet forms can include, for example, one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmaceutically compatible carriers. The manufacturing processes may employ one, or a combination of, four established methods: (1) dry mixing; (2) direct compression; (3) milling; and (4) non-aqueous granulation. Lachman et al., *The Theory and Practice of Industrial Pharmacy* (1986). Such tablets may also comprise film coatings, which preferably dissolve upon oral ingestion or upon contact with diluent.

Non-limiting examples of buffering agents which could be utilized in such tablets include sodium bicarbonate, alkali earth metal salts such as calcium carbonate, calcium hydroxide, calcium lactate, calcium glycerophosphate, calcium acetate, magnesium carbonate, magnesium hydroxide, magnesium silicate, magnesium aluminate, aluminum hydroxide or aluminum magnesium hydroxide. A particular alkali earth metal salt useful for making an antacid tablet is calcium carbonate.

An example of a low density alkali earth metal salt useful for making the granules according to the present invention is extra light calcium carbonate available from Specialty Minerals Inc., Adams, Me. The density of the extra light calcium carbonate, prior to being processed according to the present invention, is about 0.37 g/ml. Other acceptable buffers are provided throughout this application.

The granules used to make the tablets according to one embodiment of the present invention are made by either spray drying or pre-compacting the raw materials. Prior to being processed into granules by either process, the density of the alkali earth metal salts useful in the present invention ranges from about 0.3 g/ml to about 0.55 g/ml, preferably about 0.35 g/ml to about 0.45 g/ml, even more preferably about 0.37 g/ml to about 0.42 g/ml.

Additionally, the present invention can be manufactured by utilizing micronized compounds in place of the granules or powder. Micronization is the process by which solid drug particles are reduced in size. Since the dissolution rate is directly proportional to the surface area of the solid, and reducing the particle size increases the surface area, reducing the particle size increases the dissolution rate. Although micronization results in increased surface area possibly causing particle aggregation, which can negate the benefit of micronization and is an expensive manufacturing step, it does have the significant benefit of increasing the dissolution rate of relatively water insoluble drugs, such as omeprazole and other proton pump inhibiting agents.

Although the tablets of this invention are primarily intended as a suspension dosage form, the granulations used to form the tablet may also be used to form rapidly disintegrating chewable tablets, lozenges, troches, or swallowable tablets. Therefore, the intermediate formulations as well as the process for preparing them provide additional novel aspects of the present invention.

Effervescent tablets and powders are also prepared in accordance with the present invention. Effervescent salts have been used to disperse medicines in water for oral administration. Effervescent salts are granules or coarse powders containing a medicinal agent in a dry mixture, usually composed of sodium bicarbonate, citric acid and tartaric acid. When the salts are added to water, the acids and the base react to liberate carbon dioxide gas, thereby causing "effervescence."

The choice of ingredients for effervescent granules depends both upon the requirements of the manufacturing process and the necessity of making a preparation which dissolves readily in water. The two required ingredients are at least one acid and at least one base. The base releases carbon dioxide upon reaction with the acid. Examples of such acids include, but are not limited to, tartaric acid and citric acid. Preferably, the acid is a combination of both tartaric acid and citric acid. Examples of bases include, but are not limited to, sodium carbonate, potassium bicarbonate and sodium bicarbonate. Preferably, the base is sodium bicarbonate, and the effervescent combination has a pH of about 6.0 or higher.

Effervescent salts preferably include the following ingredients, which actually produce the effervescence: sodium bicarbonate, citric acid and tartaric acid. When added to water the acids and base react to liberate carbon dioxide, resulting in effervescence. It should be noted that any acid-base combination which results in the liberation of carbon dioxide could be used in place of the combination of sodium bicarbonate and citric and tartaric acids, as long as the ingredients were suitable for pharmaceutical use, and result in a pH of about 6.0 or higher.

It should be noted that it requires 3 molecules of $NaHCO_3$ to neutralize 1 molecule of citric acid and 2 molecules of $NaHCO_3$ to neutralize 1 molecule of tartaric acid. It is desired that the approximate ratio of ingredients is as follows:

Citric Acid:Tartaric Acid:Sodium Bicarbonate=1:2:3.44 (by weight). This ratio can be varied and continue to produce an effective release of carbon dioxide. For example, ratios of about 1:0:3 or 0:1:2 are also effective.

The method of preparation of the effervescent granules of the present invention employs three basic processes: wet and dry granulation, and fusion. The fusion method is used for the preparation of most commercial effervescent powders. It should be noted that although these methods are intended for the preparation of granules, the formulations of effervescent salts of the present invention could also be prepared as tablets, according to well known prior art technology for tablet preparation.

Wet granulation is the oldest method of granule preparation. The individual steps in the wet granulation process of tablet preparation include milling and sieving of the ingredients; dry powder mixing; wet massing; granulation; and final grinding.

Dry granulation involves compressing a powder mixture into a rough tablet or "slug" on a heavy-duty rotary tablet press. The slugs are then broken up into granular particles by a grinding operation, usually by passage through an oscillation granulator. The individual steps include mixing of the powders; compressing (slugging); and grinding (slug reduction or granulation). No wet binder or moisture is involved in any of the steps.

The fusion method is the most preferred method for preparing the granules of the present invention. In this method, the compressing (slugging) step of the dry granulation process is eliminated. Instead, the powders are heated in an oven or other suitable source of heat.

IV. Proton Pump Inhibitors Administered with Parietal Cell Activators

Applicant has unexpectedly discovered that certain compounds, such as chocolate, calcium and sodium bicarbonate and other alkaline substances, stimulate the parietal cells and enhance the pharmacologic activity of the proton pump inhibitor administered. For the purposes of this application, "parietal cell activator" or "activator" shall mean any compound or mixture of compounds possessing such stimulatory effect including, but not limited to, chocolate, sodium bicarbonate, calcium (e.g., calcium carbonate, calcium gluconate, calcium hydroxide, calcium acetate and calcium glycerophosphate), peppermint oil, spearmint oil, coffee, tea and colas (even if decaffeinated), caffeine, theophylline, theobromine, and amino acids (particularly aromatic amino acids such as phenylalanine and tryptophan) and combinations thereof, and the salts thereof.

Such parietal cell activators are administered in an amount sufficient to produce the desired stimulatory effect without causing untoward side effects to subjects. For example, chocolate, as raw cocoa, is administered in an amount of about 5 mg to 2.5 g per 20 mg dose of omeprazole (or equivalent pharmacologic dose of other proton pump inhibitor). The dose of activator administered to a mammal, particularly a human, in the context of the present invention should be sufficient to effect a therapeutic response (i.e., enhanced effect of proton pump inhibitor) over a reasonable time frame. The dose will be determined by the strength of the particular compositions employed and the condition of the person, as well as the body weight of the person to be treated. The size of the dose also will be determined by the existence, nature, and extent of any adverse side effects that might accompany the administration of a particular composition.

The approximate effective ranges for various parietal cell activators per 20 mg dose of omeprazole (or equivalent dose of other proton pump inhibitor) are:

Chocolate (raw cocoa)—5 mg to 2.5 g
Sodium bicarbonate—7 mEq to 25 mEq
Calcium carbonate—1 mg to 1.5 g
Calcium gluconate—1 mg to 1.5 g
Calcium lactate—1 mg to 1.5 g
Calcium hydroxide—1 mg to 1.5 g
Calcium acetate—0.5 mg to 1.5 g
Calcium glycerophosphate—0.5 mg to 1.5 g
Peppermint oil—(powdered form) 1 mg to 1 g
Spearmint oil—(powdered form) 1 mg to 1 g
Coffee—20 ml to 240 ml
Tea—20 ml to 240 ml
Cola—20 ml to 240 ml
Caffeine—0.5 mg to 1.5 g
Theophylline—0.5 mg to 1.5 g
Theobromine—0.5 mg to 1.5 g
Phenylalanine—0.5 mg to 1.5 g
Tryptophan—0.5 mg to 1.5 g Pharmaceutically acceptable carriers are well-known to those who are skilled in the art. The choice of carrier will be determined, in part, both by the particular composition and by the particular method used to administer the composition. Accordingly, there is a wide variety of suitable formulations of the pharmaceutical compositions of the present invention.

V. Examples

The present invention is further illustrated by the following formulations, which should not be construed as limiting in any way. The practice of the present invention will employ, unless otherwise indicated, conventional techniques of pharmacology and pharmaceutics, which are within the skill of the art.

Example I

A. Fast Disintegrating Suspension Tablets of Omeprazole.

A fast disintegrating tablet is compounded as follows: Croscarmellose sodium 300 g is added to the vortex of a rapidly stirred beaker containing 3.0 kg of deionized water. This slurry is mixed for 10 minutes. Omeprazole 90 g (powdered) is placed in the bowl of a Hobart mixer. After mixing, the slurry of croscarmellose sodium is added slowly to the omeprazole in the mixer bowl, forming a granulation, which is then placed in trays and dried at 70° C. for three hours. The dry granulation is then placed in a blender, and to it is added 1,500 g of Avicel® AC-815 (85% microcrystalline cellulose coprocessed with 15% of a calcium, sodium alginate complex) and 1,500 g of Avicel® PH-302 (microcrystalline cellulose). After this mixture is thoroughly blended, 35 g of magnesium stearate is added and mixed for 5 minutes. The resulting mixture is compressed into tablets on a standard tablet press (Hata HS). These tablets have an average weight of about 0.75 g, and contain about 20 mg omeprazole. These tablets have low friability and rapid disintegration time. This formulation may be dissolved in an aqueous solution containing a buffering agent for immediate oral administration.

Alternatively, the suspension tablet may be swallowed whole with a solution of buffering agent. In both cases, the preferred solution is sodium bicarbonate 8.4%. As a further alternative, sodium bicarbonate powder (about 975 mg per 20 mg dose of omeprazole (or an equipotent amount of other proton pump inhibitor) is compounded directly into the tablet. Such tablets are then dissolved in water or sodium bicarbonate 8.4%, or swallowed whole with an aqueous diluent.

| B1. 10 mg Tablet Formula. | |
|---|---|
| Omeprazole | 10 mg |
|  | (or lansoprazole or pantoprazole |
|  | or other proton pump inhibitor in an |
|  | equipotent amount) |
| Calcium lactate | 175 mg |
| Calcium glycerophosphate | 175 mg |
| Sodium bicarbonate | 250 mg |
| Aspartame calcium (phenylalanine) | 0.5 mg |
| Colloidal silicon dioxide | 12 mg |
| Corn starch | 15 mg |
| Croscarmellose sodium | 12 mg |
| Dextrose | 10 mg |
| Peppermint | 3 mg |
| Maltodextrin | 3 mg |
| Mannitol | 3 mg |
| Pregelatinized starch | 3 mg |

| B2. 10 mg Tablet Formula. | |
|---|---|
| Proton pump inhibitor: one of the following: | |
| Omeprazole | 10 mg |
| Lansoprazole | 15 mg |
| Pantoprazole sodium | 20 mg |
| Rabeprazole sodium | 10 mg |
| Other proton pump inhibitor in an equipotent amount | |
| Calcium lactate | 375 mg |
| Calcium glycerophosphate | 375 mg |
| Aspartame calcium (phenylalanine) | 0.5 mg |

-continued

| | |
|---|---|
| Colloidal silicon dioxide | 12 mg |
| Corn starch | 15 mg |
| Croscarmellose sodium | 12 mg |
| Dextrose | 10 mg |
| Peppermint | 3 mg |
| Maltodextrin | 20 mg |
| Mannitol | 30 mg |
| Pregelatinized starch | 30 mg |

B3. 10 mg Tablet Formula.

Proton pump inhibitor: one of the following:

| | |
|---|---|
| Omeprazole | 10 mg |
| Lansoprazole | 15 mg |
| Pantoprazole sodium | 20 mg |
| Rabeprazole sodium | 10 mg |
| Other proton pump inhibitor in an equipotent amount | |
| Sodium bicarbonate | 750 mg |
| Aspartame sodium (phenylalanine) | 0.5 mg |
| Colloidal silicon dioxide | 12 mg |
| Corn starch | 15 mg |
| Croscarmellose sodium | 12 mg |
| Dextrose | 10 mg |
| Peppermint | 3 mg |
| Maltodextrin | 20 mg |
| Mannitol | 30 mg |
| Pregelatinized starch | 30 mg |

C1. 20 mg Tablet Formula.

| | |
|---|---|
| Omeprazole | 20 mg (or lansoprazole or pantoprazole or other proton pump inhibitor in an equipotent amount) |
| Calcium lactate | 175 mg |
| Calcium glycerophosphate | 175 mg |
| Sodium bicarbonate | 250 mg |
| Aspartame calcium (phenylalanine) | 0.5 mg |
| Colloidal silicon dioxide | 12 mg |
| Corn starch | 15 mg |
| Croscarmellose sodium | 12 mg |
| Dextrose | 10 mg |
| Calcium hydroxide | 10 mg |
| Peppermint | 3 mg |
| Maltodextrin | 3 mg |
| Mannitol | 3 mg |
| Pregelatinized starch | 3 mg |

C2. 20 mg Tablet Formula.

Proton pump inhibitor: One of the following:

| | |
|---|---|
| Omeprazole | 20 mg |
| Lansoprazole | 30 mg |
| Pantoprazole | 40 mg |
| Other proton pump inhibitor in an equipotent amount | |
| Calcium lactate | 375 mg |
| Calcium glycerophosphate | 375 mg |
| Aspartame calcium (phenylalanine) | 0.5 mg |
| Colloidal silicon dioxide | 12 mg |
| Corn starch | 15 mg |
| Croscarmellose sodium | 12 mg |
| Dextrose | 10 mg |
| Peppermint | 3 mg |
| Maltodextrin | 20 mg |
| Mannitol | 30 mg |
| Pregelatinized starch | 30 mg |

C3. 20 mg Tablet Formula.

Proton pump inhibitor: One of the following:

| | |
|---|---|
| Omeprazole | 20 mg |
| Lansoprazole | 30 mg |
| Pantoprazole | 40 mg |

-continued

| | |
|---|---|
| Other proton pump inhibitor in an equipotent amount | |
| Sodium bicarbonate | 750 mg |
| Aspartame sodium (phenylalanine) | 0.5 mg |
| Colloidal silicon dioxide | 12 mg |
| Corn starch | 15 mg |
| Croscarmellose sodium | 12 mg |
| Dextrose | 10 mg |
| Peppermint | 3 mg |
| Maltodextrin | 20 mg |
| Mannitol | 30 mg |
| Pregelatinized starch | 30 mg |

D1. Tablet for Rapid Dissolution.

| | |
|---|---|
| Omeprazole | 20 mg (or lansoprazole or pantoprazole or other proton pump inhibitor in an equipotent amount) |
| Calcium lactate | 175 mg |
| Calcium glycerophosphate | 175 mg |
| Sodium bicarbonate | 500 mg |
| Calcium hydroxide | 50 mg |
| Croscarmellose sodium | 12 mg |

D2. Tablet for Rapid Dissolution.

Proton pump inhibitor: One of the following:

| | |
|---|---|
| Omeprazole | 20 mg |
| Lansoprazole | 30 mg |
| Pantoprazole | 40 mg |
| Rabeprazole sodium | 20 mg |
| Esomeprazole magnesium | 20 mg |
| Other proton pump inhibitor in an equipotent amount | |
| Calcium lactate | 300 mg |
| Calcium glycerophosphate | 300 mg |
| Calcium hydroxide | 50 mg |
| Croscarmellose sodium | 12 mg |

D3. Tablet for Rapid Dissolution.

Proton pump inhibitor: One of the following:

| | |
|---|---|
| Omeprazole | 20 mg |
| Lansoprazole | 30 mg |
| Pantoprazole | 40 mg |
| Rabeprazole sodium | 20 mg |
| Esomeprazole magnesium | 20 mg |
| Other proton pump inhibitor in an equipotent amount | |
| Sodium bicarbonate | 700 mg |
| Trisodium phosphate dodecahydrate | 100 mg |
| Croscarmellose sodium | 12 mg |

E1. Powder for Reconstitution for Oral Use (or per ng tube).

| | |
|---|---|
| Omeprazole | 20 mg (or lansoprazole or pantoprazole or other proton pump inhibitor in an equipotent amount) |
| Calcium lactate | 175 mg |
| Calcium glycerophosphate | 175 mg |
| Sodium bicarbonate | 500 mg |
| Calcium hydroxide | 50 mg |
| Glycerine | 200 mg |

E2. Powder for Reconstitution for Oral Use (or per ng tube).

Proton pump inhibitor: One of the following:

| | |
|---|---|
| Omeprazole | 20 mg |
| Lansoprazole | 30 mg |
| Pantoprazole | 40 mg |
| Rabeprazole sodium | 20 mg |
| Esomeprazole magnesium | 20 mg |

-continued

| | |
|---|---|
| Other proton pump inhibitor in an equipotent amount | |
| Calcium lactate | 300 mg |
| Calcium glycerophosphate | 300 mg |
| Calcium hydroxide | 50 mg |
| Glycerine | 200 mg |

E3. Powder for Reconstitution for Oral Use (or per ng tube).

| | |
|---|---|
| Proton pump inhibitor: One of the following: | |
| Omeprazole | 20 mg |
| Lansoprazole | 30 mg |
| Pantoprazole | 40 mg |
| Rabeprazole sodium | 20 mg |
| Esomeprazole magnesium | 20 mg |
| Other proton pump inhibitor in an equipotent amount | |
| Sodium bicarbonate | 850 mg |
| Trisodium phosphate | 50 mg |

F1. 10 mg Tablet Formula.

| | |
|---|---|
| Omeprazole | 10 mg (or lansoprazole or pantoprazole or other proton pump inhibitor in an equipotent amount) |
| Calcium lactate | 175 mg |
| Calcium glycerophosphate | 175 mg |
| Sodium bicarbonate | 250 mg |
| Polyethylene glycol | 20 mg |
| Croscarmellose sodium | 12 mg |
| Peppermint | 3 mg |
| Magnesium silicate | 1 mg |
| Magnesium stearate | 1 mg |

F2. 10 mg Tablet Formula.

| | |
|---|---|
| Proton pump inhibitor: One of the following: | |
| Omeprazole | 10 mg |
| Lansoprazole | 15 mg |
| Pantoprazole sodium | 20 mg |
| Rabeprazole sodium | 10 mg |
| Esomeprazole magnesium | 10 mg |
| Other proton pump inhibitor in an equipotent amount | |
| Calcium lactate | 475 mg |
| Calcium glycerophosphate | 250 mg |
| Polyethylene glycol | 20 mg |
| Croscarmellose sodium | 12 mg |
| Peppermint | 3 mg |
| Magnesium silicate | 10 mg |
| Magnesium stearate | 10 mg |

F3. 10 mg Tablet Formula.

| | |
|---|---|
| Proton pump inhibitor: One of the following: | |
| Omeprazole | 10 mg |
| Lansoprazole | 15 mg |
| Pantoprazole sodium | 20 mg |
| Rabeprazole sodium | 10 mg |
| Esomeprazole magnesium | 10 mg |
| Other proton pump inhibitor in an equipotent amount | |
| Sodium bicarbonate | 700 mg |
| Polyethylene glycol | 20 mg |
| Croscarmellose sodium | 12 mg |
| Peppermint | 3 mg |
| Magnesium silicate | 10 mg |
| Magnesium stearate | 10 mg |

G1. 10 mg Tablet Formula.

| | |
|---|---|
| Omeprazole | 10 mg (or lansoprazole or pantoprazole or other proton pump inhibitor in an equipotent amount) |
| Calcium lactate | 200 mg |
| Calcium glycerophosphate | 200 mg |
| Sodium bicarbonate | 400 mg |
| Croscarmellose sodium | 12 mg |
| Pregelatinized starch | 3 mg |

G2. 10 mg Tablet Formula.

| | |
|---|---|
| Proton pump inhibitor: One of the following: | |
| Omeprazole | 10 mg |
| Lansoprazole | 15 mg |
| Pantoprazole sodium | 20 mg |
| Rabeprazole sodium | 10 mg |
| Esomeprazole magnesium | 10 mg |
| Other proton pump inhibitor in an equipotent amount | |
| Calcium lactate | 400 mg |
| Calcium glycerophosphate | 400 mg |
| Croscarmellose sodium | 12 mg |
| Pregelatinized starch | 3 mg |

G3. 10 mg Tablet Formula.

| | |
|---|---|
| Proton pump inhibitor: One of the following: | |
| Omeprazole | 10 mg |
| Lansoprazole | 15 mg |
| Pantoprazole sodium | 20 mg |
| Rabeprazole sodium | 10 mg |
| Esomeprazole magnesium | 10 mg |
| Other proton pump inhibitor in an equipotent amount | |
| Sodium bicarboante | 750 mg |
| Croscarmellose sodium | 12 mg |
| Pregelatinized starch | 3 mg |

All of the tablets and powders of this Example may be swallowed whole, chewed or mixed with an aqueous medium prior to administration.

Example II
Standard Tablet of Proton Pump Inhibitor and Buffering Agent.

Ten (10) tablets were prepared using a standard tablet press, each tablet comprising about 20 mg omeprazole and about 975 mg sodium bicarbonate uniformly dispersed throughout the tablet. To test the disintegration rate of the tablets, each was added to 60 ml of water. Using previously prepared liquid omeprazole/sodium bicarbonate solution as a visual comparator, it was observed that each tablet was completely dispersed in under three (3) minutes.

Another study using the tablets compounded according to this Example evaluated the bioactivity of the tablets in five (5) adult critical care subjects. Each subject was administered one tablet via ng with a small amount of water, and the pH of ng aspirate was monitored using paper measure. The pH for each subject was evaluated for 6 hours and remained above 4, thus demonstrating the therapeutic benefit of the tablets in these patients.

Tablets were also prepared by boring out the center of sodium bicarbonate USP 975 mg tablets with a knife. Most of the removed sodium bicarbonate powder was then triturated with the contents of a 20 mg Prilosec® capsule and the resulting mixture was then packed into the hole in the tablet and sealed with glycerin.

Example III
Proton Pump Inhibitor Central Core Tablet.

Tablets are prepared in a two-step process. First, about 20 mg of omeprazole is formed into a tablet as is known in the art to be used as a central core. Second, about 975 mg sodium bicarbonate USP is used to uniformly surround the central core to form an outer protective cover of sodium bicarbonate. The central core and outer cover are both prepared using standard binders and other excipients to create a finished, pharmaceutically acceptable tablet. The tablets may be swallowed whole with a glass of water.

Example IV
Effervescent Tablets and Granules.

The granules of one 20 mg Prilosec® capsule were emptied into a mortar and triturated with a pestle to a fine powder. The omeprazole powder was then geometrically diluted with about 958 mg sodium bicarbonate USP, about 832 mg citric acid USP and about 312 mg potassium carbonate USP to form a homogeneous mixture of effervescent omeprazole powder. This powder was then added to about 60 ml of water whereupon the powder reacted with the water to create effervescence. A bubbling solution resulted of omeprazole and principally the antacids sodium citrate and potassium citrate. The solution was then administered orally to one adult male subject and gastric pH was measured using pHydrion paper. The results were as follows:

| Time Interval | pH Measured |
|---|---|
| Immediately prior to dose | 2 |
| 1 hour post dose | 7 |
| 2 hours post dose | 6 |
| 4 hours post dose | 6 |
| 6 hours post dose | 5 |
| 8 hours post dose | 4 |

One skilled in the art of pharmaceutical compounding will appreciate that bulk powders can be manufactured using the above ratios of ingredients, and that the powder can be pressed into tablets using standard binders and excipients. Such tablets are then mixed with water to activate the effervescent agents and create the desired solution. In addition, lansoprazole 30 mg (or an equipotent dose of other proton pump inhibitor) can be substituted for omeprazole.

The effervescent powder and tablets can alternatively be formulated by employing the above mixture but adding an additional 200 mg of sodium bicarbonate USP to create a resulting solution with a higher pH. Further, instead of the excess 200 mg of sodium bicarbonate, 100 mg of calcium glycerophosphate or 100 mg of calcium lactate can be employed. Combinations of the same can also added.

Example V
Parietal Cell Activator "Choco-Base™" Formulations and Efficacy.

Children are affected by gastro esophageal reflux disease (GERD) with atypical manifestations. Many of these atypical symptoms are difficult to control with traditional drugs such as $H_2$-antagonists, cisapride, or sucralfate. Proton pump inhibiting agents are more effective in controlling gastric pH and the symptoms of gastroesophageal reflux disease than other agents. However, proton pump inhibiting agents are not available in dosage forms that are easy to administer to young children. To address this problem, applicant employed omeprazole or lansoprazole in a buffered chocolate suspension (Choco-Base), in children with manifestations of gastroesophageal reflux disease.

Applicant performed a retrospective evaluation of children with gastroesophageal reflux disease referred to the University of Missouri-Columbia from 1995 to 1998 who received treatment with the experimental omeprazole or lansoprazole Choco-Base suspension formulated in accordance with Formulation 1 stated below. Data were included on all patients with follow up information sufficient to draw conclusions about pre/post treatment (usually >6 months). There were 25 patients who met the criteria for this evaluation. Age range was several weeks to greater than 5 years. Most patients had a history of numerous unsuccessful attempts at ameliorating the effects of gastroesophageal reflux disease. Medication histories indicated many trials of various drugs.

The primary investigator reviewed all charts for uniformity of data collection. When insufficient data was available in the University charts, attempts were made to review charts in the local primary care physicians' offices for follow-up data. If information was still unavailable to review, attempts were made to contact family for follow-up. If data were still unavailable the patients were considered inevaluable.

Patient charts were reviewed in detail. Data noted were date of commencement of therapy, date of termination of therapy and any reason for termination other than response to treatment. Patient demographics were also recorded, as were any other medical illnesses. Medical illnesses were divided grossly into those that are associated with or exacerbate gastroesophageal reflux disease and those that do not.

Patient charts were examined for evidence of response to therapy. As this was largely a referral population, and a retrospective review, quantification of symptomatology based on scores, office visits and ED visits was difficult. Therefore, applicant examined charts for evidence of an overall change in patient symptoms. Any data to point towards improvement, decline or lack of change were examined and recorded.

Results.

A total of 33 pediatric patients to date have been treated with the above-described suspension at the University of Missouri—Columbia. Of the 33 patients, 9 were excluded from the study, all based upon insufficient data about commencement, duration or outcome in treatment with proton pump inhibitor therapy. This left 24 patients with enough data to draw conclusions.

Figure 5:
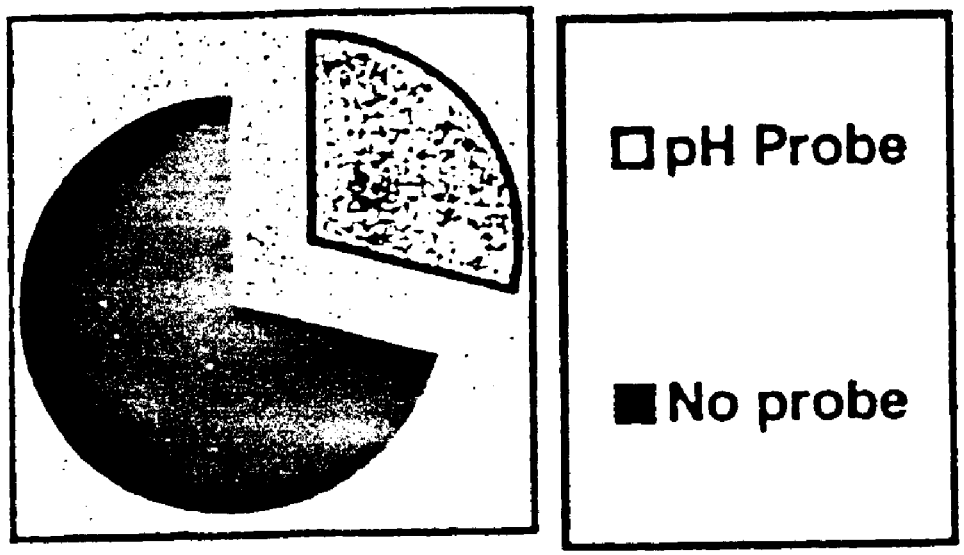
FIG. 5 is a graph illustrating a pH probe confirmation of gastroesophageal reflux disease.
Figure 6:
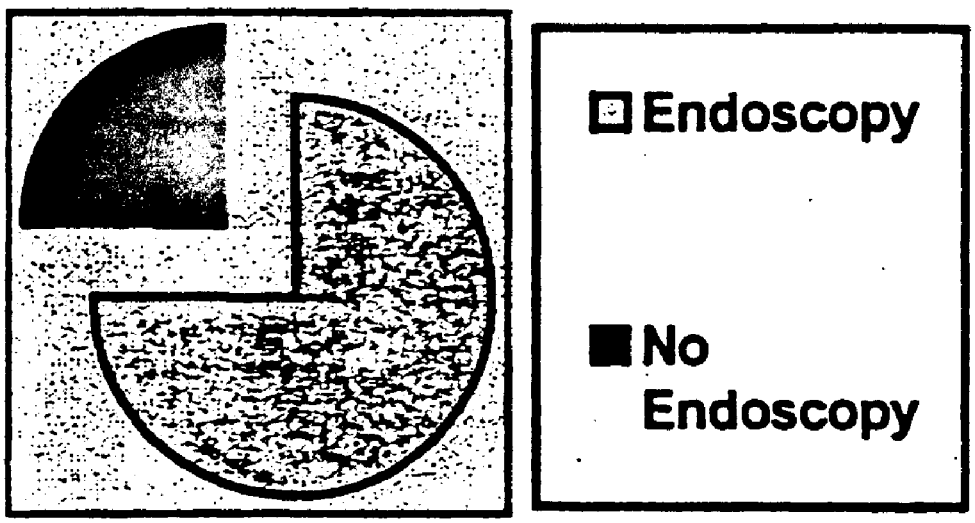
FIG. 6 is a graph illustrating an endoscopic confirmation of gastroesophageal reflux disease.

Of the 24 remaining patients, 18 were males and 6 females. Ages at implementation of proton pump inhibitor therapy ranged from 2 weeks of age to 9 years old. Median age at start of therapy was 26.5 months [mean of 37 mo.]. Early on, reflux was usually documented by endoscopy and confirmed by pH probe. Eventually, pH probe was dropped and endoscopy was the sole method for documenting reflux, usually at the time of another surgery (most often T-tubes or adenoidectomy). Seven patients had pH probe confirmation of gastroesophageal reflux disease, whereas 18 had endoscopic confirmation of reflux including all eight who had pH probing done (See FIGS. 5 and 6). Reflux was diagnosed on endoscopy most commonly by cobblestoning of the tracheal wall, with laryngeal and pharyngeal cobblestoning as findings in a few patients. Six patients had neither pH nor endoscopic documentation of gastroesophageal reflux disease, but were tried on proton pump inhibitor therapy based on symptomatology alone.

Past medical history was identified in each chart. Ten patients had reflux-associated diagnoses. These were most commonly cerebral palsy, prematurity and Pierre Robin sequence. Other diagnoses were Charcot-Marie-Tooth disease, Velocardiofacial syndrome, Down syndrome and De George's syndrome. Non-reflux medical history was also identified and recorded separately (See Table 2 below).

Patients were, in general, referral patients from local family practice clinics, pediatricians, or other pediatric health care professionals. Most patients were referred to ENT for upper airway problems, sinusitis, or recurrent/chronic otitis media that had been refractory to medical therapy as reported by the primary care physician. Symptoms and signs most commonly found in these patients were recorded and tallied. All signs and symptoms were broken down into six major categories: (1) nasal; (2) otologic; (3) respiratory; (4) gastrointestinal; (5) sleep-related; and (6) other. The most common problems fell into one or all of the first 3 categories (See Table 1 below).

Figure 7:
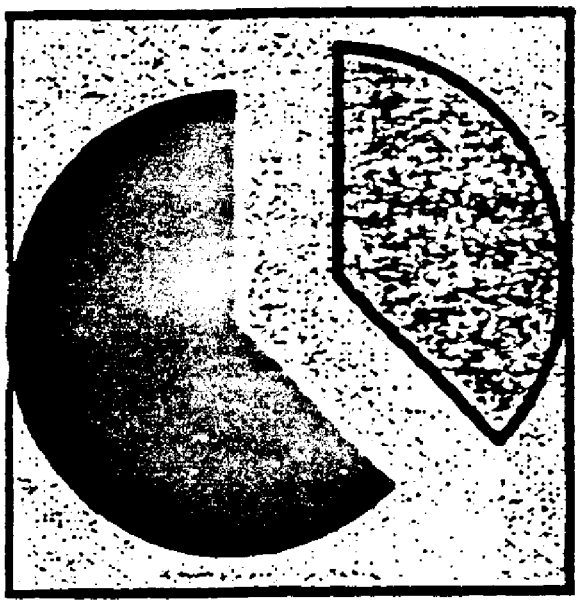
FIG. 7 is a graph illustrating the percentage of patients who had undergone any type of reflux therapy in the past.

Most patients had been treated in the past with medical therapy in the form of antibiotics, steroids, asthma medications and other diagnosis-appropriate therapies. In addition, nine of the patients had been on reflux therapy in the past, most commonly in the form of conservative therapy such as head of bed elevation 300, avoidance of evening snacks, avoidance of caffeinated beverages as well as cisapride and ranitidine (See FIG. 7).

The proton pump inhibitor suspension used in this group of patients was Choco-Base suspension of either lansoprazole or omeprazole. The dosing was very uniform, with patients receiving doses of either 10 or 20 mg of omeprazole and 23 mg of lansoprazole. Initially, in April of 1996 when therapy was first instituted 10 mg of omeprazole was used. There were 3 patients in this early phase who were treated initially with 10 mg po qd of omeprazole. All three subsequently were increased to either 20 mg po qd of omeprazole or 23 mg po qd of lansoprazole. All remaining patients were given either the 20 mg omeprazole or the 23 mg lansoprazole treatment qd, except in one case, where 30 mg of lansoprazole was used. Patients were instructed to take their doses once per day, preferably at night in most cases. Suspensions were all filled through the University of Missouri Pharmacy at Green Meadows. This allowed for tracking of usage through refill data.

Most patients responded favorably to and tolerated the once daily dosing of Choco-Base proton pump inhibitor suspension. Two patients had documented adverse effects associated with the use of the proton pump inhibitor suspension. In one patient, the mother reported increased burping up and dyspepsia, which was thought to be related to treatment failure. The other patient had small amounts of bloody stools per mother. This patient never had his stool tested, as his bloody stool promptly resolved upon cessation of therapy, with no farther sequellae. The other 23 patients had no documented adverse effects.

Figure 8:
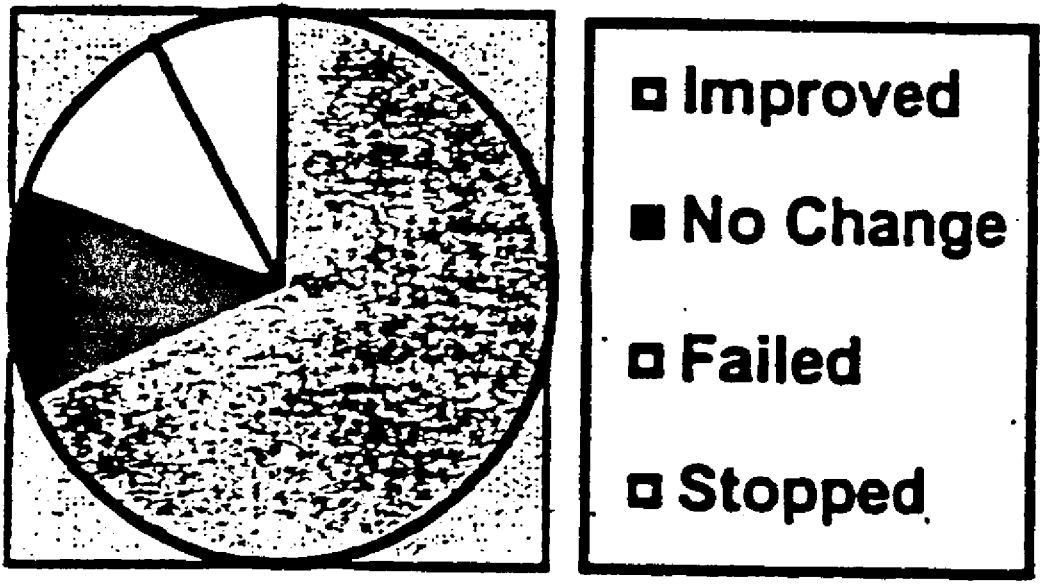
FIG. 8 is a graph illustrating the effectiveness of the Choco-Base Formulation 1.

Patients were categorized based on review of clinic notes and chart review into general categories: (1) improved; (2) unchanged; (3) failed; and (4) inconclusive. Of 24 patients with sufficient data for follow up, 18 showed improvement in symptomatology upon commencement of proton pump inhibitor therapy [72%]. The seven who did not respond were analyzed and grouped. Three showed no change in symptomatology and clinical findings while on therapy, one complained of worsening symptoms while on therapy, one patient had therapy as prophylaxis for surgery, and two stopped therapy just after its commencement (see FIG. 8). Setting aside the cases in which therapy was stopped before conclusions could be drawn and the case in which proton pump inhibitor therapy was for purely prophylactic reasons, leaves (17/21) 81% of patients that responded to Choco-Base suspension. This means that 19% (4/21) of patients received no apparent benefit from proton pump inhibitor therapy. Of all these patients, only 4% complained of worsening symptoms and the side effects were 4% (1/21) and were mild bloody stool that completely resolved upon cessation of therapy.

Discussion.

Gastroesophageal reflux disease in the pediatric population is relatively common, affecting almost 50% of newborns. Even though most infants outgrow physiologic reflux, pathologic reflux still affects approximately 5% of all children throughout childhood. Recently considerable data has pointed to reflux as an etiologic factor in extra-esophageal areas. gastroesophageal reflux disease has been attributed to sinusitis, dental caries, otitis media, asthma, apnea, arousal, pneumonia, bronchitis, and cough, among others. Despite the common nature of reflux, there seems to have been little improvement in therapy for reflux, especially in the non-surgical arena.

The standard of therapy for the treatment of gastroesophageal reflux disease in the pediatric population has become a progression from conservative therapy to a combination of a pro-kinetic agent and H-2 blocker therapy. Nonetheless, many patients fail this treatment protocol and become surgical candidates. In adults, proton pump inhibitor therapy is effective in 90% of those treated for gastroesophageal reflux disease. As a medical alternative to the H-2 blockers, the proton pump inhibiting agents have not been studied extensively in the pediatric population. Part of the reason for this lack of data may be related to the absence of a suitable dosage formulation for this very young population, primarily under 2 years of age, that does not swallow capsules or tablets. It would be desirable to have a true liquid formulation (solution or suspension) with good palatability such as is used for oral antibiotics, decongestants, antihistamines, H-2 blockers, cisapride, metoclopramide, etc. The use of lansoprazole granules (removed from the gelatin capule) and sprinkled on applesauce has been approved by the Food and Drug Administration as an alternative method of drug administration in adults but not in children. Published data are lacking on the efficacy of the lansoprazole sprinkle method in children. Omeprazole has been studied for bioequivalence as a sprinkle in adults and appears to produce comparable serum concentrations when compared to the standard capsule. Again no data are available on the omeprazole sprinkle in children. An additional disadvantage of omeprazole is its taste which is quinine-like. Even when suspended in juice, applesauce or the like, the bitter nature of the medicine is easily tasted even if one granule is chewed. For this reason applicant eventually progressed to use lansoprazole in Choco-Base. Pantoprazole and rabeprazole are available as enteric-coated tablets only. Currently, none of the proton pump inhibiting agents available in the United States are approved for pediatric use. There is some controversy as to what the appropriate dosage should be in this group of patients. A recent review by Israel D., et al. suggests that effective proton pump inhibitor dosages should be higher than that originally reported, i.e., from 0.7 mg/kg to 2 or 3 mg/kg omeprazole. Since toxicity with the proton pump inhibiting agents is not seen even at >50 mg/kg, there appears little risk associated with the higher dosages. Based on observations at the University of Missouri consistent with the findings of this review, applicant established a simple fixed dosage regimen of 10 ml Choco-Base suspension daily. This 10 ml dose provided 20 mg omeprazole or 23 mg lansoprazole.

In the ICU setting, the University of Missouri-Columbia has been using an unflavored proton pump inhibitor suspension given once daily per various tubes (nasogastric, g-tube, jejunal feeding tube, duo tube, etc.) for stress ulcer prophylaxis. It seemed only logical that if this therapy could be made into a palatable form, it would have many ideal drug characteristics for the pediatric population. First, it would be liquid, and therefore could be administered at earlier ages. Second, if made flavorful it could help to reduce noncompliance. Third, it could afford once daily dosing, also helping in reducing noncompliance. In the process, applicant discovered that the dosing could be standardized, which nearly eliminated dosing complexity.

Choco-Base is a product which protects drugs which are acid labile, such as proton pump inhibiting agents, from acid degradation. The first few pediatric patients with reflux prescribed Choco-Base were sicker patients. They had been on prior therapy and had been diagnosed both by pH probe and endoscopy. In the first few months, applicant treated patients with 10 mg of omeprazole qd (1 mg/kg) and found this to be somewhat ineffective, and quickly increased the dosing to 20 mg (2 mg/kg) of omeprazole. About halfway through the study, applicant began using lansoprazole 23 mg po qd. Applicant's standard therapy was then either 20 mg of omeprazole or 23 mg of lansoprazole once daily. The extra 3 mg of lansoprazole is related only to the fact that the final concentration was 2.25 mg/ml, and applicant desired to keep dosing simple, so he used a 10 ml suspension.

The patients that were treated represented a tertiary care center population, and they were inherently sicker and refractory to medical therapy in the past. The overall 72% success rate is slightly lower than the 90% success rates of proton pump inhibiting agents in the adult population, but this can be attributed to the refractory nature of their illness, most having failed prior non-proton pump inhibitor treatment. The population in this study is not indicative of general practice populations.

Conclusion.

Proton pump inhibitor therapy is a beneficial therapeutic option in the treatment of reflux related symptoms in the pediatric population. Its once daily dosing and standard dosing scheme combined with a palatable formulation makes it an ideal pharmacologic agent.

TABLE 1

| Symptoms | Patient Numbers |
|---|---|
| Nasal: | 35 |
| Sinusitis | 7 |
| Congestion | 8 |
| Nasal discharge | 16 |
| Other | 4 |
| Otologic: | 26 |
| Otitis Media | 17 |
| Otorrhea | 9 |
| Respiratory: | 34 |
| Cough | 10 |
| Wheeze | 11 |
| Respiratory Distress: | 5 |
| Pneumonia | 2 |
| Other | 6 |
| Gastrointestinal: | 10 |
| Abdominal Pain | 1 |
| Reflux/Vomiting | 4 |
| Other | 4 |
| Sleep Disturbances: | 11 |
| Other | 2 |

TABLE 2

| | |
|---|---|
| Reflux Associated: | 12 |
| Premature | 5 |
| Pierre-Robin | 2 |
| Cerebral Palsy | 2 |
| Down Syndrome | 1 |
| Charcot-Marie-Tooth | 1 |
| Velocardiofacial Syndrome | 1 |
| Other Medical History | 12 |
| Cleft Palate | 3 |
| Asthma | 3 |
| Autism | 2 |
| Seizure Disorder | 1 |
| Diabetes Mellitus | 1 |
| Subglottic Stenosis | 1 |
| Tracheostomy Dependent | 1 |

FORMULATION 1

| PART A INGREDIENTS | AMOUNT (mg) |
|---|---|
| Omeprazole | 200 |
| Sucrose | 26000 |
| Sodium Bicarbonate | 9400 |
| Cocoa | 1800 |
| Corn Syrup Solids | 6000 |
| Sodium Caseinate | 1000 |
| Soy Lecithin | 150 |
| Sodium Chloride | 35 |
| Tricalcium Phosphate | 20 |
| Dipotassium Phosphate | 12 |
| Silicon Dioxide | 5 |
| Sodium Stearoyl Lactylate | 5 |

| PART B INGREDIENTS | AMOUNT (ml) |
|---|---|
| Distilled Water | 100 |

COMPOUNDING INSTRUCTIONS

Add Part B to Part A to create a total volume of approximately 130 ml with an omeprazole concentration of about 1.5 mg/ml.

FORMULATION 2

| PART A INGREDIENTS (mg) | AMOUNT (mg) |
|---|---|
| Sucrose | 26000 |
| Cocoa | 1800 |
| Corn Syrup Solids | 6000 |
| Sodium Caseinate | 1000 |
| Soy Lecithin | 150 |
| Sodium Chloride | 35 |
| Tricalcium Phosphate | 20 |
| Dipotassium Phosphate | 12 |
| Silicon Dioxide | 5 |
| Sodium Stearoyl Lactylate | 5 |

| PART B INGREDIENTS | AMOUNT |
|---|---|
| Distilled Water | 100 ml |
| Sodium Bicarbonate | 8400 mg |
| Omeprazole | 200 mg |

COMPOUNDING INSTRUCTIONS

Mix the constituents of Part B together thoroughly and then add to Part A. This results in a total volume of approximately 130 ml with an omeprazole concentration of about 1.5 mg/ml.

FORMULATION 3

| PART A INGREDIENTS (mg) | AMOUNT (mg) |
|---|---|
| Sucrose | 26000 |
| Sodium Bicarbonate | 9400 |
| Cocoa | 1800 |
| Corn Syrup Solids | 6000 |
| Sodium Caseinate | 1000 |
| Soy Lecithin | 150 |
| Sodium Chloride | 35 |
| Tricalcium Phosphate | 20 |
| Dipotassium Phosphate | 12 |
| Silicon Dioxide | 5 |
| Sodium Stearoyl Lactylate | 5 |
| PART B INGREDIENTS | AMOUNT |
| Distilled Water | 100 ml |
| Omeprazole | 200 mg |

COMPOUNDING INSTRUCTIONS

This formulation is reconstituted at the time of use by a pharmacist. Part B is mixed first and is then uniformly mixed with the components of Part A. A final volume of about 130 ml is created having an omeprazole concentration of about 1.5 mg/ml.

FORMULATION 4

| PART A INGREDIENTS (mg) | AMOUNT (mg) |
|---|---|
| Sucrose | 26000 |
| Cocoa | 1800 |
| Corn Syrup Solids | 6000 |
| Sodium Caseinate | 1000 |
| Soy Lecithin | 150 |
| Sodium Chloride | 35 |
| Tricalcium Phosphate | 20 |
| Dipotassium Phosphate | 12 |
| Silicon Dioxide | 5 |
| Sodium Stearoyl Lactylate | 5 |
| PART B INGREDIENTS | AMOUNT |
| Distilled Water | 100 ml |
| Sodium Bicarbonate | 8400 mg |
| Omeprazole | 200 mg |

COMPOUNDING INSTRUCTIONS

This formulation is reconstituted at the time of use by a pharmacist. Part B is mixed first and is then uniformly mixed with the components of Part A. A final volume of about 130 ml is created having an omeprazole concentration of about 1.5 mg/ml.

In all four of the above formulations, lansoprazole or other proton pump inhibitor can be substituted for omeprazole in equipotent amounts. For example, 300 mg of lansoprazole may be substituted for the 200 mg of omeprazole. Additionally, aspartame can be substituted for sucrose, and the following other ingredients can be employed as carriers, adjuvants and excipients: maltodextrin, vanilla, carrageenan, mono and diglycerides, and lactated monoglycerides. One skilled in the art will appreciate that not all of the ingredients are necessary to create a Choco-Base formulation that is safe and effective.

Omeprazole powder or enteric-coated granules can be used in each formulation. If the enteric-coated granules are used, the coating is either dissolved by the aqueous diluent or inactivated by trituration in the compounding process.

Applicant additionally analyzed the effects of a lansoprazole Choco-Base formulation on gastric pH using a pH meter (Fisher Scientific) in one adult patient versus lansoprazole alone. The patient was first given a 30 mg oral capsule of lansoprazole (Prevacid®), and the patient's gastric pH was measured at 0, 4, 8, 12, and 16 hours post dose. The results are illustrated in FIG. 4.

The ChocoBase product was compounded according to Formulation 1 above, except 300 mg of lansoprazole was used instead of omeprazole. A dose of 30 mg lansoprazole Choco-Base was orally administered at hour 18 post lansoprazole alone. Gastric pH was measured using a pH meter at hours 18, 19, 24, 28, 32, 36, 40, 48, 52, and 56 post lansoprazole alone dose.

Figure 4:
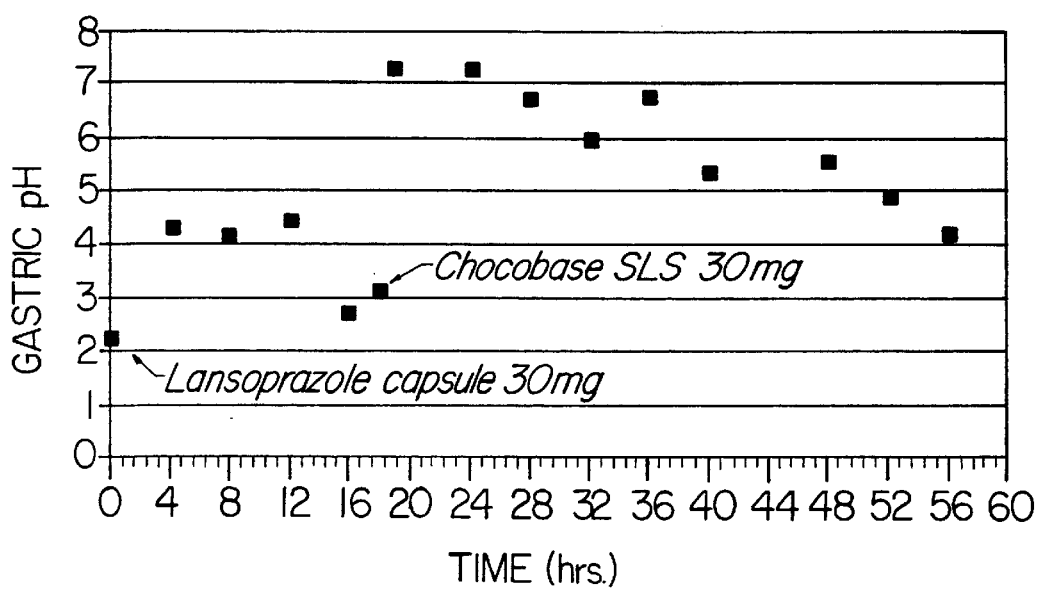
FIG. 4 is a graph illustrating the stomach pH values after the oral administration of both ChocoBase plus lansoprazole and lansoprazole alone.

FIG. 4 illustrates the lansoprazole/cocoa combination resulted in higher pH, at hours 19–56 than lansoprazole alone at hours 4–18. Therefore, the combination of the lansoprazole with chocolate enhanced the pharmacologic activity of the lansoprazole. The results establish that the sodium bicarbonate as well as chocolate flavoring and calcium were all able to stimulate the activation of the proton pumps, perhaps due to the release of gastrin. Proton pump inhibiting agents work by functionally inhibiting the proton pump and effectively block activated proton pumps (primarily those inserted into the secretory canalicular membrane). By further administering the proton pump inhibitor with one of these activators or enhancers, there is a synchronization of activation of the proton pump with the absorption and subsequent parietal cell concentrations of the proton pump inhibitor. As illustrated in FIG. 4, this combination produced a much longer pharmacologic effect than when the proton pump inhibitor was administered alone.

Example VI

Combination Tablet Delivering Bolus And Time-Released Doses of Proton Pump Inhibitor Tablets were compounded using known methods by forming an inner core of 10 mg omeprazole powder mixed with 750 mg sodium bicarbonate, and an outer core of 10 mg omeprazole enteric-coated granules mixed with known binders and excipients. Upon ingestion of the whole tablet, the tablet dissolves and the inner core is dispersed in the stomach where it is absorbed for immediate therapeutic effect. The enteric-coated granules are later absorbed in the duodenum to provide symptomatic relief later in the dosing cycle. This tablet is particularly useful in patients who experience breakthrough gastritis between conventional doses, such as while sleeping or in the early morning hours.

Example VII

Therapeutic Application.

Patients were evaluable if they met the following criteria: had two or more risk factors for SRMD (mechanical ventilation, head injury, severe burn, sepsis, multiple trauma, adult respiratory distress syndrome, major surgery, acute renal failure, multiple operative procedures, coagulotherapy, significant hypertension, acid-base disorder, and hepatic failure), gastric pH of $\leq 4$ prior to study entry, and no concomitant prophylaxis for SRMD.

The omeprazole solution was prepared by mixing 10 ml of 8.4% sodium bicarbonate with the contents of a 20 mg capsule of omeprazole (Merck & Co. Inc., West Point, Pa.) to yield a solution having a final omeprazole concentration of 2 mg/ml.

Nasogastric (ng) tubes were placed in the patients and an omeprazole dosage protocol of buffered 40 mg omeprazole solution (2 mg omeprazole/1 ml $NaHCO_3$–8.4%) followed by 40 mg of the same buffered omeprazole solution in eight hours, then 20 mg of the same buffered omeprazole solution per day, for five days. After each buffered omeprazole solution administration, nasogastric suction was turned off for thirty minutes.

Eleven patients were evaluable. All patients were mechanically ventilated. Two hours after the initial 40 mg dose of buffered omeprazole solution, all patients had an increase in gastric pH to greater than eight as shown in FIG. 1. Ten of the eleven patients maintained a gastric pH of greater than or equal to four when administered 20 mg omeprazole solution. One patient required 40 mg omeprazole solution per day (closed head injury, five total risk factors for SRMD). Two patients were changed to omeprazole solution after having developed clinically significant upper gastrointestinal bleeding while receiving conventional intravenous $H_2$-antagonists. Bleeding subsided in both cases after twenty-four hours. Clinically significant upper gastrointestinal bleeding did not occur in the other nine patients. Overall mortality was 27%, mortality attributable to upper gastrointestinal bleeding was 0%. Pneumonia developed in one patient after initiating omeprazole therapy and was present upon the initiation of omeprazole therapy in another patient. The mean length of prophylaxis was five days.

A pharmacoeconomic analysis revealed a difference in the total cost of care for the prophylaxis of SRMD:

ranitidine (Zantac®) continuous infusion intravenously (150 mg/24 hours)×five days $125.50;

cimetidine (Tagamet®) continuous infusion intravenously (900 mg/24 hours)×five days $109.61;

sucralfate one g slurry four times a day per (ng) tube×five days $73.00; and buffered omeprazole solution regimen per (ng) tube×five days $65.70.

This example illustrates the efficacy of the buffered omeprazole solution of the present invention based on the increase in gastric pH, safety and cost of the buffered omeprazole solution as a method for SRMD prophylaxis.

Example VIII

Effect on pH.

Experiments were carried out in order to determine the effect of the omeprazole solution (2 mg omeprazole/1 ml $NaHCO_3$-8.4%) administration on the accuracy of subsequent pH measurements through a nasogastric tube.

After preparing a total of 40 mg of buffered omeprazole solution, in the manner of Example VII, doses were administered into the stomach, usually through a nasogastric (ng) tube. Nasogastric tubes from nine different institutions were gathered for an evaluation. Artificial gastric fluid (gf) was prepared according to the USP. pH recordings were made in triplicate using a Microcomputer Portable pH meter model 6007 (Jenco Electronics Ltd., Taipei, Taiwan).

First, the terminal portion (tp) of the nasogastric tubes was placed into a glass beaker containing the gastric fluid. A 5 ml aliquot of gastric fluid was aspirated through each tube and the pH recorded; this was called the "pre-omeprazole solution/suspension measurement." Second, the terminal portion (tp) of each of the nasogastric tubes was removed from the beaker of gastric fluid and placed into an empty beaker. Twenty (20) mg of omeprazole solution was delivered through each of the nasogastric tubes and flushed with 10 ml of tap water. The terminal portion (tp) of each of the nasogastric tubes was placed back into the gastric fluid. After a one hour incubation, a 5 ml aliquot of gastric fluid was aspirated through each nasogastric tube and the pH recorded; this was called the "after first dose SOS [Simplified Omeprazole Solution] measurement." Third, after an additional hour had passed, the second step was repeated; this was called the "after second dose SOS [Simplified Omeprazole Solution] measurement." In addition to the pre-omeprazole measurement, the pH of the gastric fluid was checked in triplicate after the second and third steps. A change in the pH measurements of +/−0.3 units was considered significant. The Friedman test was used to compare the results. The Friedman test is a two way analysis of variance which is used when more than two related samples are of interest, as in repeated measurements.

The results of these experiments are outlined in Table 3.

TABLE 3

|  | ng1 | ng2 | ng3 | ng4 | ng5 | ng6 | ng7 | ng8 | ng9 |
|---|---|---|---|---|---|---|---|---|---|
| [1] gf Pre SOS | 1.3 | 1.3 | 1.3 | 1.3 | 1.3 | 1.3 | 1.3 | 1.3 | 1.3 |
| [2] gf p $1^{st}$ dose 1.3↑ check of gf pH | 1.3 | 1.3 | 1.3 | 1.3 | 1.3 | 1.3 | 1.3 | 1.3 | 1.3 |
| [3] gf p $2^{nd}$ Dose 1.3↑ check of gf pH | 1.3 | 1.3 | 1.4 | 1.4 | 1.4 | 1.3 | 1.4 | 1.3 | 1.3 SOS pH = 9.0 |

Table 3 illustrates the results of the pH measurements that were taken during the course of the experiment. These results illustrate that there were no statistically significant latent effects of omeprazole solution administration (per nasogastric tube) on the accuracy of subsequent pH measurements obtained through the same nasogastric tube.

Example IX

Efficacy of Buffered Omeprazole Solution in Ventilated Patients.

Experiments were performed in order to determine the efficacy, safety, and cost of buffered omeprazole solution in mechanically ventilated critically ill patients who have at least one additional risk factor for stress-related mucosal damage.

Patients: Seventy-five adult, mechanically ventilated patients with at least one additional risk factor for stress-related mucosal damage.

Interventions: Patients received 20 ml omeprazole solution (prepared as per Example VII and containing 40 mg of omeprazole) initially, followed by a second 20 ml dose six to eight hours later, then 10 ml (20 mg) daily. Omeprazole solution according to the present invention was administered through a nasogastric tube, followed by 5–10 ml of tap water. The nasogastric tube was clamped for one to two hours after each administration.

Measurements and Main Results: The primary outcome measure was clinically significant gastrointestinal bleeding determined by endoscopic evaluation, nasogastric aspirate examination, or heme-positive coffee ground material that did not clear with lavage and was associated with a five percent decrease in hematocrit. Secondary efficacy measures were gastric pH measured four hours after omeprazole was first administered, mean gastric pH after omeprazole was started, and the lowest gastric pH during omeprazole therapy. Safety-related outcomes included the incidence of adverse events and the incidence of pneumonia. No patient experienced clinically significant upper gastrointestinal bleeding after receiving omeprazole suspension. The four-hour post omeprazole gastric pH was 7.1 (mean), the mean gastric pH after starting omeprazole was 6.8 (mean) and the lowest pH after starting omeprazole was 5.6 (mean). The incidence of pneumonia was twelve percent. No patient in this high-risk population experienced an adverse event or a drug interaction that was attributable to omeprazole.

Conclusions: Omeprazole solution prevented clinically significant upper gastrointestinal bleeding and maintained gastric pH above 5.5 in mechanically ventilated critical care patients without producing toxicity.

Materials and Methods:

The study protocol was approved by the Institutional Review Board for the University of Missouri at Columbia.

Study Population: All adult (>18 years old) patients admitted to the surgical intensive care and burn unit at the University of Missouri Hospital with an intact stomach, a nasogastric tube in place, and an anticipated intensive care unit stay of at least forty-eight hours were considered for inclusion in the study. To be included patients also had to have a gastric pH of <4, had to be mechanically ventilated and have one of the following additional risk factors for a minimum of twenty-four hours after initiation of omeprazole suspension: head injury with altered level of consciousness, extensive burns (>20% Body Surface Area), acute renal failure, acid-base disorder, multiple trauma, coagulopathy, multiple operative procedures, coma, hypotension for longer than one hour or sepsis (see Table 4). Sepsis was defined as the presence of invasive pathogenic organisms or their toxins in blood or tissues resulting in a systematic response that included two or more of the following: temperature greater than 38° C. or less than 36° C., heart rate greater than 90 beats/minute, respiratory rate greater than 20 breaths/minute (or $_pO_2$ less than 75 mm Hg), and white blood cell count greater than 12,000 or less than 4,000 cells/mm$^3$ or more than 10 percent bands (Bone, *Let's Agree on Terminology: Definitions of Sepsis*, CRIT. CARE MED., 19:27 (1991)). Patients in whom $H_2$-antagonist therapy had failed or who experienced an adverse event while receiving $H_2$-antagonist therapy were also included.

Patients were excluded from the study if they were receiving azole antifungal agents through the nasogastric tube; were likely to swallow blood (e.g., facial and/or sinus fractures, oral lacerations); had severe thrombocytopenia (platelet count less than 30,000 cells/mm$^3$); were receiving enteral feedings through the nasogastric tube; or had a history of vagotomy, pyloroplasty, or gastroplasty. In addition, patients with a gastric pH above four for forty-eight hours after ICU admission (without prophylaxis) were not eligible for participation. Patients who developed bleeding within the digestive tract that was not stress-related mucosal damage (e.g., endoscopically verified variceal bleeding or Mallory-Weiss tears, oral lesions, nasal tears due to placement of the nasogastric tube) were excluded from the efficacy evaluation and categorized as having non-stress-related mucosal bleeding. The reason for this exclusion is the confounding effect of non-stress-related mucosal bleeding on efficacy-related outcomes, such as the use of nasogastric aspirate inspection to define clinically significant upper gastrointestinal bleeding.

Study Drug Administration: Omeprazole solution was prepared immediately before administration by the patient's nurse using the following instructions: empty the contents of one or two 20 mg omeprazole capsule(s) into an empty 10 ml syringe (with 20 gauge needle in place) from which the plunger has been removed. (Omeprazole delayed-release capsules, Merck & Co., Inc., West Point, Pa.); replace the plunger and uncap the needle; withdraw 10 ml of 8.4% sodium bicarbonate solution or 20 ml if 40 mg given (Abbott Laboratories, North Chicago, Ill.), to create a concentration of 2 mg omeprazole per ml of 8.4% sodium bicarbonate; and allow the enteric coated pellets of omeprazole to completely breakdown, 30 minutes (agitation is helpful). The omeprazole in the resultant preparation is partially dissolved and partially suspended. The preparation should have a milky white appearance with fine sediment and should be shaken before administration. The solution was not administered with acidic substances. A high-pressure liquid chromatography study was performed that demonstrated that this preparation of simplified omeprazole suspension maintains>90% potency for seven days at room temperature. This preparation remained free of bacterial and fungal contamination for thirty days when stored at room temperature (See Table 7).

The initial dose of omeprazole solution was 40 mg, followed by a second 40 mg dose six to eight hours later, then a 20 mg daily dose administered at 8:00 AM. Each dose was administered through the nasogastric tube. The nasogastric tube was then flushed with 5–10 ml of tap water and clamped for at least one hour. Omeprazole therapy was continued until there was no longer a need for stress ulcer prophylaxis (usually after the nasogastric tube was removed and the patient was taking water/food by mouth, or after the patient was removed from mechanical ventilation).

Primary Outcome Measures: The primary outcome measure in this study was the rate of clinically significant stress-related mucosal bleeding defined as endoscopic evidence of stress-related mucosal bleeding or bright red blood per nasogastric tube that did not clear after a 5-minute lavage or persistent Gastroccult (SmithKline Diagnostics, Sunnyville, Calif.) positive coffee ground material for four consecutive hours that did not clear with lavage (at least 100 ml) and produced a 5% decrease in hematocrit.

Secondary Outcome Measures: The secondary efficacy measures were gastric pH measured four hours after omeprazole was administered, mean gastric pH after starting omeprazole and lowest gastric pH during omeprazole administration. Gastric pH was measured immediately after aspirating gastric contents through the nasogastric tube. pH paper (pHydrion improved pH papers, Microessential Laboratory, Brooklyn, N.Y.) was used to measure gastric aspirate pH. The pH range of the test strips was 1 to 11, in increments of one pH unit. Gastric pH was measured before the initiation of omeprazole solution therapy, immediately before each dose, and every four hours between doses.

Other secondary outcome measures were incidence of adverse events (including drug interactions) and pneumonia. Any adverse event that developed during the study was recorded. Pneumonia was defined using indicators adapted from the Centers for Disease Prevention and Control definition of nosocomial pneumonia (Garner et al., 1988). According to these criteria, a patient who has pneumonia is one who has rates or dullness to percussion on physical examination of the chest or has a chest radiograph that shows new or progressive infiltrate(s), consolidation, cavitation, or pleural effusion and has at least two of the following present: new purulent sputum or changes in character of the sputum, an organism isolated from blood culture, fever or leukocytosis, or evidence of infection from a protective specimen brush or bronchoalveolar lavage. Patients who met the criteria for pneumonia and were receiving antimicrobial agents for the treatment of pneumonia were included in the pneumonia incidence figure. These criteria were also used as an initial screen before the first dose of study drug was administered to determine if pneumonia was present prior to the start of omeprazole suspension.

Cost of Care Analysis: A pharmacoeconomic evaluation of stress ulcer prophylaxis using omeprazole solution was performed. The evaluation included total drug cost (acquisition and administration), actual costs associated with adverse events (e.g., psychiatry consultation for mental confusion), costs associated with clinically significant upper gastrointestinal bleeding. Total drug cost was calculated by adding the average institutional costs of omeprazole 20 mg capsules, 50 ml sodium bicarbonate vials, and 10 ml syringes with needle; nursing time (drug administration, pH monitoring); pharmacy time (drug preparation); and disposal costs. Costs associated with clinically significant upper gastrointestinal bleeding included endoscopy charges and accompanying consultation fees, procedures required to stop the bleeding (e.g., surgery, hemostatic agents, endoscopic procedures), increased hospital length of stay (as assessed by the attending physician), and cost of drugs used to treat the gastrointestinal bleeding.

Statistical Analysis: The paired t-test (two-tailed) was used to compare gastric pH before and after omeprazole solution administration and to compare gastric pH before omeprazole solution administration with the mean and lowest gastric pH value measured after beginning omeprazole.

Figure 2:
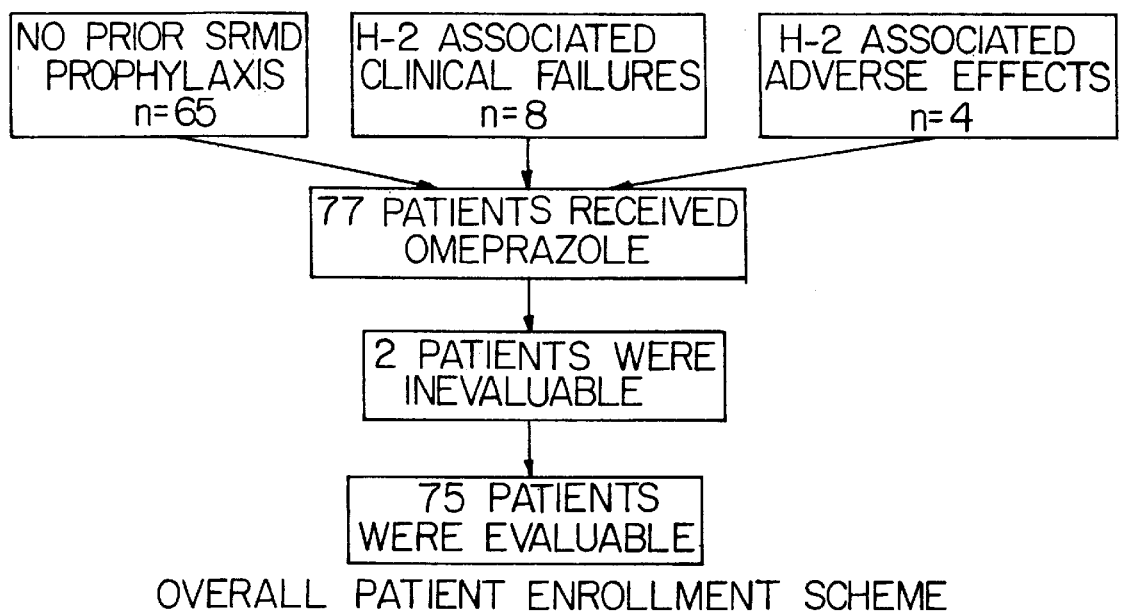
FIG. 2 is a flow chart illustrating a patient enrollment scheme.

Results:

Seventy-seven patients met the inclusion and exclusion criteria and received omeprazole solution (See FIG. 2). Two patients were excluded from the efficacy evaluation because the protocol for omeprazole administration was not followed. In one case, the omeprazole enteric-coated pellets had not completely broken down prior to the administration of the first two doses, which produced an erratic effect on gastric pH. The gastric pH increased to above six as soon as the patient was given a dose of omeprazole solution (in which the enteric coated pellets of omeprazole had been allowed to completely breakdown).

The reason for the second exclusion was that nasogastric suctioning was not turned off after the omeprazole dose was administered. This resulted in a transient effect on gastric pH. The suction was turned off with subsequent omeprazole doses, and control of gastric pH was achieved. Two patients were considered efficacy failures because omeprazole failed to maintain adequate gastric pH control on the standard omeprazole 20 mg/day maintenance dose. When the omeprazole dose was increased to 40 mg/day (40 mg once/day or 20 mg twice/day), gastric pH was maintained above four in both patients. These two patients were included in the safety and efficacy evaluations, including the gastric pH analysis. After the two patients were declared failures, their pH values were no longer followed.

The ages of the remaining seventy-five patients ranged from eighteen to eighty-seven years; forty-two patients were male and thirty-three were female. All patients were mechanically ventilated during the study. Table 4 shows the frequency of risk factors for stress-related bleeding that were exhibited by the patients in this study. The most common risk factors in this population were mechanical ventilation and major surgery. The range of risk factors for any given patient was two to ten, with a mean of 3 (±1) (standard deviation). Five patients enrolled in the study had developed clinically significant bleeding while receiving continuous infusions of ranitidine (150 mg/24 hr) or cimetidine (900 mg/24 hr). In all five cases, the bleeding subsided and the gastric pH rose to above five within thirty-six hours after initiating omeprazole therapy. Three patients were enrolled after having developed two consecutive gastric pH values below three while receiving an $H_2$-antagonist (in the doses outlined above). In all three cases, gastric pH rose to above five within four hours after omeprazole therapy was initiated. Four other patients were enrolled in this study after experiencing confusion (n=2) or thrombocytopenia (n=2) during $H_2$-antigens therapy. Within thirty-six hours of switching therapy, these adverse events resolved.

Stress-related Mucosal Bleeding and Mortality: None of the sixty-five patients who received buffered omeprazole solution as their initial prophylaxis against stress-related mucosal bleeding developed overt or clinically significant upper gastrointestinal bleeding. In four of the five patients who had developed upper gastrointestinal bleeding before study entry, bleeding diminished to the presence of occult blood only (Gastroccult-positive) within eighteen hours of starting omeprazole solution; bleeding stopped in all patients within thirty-six hours. The overall mortality rate in this group of critically ill patients was eleven percent. No death was attributable to upper gastrointestinal bleeding or the use of omeprazole solution.

Figure 3:
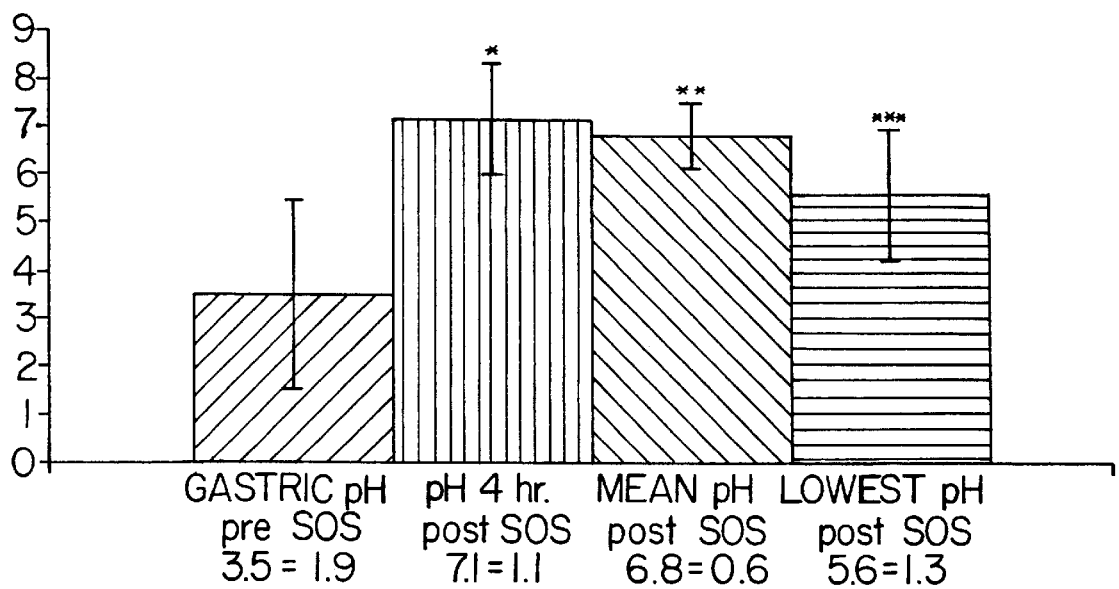
FIG. 3 is a bar graph illustrating gastric pH both pre- and post-administration of omeprazole solution according to the present invention.

Gastric pH: The mean (±standard deviation) pre-omeprazole gastric pH was 3.5±1.9. Within four hours of omeprazole administration, the gastric pH rose to 7.1±1.1 (Sec FIG. 3); this difference was significant (p<0.001). The differences between pre-omeprazole gastric pH and the mean and lowest gastric pH measurements during omeprazole administration (6.8±0.6 and 5.6±1.3, respectively) were also statistically significant (p<0.001).

Safety: Omeprazole solution was well tolerated in this group of critically ill patients. Only one patient with sepsis experienced an adverse event that may have been drug-related thrombocytopenia. However, the platelet count continued to fall after omeprazole was stopped. The platelet count then returned to normal despite reinstitution of omeprazole therapy. Of note, one patient on a jet ventilator continuously expelled all liquids placed in her stomach up and out through her mouth, and thus was unable to continue on omeprazole. No clinically significant drug interactions with omeprazole were noted during the study period. As stated above, metabolic alkalosis is a potential concern in patients receiving sodium bicarbonate. However, the amount of sodium bicarbonate in omeprazole solution was small (12 mEq/10 ml) and no electrolyte abnormalities were found.

Pneumonia: Pneumonia developed in nine (12%) patients receiving omeprazole solution. Pneumonia was present in an additional five patients before the start of omeprazole therapy.

Pharmacoeconomic evaluation: The average length of treatment was nine days. The cost of care data are listed in Tables 5 and 6. The costs of drug acquisition, preparation, and delivery for some of the traditional agents used in the prophylaxis of stress-related upper gastrointestinal bleeding are listed in Table 5. There were no costs to add from toxicity associated with omeprazole solution. Since two of seventy-five patients required 40 mg of omeprazole solution daily to adequately control gastric pH, the acquisition/preparation cost should reflect this. The additional 20 mg of omeprazole with vehicle adds seven cents per day to the cost of care. Therefore, the daily cost of care for omeprazole solution in the prophylaxis of stress-related mucosal bleeding was $12.60 (See Table 6).

Omeprazole solution is a safe and effective therapy for the prevention of clinically significant stress-related mucosal bleeding in critical care patients. The contribution of many risk factors to stress-related mucosal damage has been challenged recently. All of the patients in this study had at least one risk factor that has clearly been associated with stress-related mucosal damage—mechanical ventilation. Previous trials and data from a recently published study show that stress ulcer prophylaxis is of proven benefit in patients at risk and, therefore, it was thought to be unethical to include a placebo group in this study. No clinically significant upper gastrointestinal bleeding occurred during omeprazole solution therapy. Gastric pH was maintained above 4 on omeprazole 20 mg/day in seventy-three of seventy-five patients. No adverse events or drug interaction associated with omeprazole were encountered.

TABLE 4

| Mech Vent | Major Surgery | Multitrauma | Head Injury | Hypotension | Renal Failure | Sepsis | Multiple Operation | Acid/Base | Coma | Liver Failure | Burn |
|---|---|---|---|---|---|---|---|---|---|---|---|
| 75 | 61 | 35 | 16 | 14 | 14 | 14 | 12 | 10 | 4 | 2 | 2 |
| Mech Vent | Major Surgery | Multitrauma | Head Injury | Hypotension | Renal Failure | Sepsis | Multiple Operation | Acid/Base | Coma | Liver Failure | Burn |
| 75 | 61 | 35 | 16 | 14 | 14 | 14 | 12 | 10 | 4 | 2 | 2 |

Risk factors present in patients in this study (n = 75)

TABLE 5

|  |  | Per day |
|---|---|---|
| RANITIDINE (day 1–9) | | |
| Rantidine | 150 mg/24 hr | 6.15 |
| Ancillary Product (1) | Piggyback (60%) | 0.75 |
| Ancillary Product (2) | micro tubing (etc.) | 2.00 |
| Ancillary Product (3) | filter | 0.40 |
| Sterile Prep required | yes | |
| R.N. time ($24/hr) | 20 minutes/day (includes pH monitoring) | 8.00 |
| R.Ph. time, hood maint. | 3 minutes ($40/hr) | 2.00 |
| Pump cost | $29/24 hrs × 50%) | 14.50 |
| TOTAL for 9 days | | 304.20 |
| RANITIDINE Cost per day | | 33.80 |
| CIMETIDINE (day 1–9) | | |
| Cimetidine | 900 mg/24 hr | 3.96 |
| Ancillary Product (1) | Piggyback | 1.25 |
| Ancillary Product (2) | micro tubing (etc.) | 2.00 |
| Ancillary Product (3) | filter | 0.40 |
| Sterile Prep required | yes | |
| R.N. time ($24/hr) | 20 minutes/day (includes pH monitoring) | 8.00 |
| R.Ph. time, hood maint. | 3 minutes ($40/hr) | 2.00 |
| Pump cost | $29/24 hrs × 50%) | 14.50 |
| TOTAL for 9 days | | 288.99 |
| CIMETIDINE Cost per day | | 32.11 |
| SUCRALFATE (day 1–9) | | |
| Sucralfate | 1 g × 4 | 2.40 |
| Ancillary Product (1) | syringe | 0.20 |
| Sterile Prep required | no | |
| R.N. time ($24/hr) | 30 minutes/day (includes pH monitoring) | 12.00 |
| TOTAL for 9 days | | 131.40 |
| SUCRALFATE Cost per day | | 14.60 |

Note:
Does not include the cost of failure and/or adverse effect.
Acquisition, preparation and delivery costs of traditional agents.

TABLE 6

The average length of treatment was 9 days. Cost of care was calculated from these date

|  |  | Per Day | Total |
|---|---|---|---|
| OMEPRAZOLE (day 1) | | | |
| Product acquisition cost | 40 mg load × 2 (5.66/dose) | 11.32 | 11.32 |
| Ancillary product | materials for solution preparation | 0.41 | 0.41 |
| Ancillary product | syringe w/needle | 0.20 | 0.40 |
| Sterile preparation required | no 6 minutes | 2.40 | 4.80 |
| SOS preparation time (R.N.) | 21 minutes/day (includes pH monitoring) | 8.40 | 8.40 |
| R.N. time ($24/hr) | | | |

TABLE 6-continued

The average length of treatment was 9 days. Cost of care was calculated from these date

|  |  | Per Day | Total |
|---|---|---|---|
| OMEPRAZOLE (days 2–9) | | | |
| Product acqusition cost | 20 mg per day | 2.80 | 22.65 |
| Ancillary product | materials for solution preparation | 0.41 | 0.82 |
| Ancillary product | syringe w/needle | 0.20 | 1.60 |
| Sterile preparation required | no 6 minutes | 2.40 | 4.80 |
| SOS preparation time (R.N.) | 18 minutes/day (includes pH monitoring) | 8.40 | 57.60 |
| R.N. time ($24/hr) | | | |
| 2/75 patient require 40 mg simplified omeparzole solution per day (days 2–9) | | | |
| No additional cost for adverse effects or for failure | | | |
| TOTAL | | | |
| Simplified Omerprazole Solution cost per day | | | |

Pharmacoeconomic evaluation of omeprazole cost of care

TABLE 7

| | Time | | | | | |
|---|---|---|---|---|---|---|
|  | Control | 1 hour | 24 hour | 2 day | 7 day | 14 day |
| Conc (mg/ml) | 2.01 | 2.07 | 1.94 | 1.96 | 1.97 | 1.98 |

Stability of Simplified Omeprazole Solution at room temperature (25° C.)
Values are the mean of three samples Example X Bacteriostatic and Fungistatic Effects of Omeprazole Solution The antimicrobial or bacteriostatic effects of the omeprazole solution were analyzed by applicant. An omeprazole solution (2 mg/ml of 8.4% sodium bicarbonate) made according to the present invention was stored at room temperature for four weeks and then was analyzed for fungal and bacterial growth. Following four weeks of storage at room temperature, no bacterial or fungal growth was detected.

An omeprazole solution (2 mg/ml of 8.4% sodium bicarbonate) made in accordance with the present invention was stored at room temperature for twelve weeks and then was analyzed for fungal and bacterial growth. After twelve weeks of incubation at room temperature, no fungal or bacterial growth was detected.

The results of these experiments illustrate the bacteriostatic and fungistatic characteristics of the omeprazole solution of the present invention.

Example XI

A. Bioequivalency Study.

Healthy male and female study participants over the age of 18 will be randomized to receive omeprazole in the following forms:

(A) 20 mg of a liquid formulation of approximately 20 mg omeprazole in 4.8 mEq sodium bicarbonate qs to 10 ml with water;

(B) 20 mg of a liquid formulation of approximately 2 mg omeprazole per 1 ml of 8.4% sodium bicarbonate.

(C) Prilosec® (omeprazole) 20 mg capsule;

(D) Capsule prepared by inserting non-enteric coated omeprazole 20 mg into a #4 empty gelatin capsule (Lilly) uniformly dispersed in 240 mg of sodium bicarbonate powder USP to form an inner capsule. The inner capsule is then inserted into a #00 empty gelatin capsule (Lilly) together with a homogeneous mixture of 600 mg sodium bicarbonate USP and 110 mg pregelatinized starch NF.

After appropriate screening and consent, healthy volunteers will be randomized to receive one of the following four regimens as randomly assigned by Latin Square. Each subject will be crossed to each regimen according to the randomization sequence until all subjects have received all four regimens (with one week separating each regimen).

Regimen A (20 mg omeprazole in 4.8 mEq sodium bicarbonate in 10 ml volume); Regimen B (20 mg omeprazole in 10 ml 8.4% sodium bicarbonate in 10 ml volume); Regimen C (an intact 20 mg omeprazole capsule); Regimen D (Capsule in capsule formulation, see above). For each dose/week, subjects will have an i.v. saline lock placed for blood sampling. For each regimen, blood samples will be taken over 24 hours a total of 16 times (with the last two specimens obtained 12 hours and 24 hours after drug administration).

B. Patient Eligibility

Four healthy females and four healthy males will be consented for the study.

C. Inclusion Criteria

Signed informed consent.

D. Exclusion Criteria

1. Currently taking $H_2$-receptor antagonist, antacid, or sucralfate.
2. Recent (within 7 days) therapy with lansoprazole, omeprazole, or other proton pump inhibitor.
3. Recent (within 7 days) therapy with warfarin.
4. History of variceal bleeding.
5. History of peptic ulcer disease or currently active G.I. bleed.
6. History of vagotomy or pyloroplasty.
7. Patient has received an investigational drug within 30 days.
8. Treatment with ketoconazole or itraconazole.
9. Patient has an allergy to omeprazole.

E. Pharmocokinetic Evaluation and Statistical Analysis

Blood samples will be centrifuged within 2 hours of collection and the plasma will then separated and frozen at −10° C. (or lower) until assayed. Pharmacokinetic variables will include: time to peak concentration, mean peak concentration, AUC (0-t) and (0-infinity). Analysis of variance will be used to detect statistical difference. Bioavailability will be assessed by the 90% confidence interval of the two one-sided tests on the natural logarithm of AUC.

F. HPLC Analysis

Omeprazole and internal standard (H168/24) will be used. Omeprazole and internal standard will be measured by modification of the procedure described by Amantea and Narang. (Amantea Mass., Narang PK. *Improved Procedure for Quantification of Omeprazole and Metabolites Using Reversed-Phased High Performance Liquid Chromotography.* J. CHROMATOGRAPHY 426; 216–222 (1988)). Briefly, 20 ul of omeprazole 2 mg/ml $NaHCO_3$ or Choco-Base omeprazole suspension and 100 ul of the internal standard are vortexed with 150 ul of carbonate buffer (pH=9.8), 5 ml of dichloroethane, 5 ml of hexane, and 980 ul of sterile water. After the sample is centrifuged, the organic layer is extracted and dried over a nitrogen stream. Each pellet is reconstituted with 150 ul of mobile phase (40% methanol, 52% 0.025 phosphate buffer, 8% acetonitrile, pH=7.4). Of the reconstituted sample, 75 ul is injected onto a $C_{18}$ 5 U column equilibrated with the same mobile phase at 1.1 ml/min. Under these conditions, omeprazole is eluted at approximately 5 minutes, and the internal standard at approximately 7.5 minutes. The standard curve is linear over the concentration range 0–3 mg/ml (in previous work with SOS), and the between-day coefficient of variation has been <8% at all concentrations. The typical mean $R^2$ for the standard curve has been 0.98 in prior work with SOS (omeprazole 2 mg/ml $NaHCO_3$ 8.4%).

Applicant expects that the above experiments will demonstrate there is more rapid absorption of formulations (a), (b) and (d) as compared to the enteric coated granules of formulation (c). Additionally, applicant expects that although there will be a difference in the rates of absorption among forms (a) through (d), the extent of absorption (as measured by the area under the curve (AUC)) should be similar among the formulations (a) through (d).

Example XII

Intraveneous Proton Pump Inhibitor in Combination With Oral Parietal Cell Activator Sixteen (16) normal, healthy male and female study subjects over the age of 18 will be randomized to receive pantoprazole as follows:

(a) 40 mg IV over 15 to 30 minutes in combination with a 20 ml oral dose of sodium bicarbonate 8.4%; and (b) 40 mg IV over 15 to 30 minutes in combination with a 20 ml oral dose of water.

The subjects will receive a single dose of (a) or (b) above, and will be crossed-over to (a) and (b) in random fashion. Serum concentrations of pantoprazole versus time after administration data will be collected, as well as gastric pH control as measured with an indwelling pH probe.

Further, similar studies are contemplated wherein chocolate or other parietal cell activator is substituted for the parietal cell activator sodium bicarbonate, and other proton pump inhibiting agents are substituted for pantoprazole. The parietal cell activator can be administered either within about 5 minutes before, during or within about 5 minutes after the IV dose of proton pump inhibitor.

Applicant expects that these studies will demonstrate that significantly less IV proton pump inhibitor is required to achieve therapeutic effect when it is given in combination with an oral parietal cell activator.

Additionally, administration kits of IV proton pump inhibitor and oral parietal cell activator can be packaged in many various forms for ease of administration and to optimize packing and shipping the product. Such kits can be in unit dose or multiple dose form.

Example XIII

Six (6) Month Stability of Omeprazole Suspension.

A suspension was prepared by mixing 8.4% sodium bicarbonate with omeprazole to produce a final concentration of 2 mg/ml to determine the stability of omeprazole solution after 6 months. The resultant preparation was stored in clear glass at room temperature, refrigerated and frozen. Samples were drawn after thorough agitation from the stored preparations at the prescribed times. The samples were then stored at 70° C. Frozen samples remained frozen until they were analyzed. When the collection process was completed, the samples were shipped to a laboratory overnight on dry ice for analysis. Samples were agitated for 30 seconds and sample aliquots were analyzed by HPLC in triplicate according to well known methods. Omeprazole and the internal standard were measured by a modification of the procedure described by Amantea and Narang. (Amantea Mass., Narang PK, *Improved Procedure For Quantitation Of Omeprazole And Metabolites Using Reverse-Phased High-Performance Liquid Chromatography,* J. CHROMATOGRAPHY, 426:216–222 (1988)). Twenty (20) ul of the omeprazole 2 mg/ml $NaHCO_3$ solution and 100 ul of the internal standard solution were vortexed with 150 ul of carbonate buffer (pH=9.8), 5 ml dichloroethane, 5 ml hexane, and 980 ul of sterile water. The sample was centrifuged and the organic layer was extracted and dried over a nitrogen stream. Each pellet was reconstituted with 150 ul of mobile phase (40% methanol, 52% 0.025 phosphate buffer, 8% acetonitrile, pH=7.4). Of the reconstituted sample, 75 ul were injected onto a C185u column equilibrated with the same mobile phase at 1.1 ml/min. Omeprazole was eluted at ~5 min, and the internal standard at ~7.5 min. The standard curve was linear over the concentrated range 0–3 mg/ml, and between-day coefficient of variation was <8% at all concentrations. Mean $R^2$ for the standard curve was 0.980.

The 6 month sample showed stability at greater than 90% of the original concentration of 2 mg/ml. (i.e., 1.88 mg/ml, 1.94 mg/ml, 1.92 mg/ml).

Example XIV
Pharmacokinetic and Pharmacodynamic Study of Duodenal or Jejunal Administration Compared to Nasogastric Administration of Omeprazole Suspension in Patients at Risk for Stress Ulcers Omeprazole suspension administered by the jejunal or duodenal route was compared in a randomized, cross-over fashion with nasogastric administration in patients at risk for stress-related GI bleeding. Eligible for study enrollment were all adult patients (>18 yr.) admitted to the surgical intensive care unit who had recently undergone a major surgical procedure or were posttrauma with an Acute Physiological and Chronic Health Evaluation (APACHE II) score >18. To be included in the study, patients were also required to be mechanically ventilated in addition to having at least one of the following risk factors: head injury with altered level of consciousness; extensive burns (>20% body surface area); acute renal failure; acid-base disorder; multiple traumas; coagulopathy; multiple operative procedures; coma; hypotension for >1 h; or sepsis syndrome. Patients were excluded from participation if they had any of the following characteristics: hypochlorhydria; status of "Do Not Resuscitate"; a history of vagotomy, pyloroplasty, or gastroplasty; an allergy to proton pump inhibitors; active GI bleeding (including variceal bleeding); thrombocytopenia (<30,000/$mm^3$ platelets); active peptic ulcer disease treated within the past year; were likely at risk of swallowing blood (i.e., severe facial trauma, oral lacerations, hemoptysis); currently or during the study receiving ketoconazole or itraconazole or enteral tube feedings; or had received an investigational drug within 30 days, omeprazole or another proton pump inhibitor within 5 days, or warfarin or nonsteroidal anti-inflammatory drugs (NSAIDs), including aspirin, within 24 h. Administration of the study drug was not initiated until the patient had documented gastric pH of <4.0. If 48 h had passed and gastric pH was not <4.0, the patient was excluded from study participation. Patients who were on prior acid reducing therapy for <24 h were allowed to participate after discontinuation of their medication and gastric acidity achieved the study-imposed pH range (gastric pH<4.0). Subjects were not allowed to receive antisecretory agents (e.g., H2RA) during the study. The institutional Review Board for the University of Missouri at Columbia approved the protocol and informed consent was obtained before study enrollment for every subject.

Omeprazole suspension was compounded and stored in amber bottles at 4° C. The omeprazole was prepared by dissolving the contents of two 20-mg capsules (Prilosec®, Astra-Zeneca, Wayne, Pa.) in 20 ml of 8.4% sodium bicarbonate (Abbott Laboratories, North Chicago, Ill.) with gentle shaking to assure adequate mixing. The sodium bicarbonate dissolves the enteric-coated beads leaving "free omeprazole" in the suspension.

A nasogastric tube and needle catheter jejunostomy or duodenal tube was placed before study initiation. Placement of the nasogastric tube was confirmed by x-ray and aspiration of gastric contents for pH confirmation. The jejunostomy and duodenal tubes were placed by standard surgical technique and positioning was confirmed by x-ray. On study day 1, when gastric pH decreased to <4, the patients were randomized to receive a single 40 mg dose of omeprazole suspension by either nasogastric tube or jejunal/duodenal administration. When gastric pH subsequently dropped again to <4 (>24 h in all patients), each patient was crossed-over to the other administration route followed by a single 40 mg dose of omeprazole suspension. All patients received the cross-over dose 72 h after the first day and after the pH had dropped to <4. After omeprazole administration, the nasogastric or duodenal/jejunal tube was flushed with 10 ml of water and clamped for 1–2 h. A Latin square cross-over design was used.

A total of 60 ml of blood was collected in 2.5 ml aliquots over a period of 24 h to establish the absorption and pharmacokinetic parameters of omeprazole as administered by the different enteral routes. Blood samples were obtained immediately before each dose of drug and at 3, 5, 10, 20, 30, 60, 120, 240, 480, 720, 960, and 1440 min after drug administration. All samples were collected in red-top tubes (Vacutainer®, Becton-Dickinson, Franklin Lakes, N.J.), allowed to clot for 30 min at room temperature, and centrifuged for 10 minutes at 1000 g. The resulting sera was removed and immediately frozen at −70° C. until analysis. The study was conducted for approximately 4 days per patient.

Continuous monitoring of gastric acidity (pH) occurred throughout the study period for all patients who received omeprazole suspension. Continuous gastric pH readings were measured with a Zinetics probe (Zinetics Medical, Salt Lake City, Utah).

Omeprazole plasma concentrations were determined by modification of a previously published high-performance liquid chromatography assay. The range of linearity for the assay was 25–1000 ng/ml for serum. The lower limits of detection were 10 ng/ml. Coefficients of variation ($R^2$) for the omeprazole assay over the standard curve concentrations were >0.99 for the entire study. Intra- and interassay coefficients of variation were consistently <8.5% at concentrations included in the linearity range.

The serum omeprazole concentration-time data were analyzed via WinNonlin Software, Standard Edition, Version 1.5 (Scientific Consulting, Cary, N.C.). First dose pharmacokinetic parameters including half-life ($T_{1/2}$), maximum serum-concentration ($C_{max}$), time to maximum serum concentration ($T_{max}$), drug clearance ($Cl_{ss}/F$) were estimated using a noncompartmental extravascular dose model. Area under the serum-concentration time curve (AUC) was determined by trapezoidal rule and was extrapolated to 24 h ($AUC_{0-24}$) and to infinity ($AUC_{0-00}$), using the fitted values of the final plasma concentration time curves.

Demographic, pH, and pharmacokinetic data are reported as the mean±SD as well as the range for respective values when appropriate. The pharmacodynamic relationship between various pharmacokinetic parameters, including clearance (Cl and AUC, were compared to mean pH values obtained for each respective administration route and analyzed by linear regression. Omeprazole concentrations-time data, graphical representation, and statistical analysis were performed with Prism software (GraphPad, Chicago, Ill.). A p value of <0.05 was considered significant for all statistical analyses.

Omeprazole absorption and pharmacokinetic analyses were performed in nine critically ill surgical patients (five men and four women). The administration was well tolerated without any apparent adverse events. The mean (±SD) age, weight, and creatinine clearance of these patients were 33±11 yr (range, 23–56 yr), 78±19 kg (range, 59–124 kg), and 95±24.0 ml/min (range, 35–120 ml/min), respectively. No patients had demonstrated liver disease by either clinical or laboratory evidence of hepatic dysfunction. All nine patients received omeprazole via nasogastric administration, compared with seven and two patients who were also randomized to receive the drug via the jejunal or duodenal route, respectively. Pharmacokinetic parameters for both groups are shown in Table 8. The mean plasma concentration-time curves after 40 mg of omeprazole suspension administered via the nasogastric and jejunal/duodenal routes produced a biphasic curve with the higher peak serum concentrations resulting from the jejunal/duodenal group compared to nasogastric administration (1.833±0.416 µg/m vs. 0.970±0.436 µg/ml, p=0.006). Omeprazole absorption was also significantly slower by comparison of time to maximum concentration ($T_{max}$) when administered by nasogastric tube vs. jejunal/duodenal administration (108.3±42.0 vs. 12.1±7.9 min. p<0.0001). Other mean pharmacokinetic parameters ($t_{1/2}$, $Cl_{ss}$, $AUC_{0-24}$, $AUC_{0-00}$) were not statistically different between the two groups, although there was a trend toward a shorter half-life for patients who received drug via the jejunal/duodenal route.

The mean baseline pH was 1.63±0.89 for the jejunal/duodenal group and 2.12±0.67 for the nasogastric group (p=0.26). Mean intragastric pH values rose to >4 1 h after omeprazole administration and remained >4 for the entire 24-h study period in both groups. When comparing the mean pH data (nasogastric (6.32±1.04) vs. jejunal/duodenal (5.57±1.15), p=0.015) nasogastric administration maintained higher gastric pH values throughout the study with fewer incidences of pH values <4.0 overall.

TABLE 8

Pharmacokinetic Parameters of Omeprazole Suspension

| Variable | Nasogastric (N = 9) | Jejunal/Duodenal (N = 9) | p Value |
|---|---|---|---|
| $AUC_{0-24}$ | 373.3 ± 256.2 | 375.3 ± 340.1 | 0.99 |
| $AUC_{0-00}$ | 415.1 ± 291.8 | 396.7 ± 388.1 | 0.91 |
| $T_{max}$ (min) | 108.3 ± 42.0 | 12.1 ± 7.9 | <0.001 |
| $T_{1/2}$ (min) | 250.7 ± 100.0 | 162.9 ± 138.9 | 0.14 |

TABLE 8-continued

Pharmacokinetic Parameters of Omeprazole Suspension

| Variable | Nasogastric (N = 9) | Jejunal/Duodenal (N = 9) | p Value |
|---|---|---|---|
| Cl/F | 0.144 ± 0.098 | 0.199 ± 0.137 | 0.34 |
| $C_{max}$ (µg/ml) | 0.970 ± 0.436 | 1.833 ± 0.416 | 0.0006 |

Data expressed as mean ± SD.
p < 0.05 considered statistically significant.
$AUC_{0-24}$ = area under the curve from 0 to 24 h;
$AUC_{0-00}$ = Area under the curve from 0 h to infinity;
$T_{max}$ = time to maximum serum concentration;
$T_{1/2}$ = half life;
Cl/F = drug clearance;
$C_{max}$ = maximum serum concentration.

In summary, nasogastric administration of SOS resulted in lower maximum mean±SD serum concentrations compared to jejunal/duodenal dosing (0.970±0.436 vs. 1.833±0.416 µg/ml, p=0.006). SOS absorption was significantly slower when administered via nasogastric tube (108.3±42.0 vs. 12.1±7.9 min,p<0.001). However, all routes of administration resulted in similar SOS area under the serum concentration-time curves ($AUC_{0-00}$) (415.1±291.8 vs. 396.7±388.1 µg h/ml, p=0.91). Mean intragastric pH values remained >4 at 1 h after SOS administration and remained >4 for the entire 24-h study (nasogastric (6.32±1.04) vs. jejunal/duodenal (5.57±1.15), p=0.015), regardless of administration route.

Example XV

Simplified Omeprazole Suspension (SOS) Pharmacokinetic/pharmacodynamic Study in Patients at Risk for Stress-related Mucosal Damage (SRMD).

A. Protocol

Hospitalized patients who were at risk of stress-related mucosal damage (SRMD) were enrolled in this study to evaluate the serum concentration vs. time profile and intragastric pH changes accompanying a single dose of omeprazole 40 mg in 20 mEq sodium bicarbonate suspension. Patients at risk for SRMD were considered eligible and received no prior treatment with omeprazole (within 5 days). Informed Consent was obtained. A nasogastric tube (with a pH probe—incorporated in the tip—GraphProbe ZineticsMedical) was placed in the stomach by standard means. Patients received a dose of SOS (40 mg omeprazole in 20 mL 8.4% sodium bicarbonate) after the gastric pH dropped below 4. Serum concentrations of omeprazole were drawn at the following times:

| 0 min | 3 min | 5 min | 10 min | 15 min | 20 min |
|---|---|---|---|---|---|
| 30 min | 45 min | 1 hr | 2 hrs | 4 hrs | 8 hrs |
| 12 hrs | 24 hrs | | | | |

Gastric pH tracings were made using the ZineticsMedical GraphProbe and the DataLogger from Sandhill scientific.

Serum was ultracentrifuged and stored at −70° C. and sent as a single batch to David Flockhart Md., PhD at Georgetown University Medical Center for HPLC (High Pressure Liquid Chromatography) measurement.

B. Results

The omeprazole plasma concentrations for 17 subjects are provided below in Table Nos. 12, 13, 14, and 15. Below is also a summary the pharmacokinetic and pharmacodynamic findings.

1. Pharmacokinetic

Absorption: Absorption was rapid as indicated by the appearance of omeprazole in serum at <10 minutes in many subjects.

Tmax: The C max (maximum serum concentration) was also rapidly attained when compared to the enteric-coated granules. The C max in most every patient appearing before 1 hour (Tmax).

AUC: The absorption of the omeprazole did not appear to be significantly decreased when compared to omeprazole in the enteric-coated form as measured by Area Under the Curve (AUC).

2. Pharmacodynamic

The gastric pH control appeared to be very rapid and sustained at an unusually high pH for a first dose of omeprazole.

TABLE 9

Omeprazole Concentrations Over time for Patient Nos. 1–5 (µg/ml)

| Time | Patient #1 [Omeprazole] µg/ml plasma | Patient #2 [Omeprazole] µg/ml plasma | Patient #3 [Omeprazole] µg/ml plasma | Patient #4 [Omeprazole] µg/ml plasma | Patient #5 [Omeprazole] µg/ml plasma |
|---|---|---|---|---|---|
| 1 min. | ND | ND | ND | ND | ND |
| 3 min. | ND | 0.155 | 0.149 | 0.02 | ND |
| 5 min. | 0.201 | 0.44 | 0.165 | 0.148 | 0.1 |
| 10 min. | 0.322 | 0.551 | 0.233 | 0.34 | 0.278 |
| 15 min. | ND | 0.587 | 0.261 | 0.44 | 0.413 |
| 20 min. | 0.381 | 1.01 | 0.382 | 0.554 | 0.537 |
| 30 min. | 0.445 | 1.33 | 0.386 | 0.718 | 0.628 |
| 45 min. | 0.658 | 1.46 | 0.445 | 0.89 | 0.68 |
| 1 hr. | 0.755 | 1.24 | 0.501 | 0.893 | 0.749 |
| 2 hrs. | 0.911 | 0.894 | 0.715 | 0.695 | 0.763 |
| 4 hrs. | 0.976 | 0.13 | 0.463 | ND | 0.622 |
| 8 hrs. | 0.78 | 0.05 | 0.305 | ND | 0.319 |
| 12 hrs. | 0.303 | ND | 0.293 | ND | 0.133 |
| 18 hrs. | ND | ND | ND | ND | ND |
| 24 hrs. | 0.218 | ND | 0.215 | ND | ND |

TABLE 10

Omeprazole Concentrations Over time for Patient Nos. 6–10 (µg/ml)

| Time | Patient #6 [Omeprazole] µg/ml plasma | Patient #7 [Omeprazole] µg/ml plasma | Patient #8 [Omeprazole] µg/ml plasma | Patient #9 [Omeprazole] µg/ml plasma | Patient #10 [Omeprazole] µg/ml plasma |
|---|---|---|---|---|---|
| 1 min. | ND | ND | ND | ND | ND |
| 3 min. | ND | ND | ND | ND | 0.041 |
| 5 min. | ND | 0.756 | 0.291 | 0.044 | 0.058 |
| 10 min. | 0.067 | 1.15 | 0.316 | 0.0525 | 0.117 |
| 15 min. | 0.072 | 0.95 | 0.34 | 0.073 | 0.192 |
| 20 min. | 0.05 | ND | 0.44 | 0.096 | 0.213 |
| 30 min. | 0.0925 | ND | 0.66 | 0.152 | 0.237 |
| 45 min. | 0.095 | ND | 0.437 | 0.186 | 0.234 |
| 1 hr. | 0.058 | 0.623 | 0.386 | 0.24 | 0.263 |
| 1 hr. 15 min. | ND | 0.61 | ND | ND | ND |
| 2 hrs. | 0.012 | 0.177 | 0.153 | 0.406 | 0.221 |
| 4 hrs. | ND | 0.107 | 0.044 | 0.865 | 0.391 |
| 8 hrs. | ND | ND | ND | 0.303 | 0.164 |
| 12 hrs. | ND | ND | ND | 0.168 | 0.055 |
| 18 hrs. | ND | ND | ND | ND | ND |
| 24 hrs. | ND | ND | ND | 0.108 | ND |

TABLE 11

Omeprazole Concentrations Over time for Patient Nos. 11–15 (µg/ml)

| Time | Patient #11 [Omeprazole] µg/ml plasma | Patient #12 [Omeprazole] µg/ml plasma | Patient #13 [Omeprazole] µg/ml plasma | Patient #14 [Omeprazole] µg/ml plasma | Patient #15 [Omeprazole] µg/ml plasma |
|---|---|---|---|---|---|
| 1 min. | ND | ND | ND | ND | ND |
| 3 min. | 0.0275 | ND | ND | ND | ND |
| 5 min. | 0.0735 | ND | ND | ND | 0.1075 (or 20 min.) |
| 10 min. | 0.131 | ND | 1.12 | 0.131 | 0.155 |
| 15 min. | 0.154 | ND | 1.08 | 0.161 | 0.176 |
| 17 min. | ND | ND | ND | ND | ND |

TABLE 11-continued

Omeprazole Concentrations Over time for Patient Nos. 11–15 (µg/ml)

| Time | Patient #11 [Omeprazole] µg/ml plasma | Patient #12 [Omeprazole] µg/ml plasma | Patient #13 [Omeprazole] µg/ml plasma | Patient #14 [Omeprazole] µg/ml plasma | Patient #15 [Omeprazole] µg/ml plasma |
|---|---|---|---|---|---|
| 20 min. | 0.177 | 0.012 | 1.04 | 0.187 | ND (or 5 min.) |
| 30 min. | 0.388 | 0.025 | 0.865 | 0.224 | 0.184 |
| 45 min. | 0.526 | 0.046 | 0.841 | 0.269 | 0.196 |
| 1 hr. | 0.486 | 0.077 | 0.896 | 0.276 | 0.155 |
| 2 hrs. | 0.458 | 0.128 | 0.504 | 0.343 | 0.17 |
| 4 hrs. | 0.466 | 0.17 | 0.278 | 0.435 | 0.139 |
| 8 hrs. | 0.232 | 0.148 | 0.145 | 0.204 | ND |
| 12 hrs. | 0.093 | 0.052 | ND | 0.131 | ND |
| 18 hrs. | ND | ND | ND | ND | ND |
| 24 hrs. | ND | ND | ND | ND | ND |

TABLE 12

Omeprazole Concentrations Over time for Patient Nos. 16–17 (µg/ml)

| Time | Patient #16 [Omeprazole] µg/ml plasma | Patient #17 [Omeprazole] µg/ml plasma |
|---|---|---|
| 1 min. | ND | ND |
| 3 min. | ND | ND |
| 5 min. | ND | ND |
| 10 min. | ND | 0.504 |
| 15 min. | ND | 0.6932 |
| 20 min. | ND | 0.765 |
| 30 min. | 0.076 | 0.777 |
| 45 min. | 0.186 | 0.645 |
| 1 hr. | 0.242 | 0.547 |
| 2 hrs. | 0.193 | 0.508 |
| 4 hrs. | ND | ND |
| 8 hrs. | ND | ND |
| 12 hrs. | ND | ND |
| 18 hrs. | ND | ND |
| 24 hrs. | ND | ND |

Example XVI

A Comparison of the Pharmacokinetics and Pharmacodynamics of Omeprazole Delivered Orally with Different Doses of Antacid in Fasted Subjects A. Administration of Test Articles Test articles were administered to each subject according to the following schedule:

Period 1:1 antacid tablet (30 mEq of 1 part sodium bicarbonate to 3 parts calcium carbonate) plus 40 mg omeprazole powder was administered in the fasted state with 60 mL (2 oz.) water.

Period 2: A solution/suspension of omeprazole 40 mg and 20 mEq of sodium bicarbonate (total volume 20 mL in an amber bottle) was administered to the subject. Immediately (within 30 seconds) after administration, the bottle was rinsed with a small amount of water, which was also administered to the subject. The rinse step was repeated and the subject was given a total of 100 mL of water after the administration of the 20 mL of the omeprazole/sodium bicarbonate solution/suspension.

Period 3:1 capsule of Prilosec (40 mg of enteric-coated omeprazole alone) in the fasted state with 120 mL water.

Period 5:1 antacid tablet (30 mEq of 1 part sodium bicarbonate to 1 part calcium carbonate) plus 40 mg omeprazole powder was administered in the fasted state with 120 ml water.

B. Treatment Periods

Only 1 day (Day 1) was required in the clinic. Subjects fasted for at least 10 hours overnight in the clinic prior to initiating pH monitoring; they were allowed water ad libitum until 1 hour prior to dose administration.

Each subject receiving 40 mg of omeprazole powder was administered the drug product by site staff directly onto the dorsal mid-tongue. Immediately thereafter, subjects were administered one or two chewable antacid tablets and began chewing. Each subject continued to chew the tablet(s), while mixing it with the omeprazole powder, carefully avoiding swallowing the powder immediately. One minute after initiating chewing (and after completely swallowing the test articles), each subject drank 60–120 mL of water rising the oral cavity before swallowing. No additional water was allowed until after the 6-hour postdose pH and blood samples were taken. Water was allowed ad libitum. For pharmacokinetic/pharmacodynamic sampling, zero time was the time that chewing is initiated.

C. Inclusion Criteria

Subjects were included in the trial if they met all of the following:

1. Were non-Asian males from 18 to 45 years of age.
2. Were within the ranges of about 20% of ideal body weight.
3. Were in good health on the basis of history, physical examination, and laboratory values.
4. Had not used any form of tobacco (e.g., smoking, chewing) for the last year.
5. Tolerated installation of nasogastric pH probe for at least 5 minutes.
6. Had a basal gastric pH at each trial visit of less than 2.5.

D. Exclusion Criteria

Subjects were excluded from the trial if they met any of the following:

1. Had a significant history odor concurrent gastrointestinal disease or condition, such as GERD, heartburn, reflux esophagitis, peptic ulcer disease (gastric or duodenal), or a family history of peptic ulcer disease, gastric surgery (e.g., vagotomy, pyloroplasty).
2. Had any significant medical history or concurrent illness, such as respiratory, allergic, psychiatric, neurological, renal, hepatic, cardiovascular, metabolic, or endocrine condition, or any other medical condition which the investigator or medical monitor considered sufficiently serious to interfere with the conduct, completion, or results of the trial, or constituted an unacceptable risk to the subject.
3. Had a history of significant drug allergy.
4. Known hypersensitivity to any of the ingredients in the test articles.

5. Had a positive urine test of alcohol or other drugs at any trial visit.
6. Had taken any gastric antisecretory drugs, e.g., H2 antagonists or PPIs, or antacids (including OTC medications) within 14 days prior to Period 1 or during the trial.
7. Had taken xanthine-containing foods or beverages (e.g., coffee, tea, chocolate) within 48 hours of entering the clinic for each trial period.
8. Had ingested grapefruit juice within 7 days of dose administration in any trial period.
9. Had donated blood within 90 days of entering the trial.
10. Had been treated with any investigational drug or therapy, or participated in a clinical trial in the 90 days prior to entering the trial.
11. Had any condition which could have interferes with assessments, posed additional risks in administration of the trial drug to the subject, or precluded completion of the trial, including a history of noncompliance, alcoholism, or drug abuse.
12. Had any laboratory test results deviating from the normal reference ranges established by the local laboratory by more then 20% that the investigator judged to be of possible clinical significance.
13. Evidence of infection with HIV.
14. Known carrier of hepatitis B surface antigen.
15. Known carrier of hepatitis C antibody.

E. Omeprazole Pharmacokinetics

Blood samples (10 mL) for measurement of plasma omeprazole were taken within 30 minutes prior to each dosing, and at 5, 10, 15, 30, 45, 60, 90, 120, 180, 240, 300, and 360 minutes (6 hours) after dosing. These samples were taken at the same time as the gastric pH was being recorded. Plasma omeprazole was measured using a previously validated LC-MSMS assay. Zero time was the time that the subject first chewed a table formulation, swallowed a capsule, or first swallowed a liquid formulation of test article.

F. Test Article Evaluation (Day 1)

On Day 1, after a greater than or less than 10 hour fast, pH recordings of the gastric fluid began in the morning for 1 hour prior to dosing. The pH monitoring continued for 6 hours postdose.

G. Pharmacokinetic Analysis of Omeprazole

The following pharmacokinetic parameters were evaluated:

Omeprazole plasma concentration at each sampling time.
Peak omeprazole plasma concentration ($C_{max}$) and time to peak plasma concentration ($T_{max}$) obtained directly from the data without interpolation.

Terminal elimination rate constant ($k_{el}$) determined from a log-linear regression analysis of the terminal plasma omeprazole concentrations.

Terminal elimination half-life ($t_{1/2}$) calculated as $0.693/k_{el}$.

Area under the omeprazole plasma concentration-time curve from time zero to time "t" ($AUC_{0-t}$), calculated using the trapezodial rule with the plasma concentration at time "t" being the last measurable concentration.

Area under the omeprazole plasma concentration-time curve from time zero to time infinity ($AUC_{0-inf}$), calculated as $AUC_{0-t} + C_t/k_{el}$, where $C_t$ is the last measurable plasma concentration and $k_{el}$ is the terminal elimination rate constant defined above.

H. Onset, Duration, and Magnitude of Effects

On set of action was defined as the earliest time that the value with active treatment was significantly different from the corresponding baseline value. The baseline value for each subject was the mean of values from the twelve 5-minute baseline periods.

Duration of action was the latest time that the value with active treatment was significantly different from the corresponding baseline value.

Magnitude of effect was evaluated for each 5-minute postdosing interval as well as for the postdosing intervals 0–360 minutes.

I. Description

The chewable antacid tablets were produced by Murty Pharmaceuticals, Inc. (518 Codell Drive, Lexington, Ky. 40509-1016) and contained sodium bicarbonate and calcium carbonate, as well as common excipients. Additional formulation(s) for oral administration and At, may contain sodium bicarbonate and/or calcium carbonate either as a tablet or liquid, in addition to omeprazole. USP grade, bulk omeprazole was purchased from Esteve Quimica, S. A. (Barcelona, Spain).

At the trial site, the pharmacy staff mixed omeprazole powder with powdered peppermint flavoring and Equal® Sweetener (containing aspartame) [1 part omeprazole: 2 parts peppermint flavoring:1.8 part Equal®]. For each unit dose, 120 mg (containing 40 mg omeprazole powder) was weighed on an analytic balance within 1–2 hours of dose administration in each time period. This mixture was stored under controlled conditions of humidity and temperature.

J. Results

The omeprazole plasma concentrations for 10 subjects of the study are provided below in Table No. 13.

TABLE 13

| | | Omeprazole Concentrations (ng/ml) | | | | | | | | | | | | |
|---|---|---|---|---|---|---|---|---|---|---|---|---|---|---|
| Sub | | Sampling Times (hour) | | | | | | | | | | | | |
| No. | Period | 0.00 | 0.08 | 0.17 | 0.25 | 0.50 | 0.75 | 1.00 | 1.50 | 2.00 | 3.00 | 4.00 | 5.00 | 6.00 |
| 1 | 1 | 0.00 | 16.4 | 321 | 738 | 968 | 783 | 605 | 357 | 211 | 97.9 | 40.1 | 16.9 | 11.4 |
| 1 | 2 | 0.00 | 79.3 | 312 | 388 | 441 | 454 | 292 | 200 | 128 | 43.4 | 21.0 | 9.44 | 4.32 |
| 1 | 3 | 0.00 | 0.00 | 0.00 | 0.00 | 0.00 | 0.00 | 0.00 | 39.4 | 120 | 366 | 406 | 161 | 109 |
| 1 | 5 | NS | NS | NS | NS | NS | NS | NS | NS | NS | NS | NS | NS | NS |
| 2 | 1 | 0.00 | 6.82 | 234 | 326 | 582 | 875 | 615 | 322 | 220 | 84.2 | 38.1 | 14.7 | 6.39 |
| 2 | 2 | 0.00 | 47.6 | 84.3 | 168 | 1040 | 717 | 484 | 265 | 162 | 67.6 | 26.2 | 11.6 | 4.02 |
| 2 | 3 | 0.00 | 0.00 | 0.00 | 0.00 | 1.57 | 51.3 | 98.6 | 363 | 379 | 429 | 204 | 99.0 | 51.2 |
| 2 | 5 | 0.00 | 22.9 | 315 | 661 | 983 | 797 | 582 | 375 | 306 | 124 | 57.8 | 25.3 | 12.2 |
| 3 | 1 | 0.00 | 203 | 1230 | 1450 | 1000 | 693 | 525 | 306 | 191 | 79.3 | 32.2 | 14.8 | 7.22 |
| 3 | 2 | 0.00 | 20.6 | 302 | 583 | 831 | 740 | 573 | 336 | 203 | 82.0 | 37.6 | 17.6 | 9.38 |
| 3 | 3 | 0.00 | 0.00 | 0.00 | 0.00 | 9.85 | 57.7 | 179 | 683 | 681 | 345 | 158 | 85.4 | 45.9 |

TABLE 13-continued

| | | Omeprazole Concentrations (ng/ml) | | | | | | | | | | | | |
|---|---|---|---|---|---|---|---|---|---|---|---|---|---|---|
| Sub | | Sampling Times (hour) | | | | | | | | | | | | |
| No. | Period | 0.00 | 0.08 | 0.17 | 0.25 | 0.50 | 0.75 | 1.00 | 1.50 | 2.00 | 3.00 | 4.00 | 5.00 | 6.00 |
| 3 | 5 | NS | NS | NS | NS | NS | NS | NS | NS | NS | NS | NS | NS | NS |
| 4 | 1 | 0.00 | 4.57 | 164 | 516 | 1230 | 780 | 495 | 254 | 153 | 55.0 | 20.8 | 8.52 | 3.93 |
| 4 | 2 | 0.00 | 9.53 | 61.6 | 471 | 881 | 566 | 388 | 182 | 107 | 36.5 | 17.9 | 6.17 | 2.63 |
| 4 | 3 | 0.00 | 0.00 | 0.00 | 0.00 | 0.00 | 0.00 | 18.6 | 386 | 454 | 233 | 126 | 81.3 | 51.7 |
| 4 | 5 | 0.00 | 196 | 1240 | 1740 | 994 | 644 | 493 | 305 | 207 | 101 | 44.3 | 18.9 | 8.16 |
| 5 | 1 | 0.00 | 107 | 984 | 1080 | 662 | 409 | 250 | 118 | 60.3 | 19.7 | 7.44 | 2.95 | 1.47 |
| 5 | 2 | 0.00 | 385 | 1400 | 1380 | 693 | 394 | 278 | 144 | 78.1 | 21.8 | 7.20 | 2.16 | BQL |
| 5 | 3 | 0.00 | 0.00 | 0.00 | BQL | 9.25 | 44.0 | 319 | 340 | 252 | 95.5 | 38.8 | 14.6 | 8.16 |
| 5 | 5 | 0.00 | 88.9 | 1210 | 1120 | 677 | 430 | 325 | 173 | 97.8 | 35.1 | 13.4 | 5.04 | 2.06 |
| 6 | 1 | 0.00 | 32.8 | 349 | 552 | 648 | 425 | 267 | 133 | 68.4 | 24.7 | 9.90 | 4.21 | 2.72 |
| 6 | 2 | 0.00 | 13.0 | 68.8 | 101 | 469 | 349 | 241 | 212 | 104 | 31.8 | 9.31 | 3.17 | 1.16 |
| 6 | 3 | 0.00 | 0.00 | 0.00 | 0.00 | 24.0 | 234 | 588 | 351 | 162 | 85.0 | 29.0 | 14.4 | 5.59 |
| 6 | 5 | 0.00 | 5.72 | 26.6 | 50.2 | 190 | 514 | 398 | 177 | 108 | 51.3 | 22.0 | 7.75 | 3.45 |
| 7 | 1 | 0.00 | 5.24 | 97.4 | 269 | 638 | 543 | 431 | 255 | 164 | 63.6 | 29.0 | 11.9 | 5.79 |
| 7 | 2 | 0.00 | 84.0 | 960 | 1170 | 899 | 543 | 433 | 231 | 140 | 54.1 | 24.0 | 12.0 | 5.54 |
| 7 | 3 | 0.00 | 0.00 | 0.00 | 5.42 | 31.0 | 992 | 1110 | 515 | 310 | 115 | 47.0 | 21.8 | 9.32 |
| 7 | 5 | 0.00 | 5.35 | 72.9 | 165 | 363 | 302 | 221 | 268 | 256 | 150 | 71.1 | 29.4 | 11.4 |
| 8 | 1 | 0.00 | 49.9 | 358 | 746 | 1090 | 784 | 609 | 367 | 243 | 104 | 51.1 | 23.1 | 12.1 |
| 8 | 2 | 0.00 | 38.6 | 262 | 1280 | 846 | 563 | 434 | 237 | 148 | 66.9 | 29.5 | 15.7 | 6.15 |
| 8 | 3 | 0.00 | 0.00 | 0.00 | 0.00 | 0.00 | 3.84 | 80.6 | 401 | 313 | 476 | 225 | 108 | 47.1 |
| 8 | 5 | 0.00 | 19.7 | 148 | 582 | 1130 | 822 | 688 | 461 | 264 | 132 | 64.5 | 31.8 | 15.8 |
| 9 | 1 | 0.00 | 16.0 | 139 | 309 | 462 | 355 | 330 | 605 | 317 | 111 | 47.2 | 21.9 | 10.2 |
| 9 | 2 | 0.00 | 277 | 1550 | 1740 | 1150 | 744 | 522 | 305 | 178 | 79.2 | 36.6 | 14.1 | 6.96 |
| 9 | 3 | 0.00 | 0.00 | 0.00 | 0.00 | 0.00 | 1.62 | 47.7 | 551 | 566 | 287 | 153 | 98.0 | 52.5 |
| 9 | 5 | NS | NS | NS | NS | NS | NS | NS | NS | NS | NS | NS | NS | NS |
| 10 | 1 | 0.00 | 15.8 | 130 | 202 | 311 | 233 | 456 | 378 | 187 | 61.6 | 21.2 | 9.90 | 4.20 |
| 10 | 2 | 0.00 | 250 | 1010 | 1100 | 634 | 421 | 310 | 136 | 80.7 | 28.5 | 11.6 | 4.85 | 1.87 |
| 10 | 3 | 0.00 | 0.00 | 0.00 | 0.00 | 5.80 | 114 | 148 | 366 | 390 | 174 | 79.4 | 29.2 | 10.5 |
| 10 | 5 | 0.00 | 103 | 994 | 1190 | 702 | 562 | 353 | 198 | 110 | 36.7 | 14.3 | 5.40 | 2.28 |

NS = No Sample
LOQ = Limit of quantitation: 1.00 ng/ml
BQL = Below quantitation limit

VI. Proton pump inhibitor Compositions and Method for Optimizing the Buffer to be Administered in Combination With a Proton Pump Inhibitor

A. Introduction

The compositions of the present invention are designed to produce rapid release of active drug to the site of delivery (typically the stomach) without the necessity of enteric coatings or delayed released dosage forms, while preventing acid degradation of the drug. Acid labile proton pump inhibiting agents, for example, can be formulated or coadministered with one or more buffers sufficient to protect the proton pump inhibitor in any environment, with the ultimate goal being to deliver a proton pump inhibitor to the stomach (or other environment) either via a liquid, a powder or solid dosage form that produces an immediate release of active drug to the site of delivery such that the proton pump inhibitor is quickly available for absorption. Accordingly, Applicant has found that certain amounts of buffers coadministered or mixed with certain proton pump inhibiting agents prevent acid degradation of the proton pump inhibitor when the buffers produce a pH in the stomach or other site of environment that is equal to the pKa of the proton pump inhibitor plus an amount sufficient to protect the proton pump inhibitor from acids and provide undegraded and bioactive proton pump inhibitor to the blood upon administration (e.g., a final pH of pKa of proton pump inhibitor+ 0.7 log value will reduce the degradation to about 10%). Such buffers should interact with hydrogen ion at rates that exceed the interaction of hydrogen ion with the proton pump inhibitor. Thus, the solubilities of the buffers and proton pump inhibiting agents are important considerations because solubility is a key determinant of the rate of interaction of H+ ion with another compound.

Typically, a proton pump inhibitor formulation of the present invention comprises two primary components: a proton pump inhibitor and an Essential Buffer. An Essential Buffer may include a buffer or combination of buffers that interact with HCl (or other acids in the environment of interest) faster than the proton pump inhibitor interacts with the same acids. When placed in a liquid phase (usually in water), the Essential Buffer produces and maintains a pH of at least the pKa of the proton pump inhibitor. In one embodiment, by raising the pH of the environment to the same of the pKa of the proton pump inhibitor plus about 0.7 log value (or greater), the expected degradation (ionization) can be reduced from about 50% to about 10%. As used herein, the "Essential pH" is the lowest pH of the environment of interest needed to minimize or eliminate the acid-induced degradation of the proton pump inhibitor. The buffering agent(s) employed may raise the pH of the environment to the Essential pH such that 30%, 40% or 50% of the proton pump inhibitor is undegraded, or be present in an amount sufficient to substantially protect (i.e., greater than 50% stability) the proton pump inhibitor.

In another embodiment, the Essential pH is the pKa of the proton pump inhibitor. In a further embodiment, the Essential pH is the sum of the pKa of the proton pump inhibitor plus log 0.7. A log value of about 0.7 is added to the pKa, which represents a decrease of about 5.01187% in stability of the proton pump inhibitor from the pKa plus 1 log value, thus resulting in a stability of approximately 90%, a value widely accepted as desirable in pharmaceutical products. In some cases it may be permissible to accept a value of less than log 0.7.

One aspect of the invention provides that there is also sufficient buffer available to provide the neutralization capacity (Essential Buffer Capacity ("EBC")) to maintain the elevated pH of the environment (usually gastric) throughout the dwell time that the proton pump inhibitor is passed from the environment and into the blood.

B. Essential Buffers

Essential Buffers can be divided into two groups: Primary Essential Buffers and Secondary Essential Buffers. Every formulation is combined with, either directly or indirectly, at least one Primary Essential Buffer. The Primary Essential Buffers, when used alone or in combination, provide buffering activity below the value that leads to tissue irritation or damage and above a lower limit for the Essential pH of the proton pump inhibitor. Secondary Essential Buffers are not required in every formulation but can be combined with Primary Essential Buffers to produce a higher pH and added neutralization capacity for the formulation.

Determining the type and dose of buffer to protect acid labile substituted benzimidazole proton pump inhibiting agents (and other drugs) is useful for efficacious proton pump inhibitor delivery to and action upon parietal cell proton pumps, particularly when the proton pump inhibitor is administered as an immediate release product designed to disintegrate in the stomach rather than a traditional delayed-release product designed to disintegrate beyond the stomach in higher pH environments such as the duodenum. The present compositions and methods employ determinations of the nature of the buffer(s) to be used, as well as calculations to determine Essential pH, buffering capacity, and volume measurements for individual proton pump inhibitor doses based on their respective solubilities and pKa's. Such inventive methods are applicable for determining the type and amount of buffer(s) necessary to protect the proton pump inhibitor in an array of environments (e.g., mouth, esophagus, stomach, duodenum, jejunum, rectal vault, nasogastric tube, or a powder, tablet, capsule, liquid, etc. in storage before administration). Dosage forms in storage may be exposed to various environments, but a typical set of storage conditions includes storage at room temperature (65–80° F.), and minimal or no exposure to heat, cold, light or humidity as is known in the art.

The present method includes all substituted benzimidazole proton pump inhibiting agents, their salts, esters, amides, enantiomers, racemates, prodrugs, derivatives and the like, and is not limited to those proton pump inhibiting agents used to exemplify the following calculations.

The Essential Buffering Capacity ("EBC") is the capacity of a proton pump inhibitor/buffer formulation to resist degradation from its environment. The buffering capacity of a proton pump inhibitor/buffer formulation is primarily derived from components of the formulation that possess the ability to combine with acids (H+ ions) from the environment. The EBC contributes to both acid neutralization (antacid effect) and to maintaining an environmental pH>pKa+0.7 to protect proton pump inhibiting agents from acid degradation throughout the dwell time. The Primary Essential Buffer is designed to maintain the pH of stomach contents (or other environment) at a somewhat constant level within a desired range for a period of time so that the proton pump inhibitor can be absorbed from the gastric or other environment. Accordingly, the Essential Buffer is generally more rapid in its complexation with HCl (or other acid) than the proton pump inhibitor administered so that the Essential Buffer is capable of protecting the proton pump inhibitor.

Any weak base, strong base, or combination thereof may be a suitable Essential Buffer. Essential Buffers include, but are not limited to, electrolytes containing the cations sodium, potassium, calcium, magnesium or bismuth. In addition, amino acids, proteins or protein hydrolysates can serve as Essential Buffers owing to their ability to rapidly neutralize acid. When proton pump inhibiting agents are mixed with the Essential Buffer, the proton pump inhibiting agents may be in the free base form, such as omeprazole or lansoprazole; in the sodium salt form, such as esomeprazole sodium, omeprazole sodium, rabeprazole sodium, pantoprazole sodium, etc.; or in a magnesium salt form such as esomeprazole magnesium or omeprazole magnesium or calcium salt forms; or other salt forms. Essential Buffers provide the Essential Buffering Capacity either alone or in combination with Secondary Essential Buffers.

Tribasic sodium phosphate and sodium carbonate are examples of Secondary Essential Buffers for adjusting the pH of any Primary Essential Buffer. Secondary Essential Buffers may assist the Primary Essential Buffer in producing the desirable $pH_E$ over the dwell time. Secondary Essential Buffers neutralize HCl (or other acids in the environment) similarly to the Primary Essential Buffers; however, they produce pH values too high to be used alone, as they would lead to gastrointestinal mucosal irritation. They are used to increase the pH and provide additional buffering capacity in combination with a Primary Essential Buffer.

Secondary Essential Buffers do not play an important role in protecting the proton pump inhibitor from early acid-induced degradation. Because they do not work as rapidly, they do not play a major role in proton pump inhibitor protection through the dwell time. Other buffers ("Non-Essential Buffers") can be added to the Primary and/or Secondary Essential Buffers to provide a latent antacid effect that extends beyond the antacid effect of Essential Buffers.

Many additional buffers can be used, alone or in combination, to achieve an effective buffering capacity for proton pump inhibiting agents or acid labile drugs. A desirable characteristic of buffers includes rapid neutralization of acid environments to greater than pKa+0.7 for the drug being considered.

Non-limiting examples of Primary and Secondary Essential Buffers are set forth in Tables 8 and 9 below.

TABLE 8

Examples of Primary Essential Buffers

| Essential Buffer | Solubility‡ | pH§ | MW |
|---|---|---|---|
| Sodium bicarbonate | 9.96 g/100 mL | 8–8.4 | 84 |
| Sodium sesquicarbonate | 6.3 g/100 mL | 9.9–10 | 174 |
| Dibasic sodium phosphate | 10 g/100 mL | 8.6–9.3 | 142 |
| Sodium tripolyphosphate | 6 gm/l00 mL | 9.7–10 | 368 |
| Tetrasodium pyrophosphate | 5 g/100 mL | 9.8–10.3 | 266 |
| Sodium citrate | 72 g/100 mL | 5 | 294 |
| Calcium citrate | 10 mg/100 mL | 6.8 | 498 |
| Calcium carbonate | 1.5 mg/100 mL | 6.1–7.1 | 100 |
| Magnesium oxide | 0.62 mg/100 mL | 9.5–10.5 | 40 |
| Sodium gluconate | 60 g/100 mL | 6–8 | 218 |
| Sodium lactate | 40 g/100 mL | 7 | 112 |
| Sodium acetate | 119 g/100 mL | 8.9 | 82 |
| Dipotassium phosphate | 150 g/100 mL | 9.3 | 174 |
| Tetrapotassium pyrophosphate | 185 g/100 mL | 10.4 | 330 |
| Potassium bicarbonate | 36 g/100 mL | 8.2 | 100 |
| Calcium lactate | 6 g/100 mL | 7 | 218 |
| Calcium glycerophosphate | 6 g/100 mL | 7 | 210 |
| Calcium gluconate | 3 g/100 mL | 7.4 | 430 |
| Magnesium lactate | 10 g/100 mL | 5.5–7.5 | 269 |
| Magnesium gluconate | 16 g/100 mL | 7.3 | 414 |

‡solubility is altered by temperature
§pH is altered by concentration and temperature
Note:
hydrated and anhydrous forms are acceptable provided they meet the criteria of a Primary Essential Buffer.

TABLE 9

Examples of Secondary Essential Buffers
These buffers are too caustic to be used alone
but are suitable for addition in low
quantities to the Primary Essential Buffers from Table 8.

| Essential Buffer | Solubility‡ | pH§ | MW |
|---|---|---|---|
| Sodium carbonate | 45.5 g/100 mL | 10.6–11.4 | 106 |
| Potassium carbonate | | 11.5 | 138 |
| Sodium phosphate (tribasic) | 8 g/100 mL | 10.7–12.1 | 163 |
| Calcium hydroxide | 185 mg/100 mL | 12 | 74 |
| Sodium hydroxide | | 11.4–13.2 | 40 |

‡solubility is altered by temperature
§pH is altered by concentration and temperature
Note:
hydrated and anhydrous forms are acceptable provided they meet the criteria of a Secondary Essential Buffer.

Amino acids can also be employed as Primary or Secondary Essential Buffers, the doses of which may be calculated according to the following information.

TABLE 10

| One Letter Symbol | Three Letter Symbol | Amino Acid | MW | pH | Solubility (g/100 g H2O at 25° C. |
|---|---|---|---|---|---|
| A | Ala | Alanine | 89 | 6 | 16.65 |
| C | Cys | Cysteine | 121 | 5.02 | Very |
| D | Asp | Aspartic Acid | 133 | 2.77 | 0.778 |
| E | Glu | Glutamic Acid | 147 | 3.22 | 0.864 |
| F | Phe | Phenylalanine | 165 | 5.48 | 2.965 |
| G | Gly | Glycine | 75 | 5.97 | 24.99 |
| H | His | Histidine | 155 | 7.47 | 4.19 |
| I | Ile | Isoleucine | 133 | 5.94 | 4.117 |
| K | Lys | Lysine | 146 | 9.59 | Very |
| L | Leu | Leucine | 131 | 5.98 | 2.426 |
| M | Met | Methionine | 149 | 5.74 | 3.381 |
| N | Asn | Asparagine | 132 | 5.41 | 3.53 |
| P | Pro | Proline | 115 | 6.30 | 162.3 |
| Q | Gln | Glutamine | 146 | 5.65 | 2.5 |
| R | Arg | Arginine | 174 | 11.15 | 15 |
| S | Ser | Serine | 105 | 5.68 | 5.023 |
| T | Thr | Threonine | 119 | 5.64 | Very |
| V | Val | Valine | 117 | 5.96 | 8.85 |
| W | Trp | Tryptophan | 204 | 5.89 | 1.136 |
| Y | Tyr | Tyrosine | 181 | 5.66 | 0.0453 |

References:
*IUPAC-IUB Commission on Biochemical Nomenclature (CBN), Rules for Naming Synthetic Modifications of Natural Peptides,* (1966); ARCH. BIOCHEM. BIOPHYS. 121:6–8 (1967); BIOCHEM. J. 104:17–19 (1967), corrected 135:9 (1973); BIOCHEMISTRY 6:362–364 (1967); BIOCHIM. BIOPHYS. ACTA 133:1–5 (1967); BULL. SOC. CHIM. BIOL. 49:325–330 (1967) (in French); EUR. J. BIOCHEM. 1:379–381 (1967), corrected 45:3 (1974); Hoppe-Seyler's, Z., PHYSIOL. CHEM. 348:262–265 (1967) (in German); J. BIOL. CHEM. 242 555–557 (1967); MOL. BIOL. 2:466–469 (1968) (in Russian); PURE APPL. CHEM. 31:647–653 (1972); *IUPAC Commission on Nomenclature of Organic Chemistry (CNOC), Nomenclature of Organic Chemistry,* STEREOCHEM. REC. E: (1974), PURE APPL. CHEM. 45:11–30 (1976). See also *Biochemical Nomenclature and Related Documents,* PORTAND PRESS. 2:1–18 (1992).

C. The Essential pH ($pH_E$)

Substituted benzimidazole proton pump inhibiting agents are labile under acidic conditions. Orally administered proton pump inhibiting agents must be protected from the strongly acidic conditions of the stomach, whether acidic from gastric acids or acids introduced through tube feeds or other sources. In general, the higher the pH of the gastric environment, the greater the stability of the proton pump inhibitor, and thus the more time it has to undergo absorption into the blood and reach and act upon the proton pumps of the gastric parietal cells.

As mentioned, the "Essential pH" is the lowest pH of the environment of interest needed to minimize or eliminate the acid-induced degradation of the proton pump inhibitor during the dwell time in the environment. It is generally expressed herein as pH range. Such pH is the pH of the environment in which the proton pump inhibitor/buffer formulation resides. For example, the environment may be a storage container or the stomach. The environment presents a set of conditions to the proton pump inhibitor/buffer, such as temperature, pH, and the presence or absence of water. The dwell time is the time that the proton pump inhibitor dwells in a specific environment, i.e., the GI tract prior to its passage into a different environment, i.e. the blood serum. The shelf-life is another example of a dwell time, in which case, the specific environment may be a container of dry, powdered formulation. As used herein, "Resultant pH" is the pH that is the result of adding a proton pump inhibitor/buffer formulation to an environment of interest. "Formulation pH" is the pH of the proton pump inhibitor/buffer formulation when it is in liquid form.

A proton pump inhibitor dose within its calculated $pH_E$ range is designed to ensure sufficient proton pump inhibitor protection from acid degradation such that delivery to and action upon proton pumps occur. In one desirable embodiment, the $pH_E$ is the sum of the pKa of a given proton pump inhibitor plus about 0.7. The pKa is defined as the pH at which 50% of a chemical is in the ionized form. When the pH of the environment equals the pKa of the proton pump inhibitor, then 50% ionization (degradation) of the proton pump inhibitor occurs. However, by adding the factor of 0.7, this ionization is reduced to 90%.

The Stability Range Factor ("SRF") is the range of pH elevation in which the lower limit is the sum of the pKa of a given proton pump inhibitor+0.7 log, and the upper limit is the pH at which elimination of acid degradation occurs without producing tissue irritation from extreme alkalinity. SRF is calculated based on the desirable shelf-life (or a dwell time), the environmental pH and the amount of acid expected to be encountered, along with a knowledge of the time of exposure expected after the drug is administered and before the drug reaches the blood (i.e., the dwell time).

The upper limit of the SRF is a function of the tolerability of the gastrointestinal mucosa to alkaline substances, which is determined by the Formulation pH and the concentration of alkaline material presented. For practical purposes, pH=10.9 delineates an upper limit of the SRF. It is acknowledged that the amount of buffer is an important aspect of the tissue destructive potential of an alkaline substance. Therefore, the SRF for any given proton pump inhibitor begins at the sum of the pKa of the proton pump inhibitor+ 0.7, and extends upwards to a pH of about 10.9.

The Essential pH used with the SRF establishes a desirable range for the stability to the actions of H+ ion (or other acidic component) on the proton pump inhibitor/buffer formulation.

Sufficient buffering capacity maintains an Essential pH as described below as "Essential Buffering Capacity."

Examples of $pH_E$ calculations with SRF for specific proton pump inhibiting agents are as follows:

$pH_E$ of proton pump inhibitor=pKa of proton pump inhibitor+0.7.

SRF=the range: $pH_E$ to 10.9.
SRF for omeprazole=(pKa omeprazole+0.7) to 10.9=(3.9+ 0.7)=4.6 to 10.9.
SRF for lansoprazole=(pKa lansoprazole+0.7) to 10.9=(4.1+ 0.7)=4.8 to 10.9.
SRF for rabeprazole=(pKa rabeprazole+0.7) to 10.9=(4.9+ 0.7)=5.6 to 10.9.
SRF for pantoprazole=(pKa pantoprazole+0.7) to 10.9=(3+ 0.7)=3.7 to 10.9.

In most instances, the lower end of each of the above ranges is increased by one pH unit to minimize, by a factor of 10, any local effects within the stomach that may produce areas of lower pH that might cause proton pump inhibitor degradation. A value of +1 log value is also supported by the observation that weak bases operate most efficiently at neutralizing acid beginning at +1 log value above the pKa.

For example, one would expect to encounter about 100–150 ml of 0.11 to 0.16N HCl in the adult fasting stomach, which is equivalent to about 12–24 mEq of HCl. Therefore, an equal amount of base will neutralize this acid. If about 12–24 mEq of sodium bicarbonate is employed as the buffer, the resulting pH will be left at the pKa of the conjugate acid of sodium bicarbonate (carbonic acid), which is about 6.14 or greater. This is greater than the lower limit of the $pH_E$ for omeprazole of 4.6. Thus, administering 12–24 mEq of sodium bicarbonate with omeprazole protects greater than 95% of the drug when encountering 12–24 mEq of HCl. Because sodium bicarbonate complexes with HCl at a rate that exceeds the rate of interaction of omeprazole, it is considered a suitable buffer.

It should be noted that depending on age and disease, the amount of acid to be encountered can be significantly more or less than the 12–24 mEq range, but is generally from about 4 mEq to about 30 mEq.

Using magnesium oxide or magnesium hydroxide in an amount of 12 to 24 mEq also provides sufficient neutralizing capacity leaving the pH at approximately 7 (lowered only slightly by the minimal hydrolysis of magnesium). However, magnesium hydroxide is not rapid in onset and care should be taken to ensure that early degradation of the proton pump inhibitor does not occur. Early degradation can be avoided by making a tablet comprising two layers: an inner layer of proton pump inhibitor and sodium bicarbonate, and an outer layer of magnesium hydroxide dried gel or magnesium oxide with suitable disintegrant such that the magnesium oxide would rapidly disintegrate in the stomach. Alternatively, the inner layer can contain the magnesium buffer and the outer layer has the proton pump inhibitor and sodium bicarbonate.

Additionally, micronization of the slower acting buffer can be used to enhance its ability to combine with acid. Calcium carbonate (and many other calcium buffers) is a similar slower acting (compared to sodium bicarbonate) but potent buffer. Therefore, if used, it would be best suited in an outer layer of a tablet formulation with the inner layer comprising a rapid acting buffer with proton pump inhibitor (or vice versa). Alternatively, mixtures of the buffers can be employed for the outer layer. If developing a liquid formulation or a powder for reconstitution, a mixture of a rapid acting buffer and slower acting buffer can be used (e.g., sodium bicarbonate and magnesium oxide, respectively).

Modifications to the formulations may entail adjusting the pH of products with basic or acidic chemicals, including but not limited to, chemicals described throughout this application. Modifications of buffer pH based on the $pH_E$ may or may not be performed in specific instances, depending upon species, age, disease and other variations between patients.

D. pKa and Solubility of Proton Pump Inhibiting Agents

As mentioned above, the pKa of a given proton pump inhibitor indicates inherent stability with respect to acid degradation; the lower the pKa, the more stable the proton pump inhibitor. The solubility of the proton pump inhibitor will also dictate the rate at which the proton pump inhibitor complexes with, and is degraded by, acid. These two physicochemical characteristics (pKa and solubility) of the proton pump inhibitor interact with the physicochemical characteristics of the buffer(s) (pH, buffering capacity and rate of buffering action) in the presence of acid in the environment to determine the degradation of the proton pump inhibitor over time. The less soluble a proton pump inhibitor is in water, the lower the initial degradation when placed in an acidic environment. The following Table 11 elaborates on the time for 50% of drug to be degraded ($t_{1/2}$), pKa and solubility in water of several proton pump inhibiting agents.

TABLE 11

| PH | Pantoprazole | Omeprazole | Lansoprazole | Rabeprazole |
| --- | --- | --- | --- | --- |
|  | sodium |  |  | sodium |
| 1.2 | 4.6 min | 2.8 min | 2.0 min | 1.3 min |
| 5 | 2.8 hr | 1.0 hr | 1.1 hr |  |
| 5.1 | 4.7 hr | 1.4 hr | 1.5 hr | 7.2 minutes |
| 6 | 21 hr | 7.3 hr | 6.4 hr |  |
| 7 | 73 hr | 39 hr | 35 hr |  |
| PKa | 3 | 3.9 | 4.1 | 4.9 |
| Solubility | very soluble | slightly soluble | very slightly soluble | Very soluble |

Kromer W, et al. Differences in pH-Dependent Activation Rates of Substituted Benzimidazoles and Biological in vitro Correlates, PHARMACOLOGY 1998; 56:57–70.

Although pantoprazole sodium, with a pKa of 3, is inherently more stable in an acidic environment than other proton pump inhibiting agents, it is also very soluble in water and thus could undergo 50% degradation in an acidic stomach with a pH of 1.2 in less than 5 minutes. Therefore, it is important for the buffer(s) used with pantoprazole sodium to interact with H+ ion (or other acidic substances) more rapidly than the pantoprazole sodium interacts with such acids and maintain the rapid complexation through the dwell time; otherwise, additional dosing of buffer may be required. The overall pH of the gastric contents should be kept at least at the pKa+0.7 (i.e., 3.7) from the time the proton pump inhibitor in solution comes into contact with the gastric acid continuing throughout the dwell time. Essential Buffers for liquid formulations of pantoprazole sodium include those buffers whose conjugate acids possess a pKa>3.7 and which are very soluble (e.g., potassium bicarbonate and sodium bicarbonate) Oral solid formulations likewise would require buffers whose conjugate acid possesses a pKa>3.7 and rapid complexation potential. Most magnesium, calcium and aluminum salts are not suitable unless the pantoprazole sodium is placed (with or without additional buffer) in an inner portion of a tablet or capsule with such antacids, and surrounded by a rapid acting buffer with a rapid disintegrant. Another formulation method for pantoprazole is to decrease its solubility such as by selecting a less soluble salt form or the non-salt form, pantoprazole.

Rabeprazole sodium is also very soluble in water and could undergo 50% degradation in an acidic stomach with a pH of 1.2 in less than 1.5 minutes. It is not very stable to acid degradation due to its higher pKa of 4.9. A suitable buffer(s) for rabeprazole sodium interacts with H+ ion (or other acidic substances) more rapidly than the rabeprazole sodium interacts with such acids to prevent early degradation, and should possess high neutralizing capacity to enable rabeprazole to survive through the dwell time. Sodium or potassium bicarbonate would be good choices in this instance.

Another option for rabeprazole sodium (as well as any sodium salt of a proton pump inhibitor, which would tend to be more soluble than the base form) is to reduce the solubility of rabeprazole sodium when in aqueous form such as using a less soluble salt form or using the non-salt form. This decreases early degradation because the rabeprazole must first undergo dissolution in water before it is degraded by acid. In this embodiment, the suitable buffer(s) for rabeprazole sodium should possess high neutralizing capacity to enable rabeprazole to survive through the dwell time.

For proton pump inhibiting agents that possess high pKa's, such as rabeprazole sodium, a two-part liquid formulation can be utilized. The liquid part has the proton pump inhibitor and a high pH, but a low mEq buffering capacity. The liquid part is added to a second part that possesses a lower pH but a higher mEq buffering capacity. When these two parts are added together just prior to administration, a formulation with a lower pH and a higher buffering capacity is produced which will neutralize stomach acid but not be too caustic to tissues. Examples of such formulations are provided below.

For highly soluble proton pump inhibiting agents, the formulation may be produced in a solid dosage form such as a tablet, capsule or powder with a buffer(s), which disintegrate and reach solution at a rate that exceeds the proton pump inhibitor and thereby provides the Essential pH for protection of the proton pump inhibitor prior to its dissolution and interaction with the acid in the environment. Further, the tablet or capsule may be formulated to possess an outer portion of buffer and an inner portion comprising proton pump inhibitor, or a blend of proton pump inhibitor and buffer. Additional methods include formulating the buffer in a smaller particle size (e.g., micronized) and the proton pump inhibitor in a larger particle size. This results in the disintegration of the buffer component prior to disintegration of the proton pump inhibitor component. All of these methods of formulation aim to create an environment of stability for the proton pump inhibitor during the dwell time.

The dosage form may affect the suitability of a buffer for use in a formulation. For example, magnesium oxide is a buffer with high buffering capacity but slow onset when formulated as a tablet. However, when formulated as a powder, or a tablet of low compression, or with tablet disintegrants such as pregelatinized starch, it disintegrates more rapidly.

Omeprazole base is only slightly soluble in water and, as such, less of the drug is subject to early and continued degradation. The soluble portion of omeprazole is vulnerable to early degradation in the gastric environment. Dissolution of the remaining insoluble portion is expected to occur within minutes of encountering the water of the gastric secretions. This dissolution time provides some protection against early degradation provided that relatively low volumes of water are used during delivery or in the product formulation. After several minutes in the gastric environment, upon complete dissolution, omeprazole could undergo 50% degradation in less than 3 minutes. Omeprazole is moderately stable owing to its pKa of 3.9. A suitable buffer(s) for omeprazole is rapid acting and possesses at least moderate neutralizing capacity to enable omeprazole to survive through the dwell time.

As used herein, "rapid acting" in the context of a buffer means a buffer that raises the pH of the environment to greater than or equal to the $pH_E$ of a particular proton pump inhibitor in a time sufficient to prevent significant degradation of the proton pump inhibitor. In one embodiment, the rapid acting buffer raises the pH to at least the pKa of the proton pump inhibitor plus 0.7 log value within 10 minutes.

Preferred buffer(s) produce an environment where the Resultant pH of the environment is equal to or greater than the Essential pH such that: (1) the onset of pH change to equal to or greater than the $pH_E+0.7$ begins before the acid-induced degradation of the proton pump inhibitor occurs, and (2) the Resultant pH at or greater than the $pH_E+0.7$ lasts throughout the dwell time, which is typically a minimum of 30 minutes in the case of gastric emptying for an adult. It is desirable that the buffer be rapid acting to minimize early acid-induced degradation. The most rapid acting buffers are water soluble (or soluble in the environment). High solubility, however, is not an absolute necessity as magnesium oxide and calcium carbonate, both only slightly soluble, are capable of significant complexation with gastric acid albeit at a slower rate. If a dry formulation is used, such as a tablet, the particle size of the buffer(s) can be reduced to enhance the dissolution rate while the particle size of the proton pump inhibitor can be increased. Disintegrants can be added to enhance the availability of poorly soluble buffers.

Lansoprazole base is very slightly soluble in water and, as such, less of the drug is subject to early degradation. The soluble portion is vulnerable to early degradation. Dissolution of the remaining insoluble portion is expected to occur within several minutes of encountering the water of the gastric secretions. This dissolution time provides some protection against early degradation provided that relatively low volumes of water are used for delivery or in the product formulation. After several minutes, upon complete dissolution, lansoprazole could undergo 50% degradation in 2 minutes. Lansoprazole is moderately stable owing to its pKa of 4.1. A suitable buffer(s) for lansoprazole should be rapid acting, and should possess moderate to high neutralizing capacity to enable lansoprazole to survive through the dwell time. The pH of the gastric contents (or other environment) should be kept at greater than about 4.8 from the time the proton pump inhibitor in solution comes into contact with the gastric acid continuing throughout the dwell time.

E. Calculating the Acid Neutralizing Capacity of Buffers

The acid neutralizing capacity ("ANC") of soluble buffers may be used to assist in selecting a preferred amount of buffer(s) needed to provide the EBC. The ANC uses both the formula weight (FWt.) and the valence to determine buffering capacity.

An example of an ANC calculation for sodium bicarbonate is as follows:

Sodium Bicarbonate, $Na^+HCO_3^-$, FWt.=84, valence=1.
The conversion equation from equivalent weight to grams is:
(Equivalent Weight ("EW"))(1/1000 mmol)(1 mmol/1 mEq)=grams of $NaCHO_3$
EW=(FWt.)/(valence)=84/1=84 g/mol.
(84 g/mol)(1 mol/1000 mmol)(1 mmol/1 mEq)(4 mEq)=0.34 g $NaHCO_3$ needed for 4 mEq of buffering capacity.

Accordingly, for 10 mEq, one needs 0.840 g $NaHCO_3$, and for 30 mEq, 2.52 gm is required. The range of 4–30 m Eq is used because that is the range of mEq of acid to be encountered in most patients.

The ANCs of other buffers are similarly calculated. ANC determinations are from Drake and Hollander, *Neutralizing Capacity And Cost Effectiveness Of Antacids,* ANN INTERN. MED. 109:215–17 (1981). Generally, the formulations of the present invention need about 4 to about 30 mEq of buffering capacity although higher amounts could be used in some patients.

Sodium bicarbonate in solution possesses a pH>$pH_E$ of omeprazole and rapidly neutralizes acidic environments. As stated above, rapid complexation with HCl is a desirable characteristic of an Essential Buffer. Ideally, but not necessarily required as indicated in formulations that contain a tablet in a tablet, the Essential Buffer complexes with the acid at a faster rate than the proton pump inhibitor it is intended to protect.

In selecting Essential Buffers, a knowledge of buffering capacity is also useful since they possess differing pHs at various concentrations. The magnitude of the resistance of a buffer to pH changes is referred to as buffer capacity (Beta). It has been defined by Koppel, Spiro and Van Slyke as the ratio of the increment of strong acid (or base) to the change in pH brought about by addition of acid. The following formula is used to measure buffer capacity: Buffer capacity= the increment (in gram equivalents per liter) of strong acid added to the buffer solution to produce a pH change (change as measured in absolute terms), or buffer capacity=change in acid/change in pH. Improvements in the formula have been made to improve the precision, and these form the basis for mathematical comparison of buffers for consideration. See Koppel, BioChem, Z. (65) 409–439 (1914), Van Slyke, J. BIOL. CHEM. 52:525 (1922).

Figure 9:
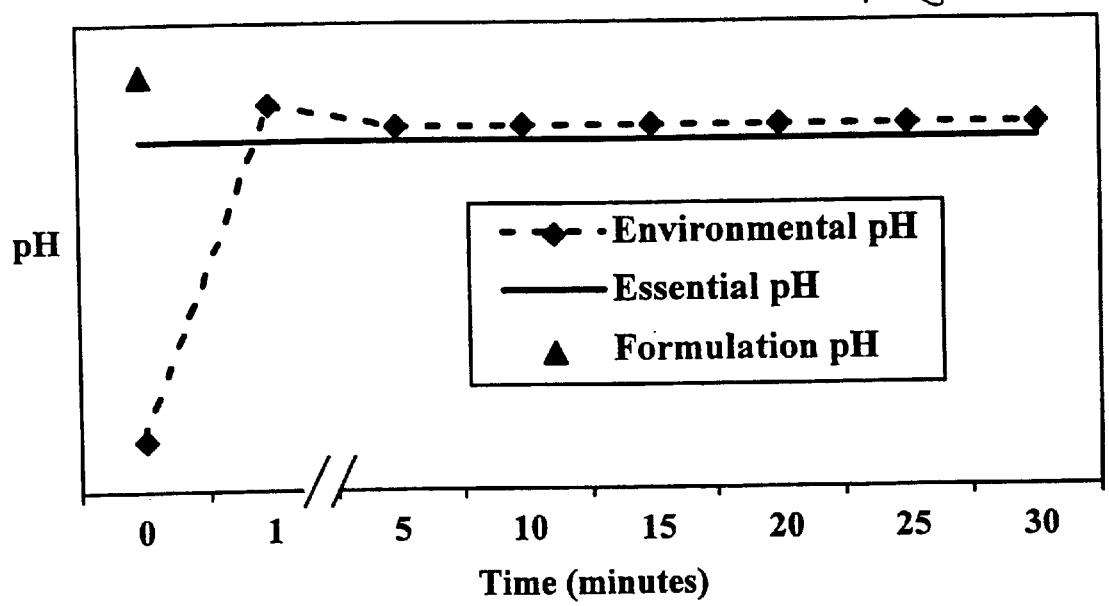
FIG. 9 is a graph illustrating the environmental pH values after administration of the proton pump inhibiting agent/buffer formulation.

When the proton pump inhibitor/buffer formulation is placed in the environment, the proton pump inhibitor is subject to degradation by the acid in that environment. As depicted in FIG. 9, proton pump inhibitor solubility, the pKa of the proton pump inhibitor, and the amount and concentration of acid (H+ ion) encountered in the environment are variables that can be used to determine the appropriate candidate as an Essential Buffer. Early degradation occurs when the soluble portion of the proton pump inhibitor (that portion available for immediate interaction with H+ ion) undergoes hydrolysis by H+ ion. proton pump inhibiting agents differ in their solubility and, therefore, those that are more soluble have a potential for a higher portion of proton pump inhibitor degraded by early interaction with H+ ion. The pKa of the proton pump inhibitor and the pH of the environment of the stomach (or other site of interest) after addition of the proton pump inhibitor/buffer formulation (Resultant pH) can be used to determine the desirable Essential Buffer. By measuring the Resultant pH over time, the pH data versus time can be plotted as seen in FIG. 9. The graph of pH over time can then be used to evaluate various buffers.

Such a graph can be developed for a potential buffer or buffer combination using the Rossett-Rice test (Rosset N E, Marion L: *An In Vitro Evaluation Of The Efficacy Of The More Frequently Used Antacids With Particular Attention To Tablets.* ANTACIDS 26:490–95 (1954), modified with continual addition of simulated gastric fluid. See USP XXIII, *The United States Pharmacopeia*, 23$^{rd}$ Revision, United States Pharmacopeia Convention, Inc. Briefly, the test employs 150 mL of simulated gastric fluid consisting of 2 Gm of sodium chloride and 3.2 Gm of pepsin, which are dissolved in 7 mL of 1N HCl, q.s. to 1000 mL with distilled water. The pH of the simulated gastric fluid is 1.2. A container of 150 mL of this fluid is stirred at 300 rpm±30 rpm with a magnetic stirrer and kept at 37.1° C. A pH electrode is kept in the upper region of the solution. The test buffer or the subject formulation is added to the container to start the evaluation. At 10 minutes, a continuous drip of simulated gastric fluid is added to the test container at a rate of 1.6 ml/min to simulate gastric secretion. Approximately 1.6 mL/min is removed from the test container to keep the volume in the test container constant. The evaluation continues for at least 90 minutes.

This methodology allows for a dynamic evaluation of buffering capacity in a model designed to mimic a fasting human stomach. It has been described in part for use in evaluating antacids by Beneyto J E, et. al., *Evaluation of a New Antacid, Almagate*, ARZNEIM-FORSCH/DRUG RES 1984; 34 (10 A):1350–4; Kerkhof NJ, et al, *pH-Stat Tiration of Aluminum Hydroxide Gel*, J. PHARM. SCI. 1977; 66:1528–32.

Using this method, a pH tracing can be developed for evaluating buffers as well as finished products. In addition, a sample of the test solution can be taken during the experiment to evaluate the extent of proton pump inhibitor degradation at various times. Those buffers with a suitable profile as exemplified in FIG. 9 able to maintain pH greater than or equal to $pH_E$ for 30 minutes or greater, can be considered suitable Essential Buffers. In one embodiment, as depicted in FIG. 9, the pH was recorded over 10 second intervals.

A number of buffers may be applicable for use as Essential Buffers. Therefore, once an Essential Buffer is chosen, the amount necessary to provide the EBC is calculated. As used herein, the EBC is the buffering capacity, or amount of alkaline buffer, included in the dose and calculated to maintain the Essential pH range and thereby protect any substituted benzimidazole proton pump inhibitor in the gastric (or other) environment. In patients requiring continuing proton pump inhibitor administration (e.g. daily), more buffering capacity may be necessary with the first dose or first few doses than with subsequent doses because the proton pump inhibitor may encounter more acid with the initial doses. Subsequent doses will require less buffering capacity because the initial proton pump inhibitor doses will have reduced gastric acid production. The EBC could therefore be reduced in subsequent doses. The product's buffering capacity may be formulated as desired, for instance with respect to patient age, gender or species.

Experimental data from adult human subjects showed an effective EBC range of a first dose of omeprazole to be about 4 to about 20 mEq ("EBC-O range") of sodium bicarbonate, with a range of about 12 to about 25 mEq suitable in most instances. Subsequent doses of omeprazole require less EBC, with a range of about 4 to 15 mEq sodium bicarbonate. In one embodiment, this latter EBC range proved optimal for an omeprazole suspension administered to patients with varying degrees of gastrointestinal transit and acid output, based on a knowledge of basal and maximal acid outputs of 2 and 25 mEq/hour, respectively. These studies have been reported in Phillips J. O. et al., CRIT. CARE MED. 1996; Lasky et al., J. TRAUMA 1998.

Based on the EBC-O range, the above ANC calculation can be employed. Additionally, it is expected to encounter about 100–150 mL of 0.1 N HCl (equating to about 12–24 mEq of acid) in a fasting stomach. Variations in the acid encountered in the environment will affect the Essential Buffering Capacity required. The above EBC ranges relate to adult patients. Children, however, produce less acid per unit time in comparison to adults. Therefore, depending on the patient population, the amount of Essential Buffering Capacity required may be altered.

Numerous references are available to assist the skilled artisan in identifying a suitable buffer companion with a proton pump inhibitor to determine the desirable characteristics stated herein. See, e.g., Holbert, et. al., *A Study of Antacid Buffers: I. The Time Factor in Neutralization of Gastric Acidity*, J. AMER. PHARM. ASSN. 36:149–51 (1947); Lin, et. al., *Evaluation of Buffering Capacity and Acid Neutralizing pH Time Profile of Antacids*, J. FORMOSA MED. ASSN. 97 (10) 704–710 (1998); *Physical Pharmacy*, pp 169–189; *Remington: The Science and Practice of Pharmacy* (2000).

F. The Desirable Volume

The Desirable Volume ("DV") of a proton pump inhibitor dose may affect proton pump inhibitor delivery to and action upon parietal cell proton pumps. The DV of a dose is partly based on the EBC. For liquid formulations, a desirable volume should deliver sufficient buffer to act as an antacid to neutralize a substantial amount of gastric or other acids. For solid formulations such as tablets, a nominal amount of water or other fluid will be consumed to aid in swallowing the tablet. Liquid preparations of the present invention use volumes as small as about 2 ml or in excess of about 60 ml. Volumes smaller than 2 ml and larger than 60 ml are contemplated, and may be used as desired to suit individual patients, such as those of advanced or very young age or of different species. Very large volumes may lead to higher amounts of less soluble proton pump inhibiting agents (e.g., omeprazole, lansoprazole base forms) going into solution, which could result in vulnerability to early degradation.

For instance, volumes smaller than about 2 ml may be used in newborns or premature infants, or in small animals, because of their smaller stomach size. Also, a large DV may be required for doses formulated with dilute buffer concentrations, to achieve the EBC. The relationship between the EBC and DV is in part shown below:

If EBC(mg buffer)=Buffer conc.(mg/ml)×DV(ml), then DV(ml)=EBC(mg)/Buffer conc.(mg/ml).

Alternatively, mEq can be substituted for mg in the formula.

G. Secondary Components of the Formulations

Secondary components are not required but may be used to enhance the pharmacological action or as pharmaceutical aids. Secondary components may include, but are not limited to, parietal cell activators and other ingredients. Parietal cell activators, as discussed above, are compounds that produce an increase in proton pump activity such that proton pumps are relocated from storage sites of the parietal cell, i.e. tubulovesicles, to the site of H+, K+ exchange at the secretory canaliculus. A parietal cell activator may also serve other functions. For example, sodium bicarbonate is an Essential Buffer as well as a parietal cell activator, chocolate is a parietal cell activator and a flavoring agent, and aspartame, which contains phenylalanine, is a sweetener as well as a parietal cell activator.

Parietal cell activators can be divided into four groups: 1) rapid acting buffers that are weak bases, strong bases or combinations thereof that also produce a rapid onset of effect (the pH drops rather suddenly after the buffer is exhausted; these buffers typically cause the pH of the stomach to rise to above 5); 2) amino acids, protein hydrolysates and proteins; 3) calcium containing compounds such as calcium chloride or calcium carbonate; and 4) compositions such as coffee, cocoa, caffeine and peppermint.

The other ingredients comprise secondary components of a formulation that are secondary to the primary components. Other ingredients include, but are not limited to, thickening agents, flavoring agents, sweeteners, antifoaming agents (such as simethicone), preservatives, antibacterial or antimicrobials agents (such as cefazolin, amoxicillin, sulfamethoxazole, sulfisoxazole, erythromycin and other macrolides such as clarithromycin or azithromycin), and Secondary Essential Buffers.

Desirable flavoring agents may be added to the dosage forms, and may or may not need to be buffered to the $pH_E$. Flavoring agents with pH values inherently suitable to the range of $pH_E$ values of proton pump inhibiting agents include, but are not limited to, apple, caramel, meat, chocolate, root beer, maple, cherry, coffee, mint, licorice, nut, butter, butterscotch, and peanut butter flavorings, used alone or in any combination. Similarly, all substances included in the formulation of any proton pump inhibitor product, including but not limited to, activators, antifoaming agents, potentiators, antioxidants, antimicrobial agents, chelators, sweeteners, thickeners, preservatives, or other additives or substances may be buffered to the $pH_E$.

H. Examples Utilizing the Calculations

The $pH_E$, the EBC, and the DV of a proton pump inhibitor dose may affect proton pump inhibitor delivery to, and action upon, parietal cell proton pumps. The following calculations tailor an Essential Buffer dose for any substituted benzimidazole proton pump inhibitor to promote proton pump inhibitor efficacy in an oral administration.

Example 1: To deliver a 20 mg dose of omeprazole (pKa=3.9) in sodium bicarbonate:

Step 1: The $pH_E$ of omeprazole=pKa of omeprazole+0.7= 4.6. The SRF of omeprazole=$pH_E$ to 10.9=4.6 to 10.9. At a Formulation pH of 4.6 to 10.9, the conjugate base of sodium bicarbonate (carbonic acid) has a pKa of 6.14. Therefore, an amount of sodium bicarbonate equivalent to the amount of acid to be encountered would produce a pH of 6.14, which is within the SRF of 4.6 to 10.9. Sodium bicarbonate would make a suitable choice as a buffer.

Step 2: The EBC=4 to 30 mEq buffering capacity equivalent.

Step 3: To determine the amount of sodium bicarbonate to administer with the omeprazole, the ANC for sodium bicarbonate is calculated. The ANC for sodium bicarbonate (MW=84 for 4–30 mEq)=(EW)(1/1000 mmol)(1 mmol/1 mEq)(EBC)
EW=MW/(valence)=84/1=84 g/mol
(84 g/mol)(1 mol/1000 mmol)(1 mmol/1 mEq)(4 to 30 mEq)=0.34 g to 2.52 g Step 4: For liquid formulations, if the DV=20 ml, then DV=Essential Buffer (EB) (mg)/Buffer conc. (mg/ml)
Buffer conc.=EB/DV=340 mg to 2520 mg/20 ml=17 mg/ml to 126 mg/ml.

Therefore, for 20 mg of omeprazole to be adequately buffered in 20 ml of solution, the concentration of sodium bicarbonate should be 17 to 126 mg/ml.

Example 2: To deliver a 20 mg dose of omeprazole (pKa=3.9) in dibasic sodium phosphate:

Step 1: The $pH_E$ of omeprazole=pKa of omeprazole+0.7. The SRF of omeprazole=(3.9+0.7) to 10.9=4.6 to 10.9.

Step 2: The EBC=4 to 30 mEq buffering capacity equivalent.

Step 3: To determine the amount of dibasic sodium phosphate to administer with the omeprazole, the ANC for dibasic sodium phosphate is calculated. The ANC for dibasic sodium phosphate (MW=142)=(EW)(1/1000 mmol)(1 mmol/1 mEq)(EBC).
EW=MW/(valence)=142/2=71 g/mol.
(71 g/mol)(1 mol/1000 mmol)(1 mmol/1 mEq)(4 to 30 mEq)=0.28 g to 2.13 g Step 4: For liquid formulations, if the DV=20 ml, then DV=EB (mg)/Buffer conc. (mg/ml)
Buffer conc.=EB/DV=280 mg to 2130 mg/20 ml=14 mg/ml to 107 mg/ml.

Therefore, for 20 mg of omeprazole to be adequately buffered in 20 ml of solution, the concentration of dibasic sodium phosphate should be 14 to 107 mg/ml. The pka of disodium phosphate is 7.21. Therefore, an amount of disodium phosphate equivalent to the amount of acid to be encountered would produce a pH of approximately 7.2. Thus, disodium phosphate would make a suitable choice as a buffer.

Example 3: To deliver a 30 mg dose of lansoprazole (pKa=4.1) in sodium bicarbonate:

Step 1: The $pH_E$ of lansoprazole=pKa of lansoprazole+0.7. The SRF of lansoprazole=(4.1+0.7) to 10.9=4.8 to 10.9.

Step 2: The EBC=4–30 mEq buffering capacity equivalent.

Step 3: To determine the amount of sodium bicarbonate to administer with the lansoprazole, the ANC for sodium bicarbonate is calculated. The ANC for sodium bicarbonate (MW=84)=(EW)(1/1000 mmol)(1 mmol/1 mEq)(EBC)
EW=MW/valence=84/1 g/mol
(84 g/mol)(1 mol/1000 mmol)(1 mmol/1 mEq)(4 to 30 mEq)=0.34 g to 2.52 g Step 4: For liquid formulations, if the DV=20 ml, then DV=EB (mg)/Buffer conc. (mg/ml)
Buffer conc.=EB/DV=340 mg to 2520 mg/20 ml=17 mg/ml to 126 mg/ml.

Therefore, for 30 mg of lansoprazole to be adequately buffered in 20 ml of solution, the concentration of sodium bicarbonate should be about 17 to about 126 mg/ml.

Example 4: To deliver a 40 mg dose of pantoprazole (pKa=3) in sodium bicarbonate:

Step 1: The $pH_E$ of pantoprazole=pKa of pantoprazole+0.7. The SRF of pantoprazole=(3+0.7) to 10.9=3.7 to 10.9.

Step 2: The EBC=4–30 mEq buffering capacity equivalent.

Step 3: To determine the amount of sodium bicarbonate to administer with the pantoprazole, the ANC for sodium bicarbonate is calculated. The ANC for sodium bicarbonate (MW=84)=(EW)(1/1000 mmol)(1 mmol/1 mEq)(EBC)
EW=MW/(valence)=h 84/1 g/mol
(84 g/mol)(1 mol/1000 mmol)(1 mmol/1 mEq)(4 to 30 mEq)=0.34 g to 2.52 g Step 4: For liquid formulations, if the DV=20 ml, then DV=EB (mg)/Buffer conc. (mg/ml)
Buffer conc.=EB/DV=340 mg to 2520 mg/20 ml=17 mg/ml to 126 mg/ml.

Therefore, for 40 mg of pantoprazole to be adequately buffered in 20 ml, the concentration of sodium bicarbonate should be about 17 to 126 mg/ml.

Example 5: To deliver a 20 mg dose of rabeprazole (pKa=5) in sodium phosphate dibasic:

Step 1: The $pH_E$ of rabeprazole=pKa of rabeprazole+0.7. The SRF of rabeprazole=(4.9+0.7) to 10.9=5.6 to 10.9.

Step 2: The EBC=4–30 mEq buffering capacity equivalent.

Step 3: Therefore, to determine the amount of sodium phosphate dibasic to administer with the rabeprazole, the ANC for potassium sodium dibasic is calculated. The ANC for sodium phosphate dibasic (duohydrate) (MW=174)=(EW)(1/1000 mmol)(1 mmol/1 mEq)(EBC)

EW=MW/valence=178/1 g/mol
(178 g/mol)(1 mol/1000 mmol)(1 mmol/1 mEq)(4 to 20 mEq)=0.712 g to 5.34 g sodium phosphate dibasic.

Step 4: For liquid formulations, if the DV=20 ml, then DV=EB (mg)/Buffer conc. (mg/ml).

Buffer conc.=EB/DV 0.712 g to 2 g/20 ml=35.6 mg/ml to 100 mg/ml. In this case, the solubility of disodium phosphate would limit the amount that could be dissolved in 20 mL. Obviously, this would exceed the solubility of disodium phosphate (sodium phosphate dibasic). Therefore, for 20 mg of rabeprazole to be adequately buffered in 20 ml of solution, the concentration of sodium phosphate dibasic should be about 35.6 mg/ml to 100 mg/ml at a pH range of about 6.9 to 10.9. The pka of disodium phosphate is 7.21. Thus, an amount of disodium phosphate equivalent to the amount of acid to be encountered would produce a pH of approximately 7.2. Accordingly, disodium phosphate would make a suitable choice as a buffer.

It should be noted that the suitability of buffers relates to their use immediately after mixing. In order to enhance the shelf-life, higher pH values would be anticipated within the range of acceptable $pH_E$ for a given proton pump inhibitor. As an example, rabeprazole suspensions containing various buffers were evaluated for color change because degradation of proton pump inhibiting agents results in a color change to brown or black. All buffer suspensions started out white in color. After 2 weeks the following observations were made:

| 20 mg Rabeprazole in Various Buffers Stored Under Refrigerated Conditions As Suspensions | | | |
|---|---|---|---|
| Buffer | Original Color | Color 14 days | pH at 14 days |
| Sodium bicarbonate 800 mg/10 mL | white | brown | 8.3 |
| Disodium phosphate 800 mg/10 mL | white | white | 10.3 |
| Disodium phosphate 700 mg; Trisodium phosphate 100 mg/10 mL | white | white | 10.5 |

Similar calculations may be performed for any substituted benzimidazole proton pump inhibitor and appropriate buffer(s) including, but not limited to, those exemplified above. One skilled in the art will appreciate that the order of the above steps is not critical to the invention. The above calculations may be used for formulations comprising one or more proton pump inhibitor and one or more buffers.

I. Veterinary Formulations

Horses produce stomach acid continuously throughout the day. It is the basal acid secretion from the stomach in the absence of feeding that is responsible for the erosion of the squamous mucosa in the stomach and ulcers. Horses on pasture normally secrete a continuous supply of saliva, which buffers the stomach acid. When horses are being ridden regularly, trained for shows or prepared for sales, they are usually kept in stalls much of the day. Under these conditions, the natural salivary buffering mechanism is disrupted and acid indigestion often results.

Almost 40 to about 100 mEq of buffer capacity should provide approximately 2.5 hours of neutralization for a horse. The usual dose of omeprazole ranges from 0.7 to 1.5 mg/kg/day (doses up to 4 mg/kg/day may be required) and a typical weight for a horse is 500 kg. Similar dosages are expected for rabeprazole and lansoprazole.

Dogs can also suffer from ulcers and their dosage is approximately 1 mg/kg/day. The following formulations are designed for use in horses but smaller amounts can be used in dogs with an EBC of 10 to 20 mEq.

Formulation 5: Veterinary Formulation of Omeprazole
This formulation is particularly well suited for animals rather than humans because the dose of proton pump inhibitor is high. EBC = 75 mEq Essential pH (omeprazole pKa = 3.9 + 0.7 ≧ 4.6)

Proton pump inhibitor:

| | |
|---|---|
| Omeprazole powder | 500 mg (a range of 350 to 700 mg) |

Primary Essential Buffer(s):

| | |
|---|---|
| Sodium bicarbonate | 5 g (59.5 mEq) |
| Dibasic sodium phosphate (anhydrous) | 2 g (14 mEq) |

Optional Secondary Essential Buffer(s):

| | |
|---|---|
| Tribasic sodium phosphate | 200 mg. (1.2 mEq) |

(* Any Secondary Essential Buffer(s) may be added in higher or lower amounts to adjust pH for desired stability and additive antacid or buffering effect.)

Powders of the above compounds are combined as is known in the art to create a homogenous mixture with the addition of a thickener such as guar gum 350 mg, artificial maple flavor powder 100 mg, thaumatin powder 10 mg (to mask the bitterness of omeprazole), and sucrose 25 Gm. Q.s. to 100 mL with distilled water to achieve a final omeprazole concentration of 5 mg/mL. Different volumes of water may be added to achieve omeprazole concentrations ranging from about 0.8 to about 20 mg/mL.

Alternatively, this formulation may be divided into two parts. The dry part may be reconstituted with the liquid part at the time of use.

Formulation 6: Veterinary Formulation of Lansoprazole
Essential pH (lansoprazole pKa=4.1 + 0.7 ≧ 4.8)
EBC = 71.4 mEq Proton pump inhibitor:

| | |
|---|---|
| Lansoprazole powder | 750 mg |

Primary Essential Buffer(s):

| | |
|---|---|
| Sodium bicarbonate | 6 g (71.4 mEq) |

(* Any Secondary Essential Buffer(s) may be added in higher or lower amounts to adjust pH for desired stability and additive antacid or buffering effect.)

Powders of the above compounds are combined as is known in the art to create a homogenous mixture with the addition of a thickener such as xanthan gum 300 mg, artificial peanut butter flavor powder 100 mg, and sucrose 35 Gm. Q.s. to 100 mL with distilled water to achieve a final lansoprazole concentration of 7.5 mg/mL. The suspension should be refrigerated after reconstitution. Different volumes of water may be added to achieve lansoprazole concentrations ranging from 0.8 to 20 mg/mL.

Alternatively, this formulation may divided into two parts. The dry part may be reconstituted with the liquid part at the time of use.

Formulation 7: Veterinary Formulation of Lansoprazole
Essential pH (lansoprazole pKa = 4.1 + 0.7 ≧ 4.8)
EBC = 63.3 mEq Proton pump inhibitor:

| | |
|---|---|
| Lansoprazole powder | 750 mg |

Formulation 7: Veterinary Formulation of Lansoprazole
Essential pH (lansoprazole pKa = 4.1 + 0.7 ≧ 4.8)
EBC = 63.3 mEq Primary Essential Buffer(s)

| | |
|---|---|
| Sodium bicarbonate | 5 g (59.5 mEq) |

Secondary Essential Buffer(s):

| | |
|---|---|
| Sodium carbonate | 400 mg* (3.8 mEq) |

(* Any Secondary Essential Buffer(s) may be added to adjust pH for desired stability and additive antacid or buffering effect.)

Powders of the above compounds are combined as is known in the art to create a homogenous mixture with the addition of a thickener such as hydroxypropyl methyl cellulose 300 mg, artificial maple flavor 100 mg, and sucrose 35 Gm. Q.s. to 100 mL with distilled water to achieve a final lansoprazole concentration of 7.5 mg/mL. Different volumes of water may be added to achieve lansoprazole concentrations ranging from 0.3 to 20 mg/mL.

Alternatively, this formulation may divided into two parts. The dry part may be reconstituted with the liquid part at the time of use.

Formulation 8: Veterinary Formulation of Esomeprazole Magnesium
Essential pH (esomeprazole pKa = 3.9 + 0.7 ≧ 4.6)
EBC = 53.2 mEq Proton pump inhibitor:

| | |
|---|---|
| Esomeprazole magnesium powder | 500 mg |

Primary Essential Buffer(s):

| | |
|---|---|
| Sodium bicarbonate | 5 g (47.6 mEq) |
| Dibasic sodium phosphate | 800 mg (5.6 mEq) |

(* Any Secondary Essential Buffer(s) may be added in higher or lower amounts to adjust pH for desired stability and additive antacid or buffering capacity.)

Powders of the above compounds are combined as is known in the art to create a homogenous mixture with the addition of a thickener such as hydroxypropyl cellulose 300 mg, artificial butterscotch flavor 100 mg, thaumatin powder 5 mg, and sucrose 30 Gm. Q.s. to 100 mL with distilled water to achieve a final esomeprazole concentration of 7.5 mg/mL. Different volumes of water may be added to achieve esomeprazole concentrations ranging from 0.8 to 20 mg/mL.

Formulation 9: Veterinary Formulation of Pantoprazole Sodium or Pantoprazole Base Powder
Essential pH (pantoprazole sodium pKa = 3 + 0.7 ≧ 3.7)
EBC = 53.8 mEq

| | |
|---|---|
| Pantoprazole sodium or pantoprazole powder | 1000 mg |

Primary Essential Buffer(s):

| | |
|---|---|
| Sodium bicarbonate | 4 g (47.6 mEq) |

Secondary Essential Buffer(s):

| | |
|---|---|
| Trisodium phosphate | 1000 mg* (6.2 mEq) |

(*Any Secondary Essential Buffer(s) may be added in higher or lower amounts to adjust pH for desired stability and additive antacid or buffering capacity.)

Powders of the above compounds are combined as is known in the art to create a homogenous mixture with the addition of a thickener such as hydroxypropyl cellulose 300 mg, artificial butterscotch flavor 100 mg, thaumatin powder 5 mg, and sucrose 30 Gm. Q.s. to 100 mL with distilled water to achieve a final pantoprazole concentration of 10 mg/mL. Different volumes of water may be added to achieve esomeprazole concentrations ranging from 0.2 to 20 mg/mL.

Formulation 10: Veterinary Formulation: Buffer Base Without Proton Pump Inhibitor
EBC = 71.4 mEq Primary Essential Buffer:

| | | |
|---|---|---|
| Sodium bicarbonate | 6 g | 71.4 mEq |

Optional Secondary Essential Buffer:

| | |
|---|---|
| Tribasic sodium phosphate | 1000 mg* |

(*Any Secondary Essential Buffer may be added in higher or lower amounts to adjust pH for desired stability and additive antacid or buffering capacity.)

Powders of the above compounds are combined as is known in the art to create a homogenous mixture with the addition of a thickener such as hydroxypropyl cellulose 300 mg, artificial butterscotch flavor 100 mg, thaumatin powder 5 mg, and sucrose 30 Gm. Q.s. to 100 mL with distilled water. A proton pump inhibitor or other acid-labile drug may be added by the compounding pharmacist selected from available proton pump inhibiting agents or acid-labile drugs from powder or enteric-coated oral solid dosage forms. Different volumes of water may be added to achieve proton pump inhibitor concentrations ranging from 0.8 to 20 mg/mL. If other acid labile drugs are employed, the range of concentrations would be as required to deliver the normal dosage in an acceptable volume of 1 mL to 30 mL. The amount of buffer required to protect the drug in question will also determine the minimal feasible volume. This formulation may be in the form of a one-part product (liquid or dry) or a two-part product (liquid and dry), for examples. In the two-part example, the drug to be added to the formulation may be added to the dry formulation and the liquid part may be added at the time of use, or the drug may be added to the liquid portion which would be buffered to a pH above that required for disintegration of enteric-coated drug formulations (typically pH of 6.8 or greater).

For all of the veterinary and human oral dosage forms disclosed herein, sweeteners, parietal cell activators, thickeners, preservatives, and flavoring agents may also be added. Sweeteners include but are not limited to corn syrup, simple syrup, sugar, thaumatin, and aspartame. Thickeners include but are not limited to methylcellulose, xanthan gum, carrageenan, and guar gum. Preservatives may be added to retard spoilage and include but are not limited to sodium benzoate, methylparaben and propylparaben. Flavoring agents in these formulations include but are not limited to apple, caramel, maple, peanut butter, meat, etc.

J. Other Formulations

For all formulations herein, the total amount of Essential Buffer may range from about 4 mEq to about 30 mEq per dose.

Formulation 11: Oral Buffer Complex Without Proton Pump Inhibitor (for general use to protect acid labile drugs) Multidose Composition Primary Essential Buffer:

| | |
|---|---|
| Dibasic sodium phosphate or sodium-bicarbonate | 10 g (range 2 g to 10 g) |

Formulation 11: Oral Buffer Complex Without Proton Pump Inhibitor (for general use to protect acid labile drugs) Multidose Composition

| | |
|---|---|
| Optional Secondary Essential Buffer: | 200 mg |
| Tribasic sodium phosphate or sodium carbonate | |
| Other ingredients: | |
| Sucrose | 26 g |
| Maltodextrin | 2 g |
| Cocoa processed with alkali | 1800 mg |
| Corn syrup solids | 6000 mg |
| Sodium caseinate | 100 mg |
| Soy lecithin | 80 mg |

(*Any Secondary Essential Buffer may be added in higher or lower amounts to adjust pH for desired stability and additive antacid or buffering capacity.)

Thoroughly blend the powder, then store in a container protected from light and moisture, such as in a foil packet. Preservatives may be added to retard spoilage and include but are not limited to sodium benzoate, methylparaben, and propylparaben. Thickeners such as xanthan gum, guar gum, or hydroxymethyl propyl cellulose can be flavoring agents in these formulations include chocolate, caramel, maple, butter pecan and other flavorings as have been outlined previously. Different volumes of water may be added to achieve proton pump inhibitor concentrations ranging from 0.8 to 20 mg/mL.

Weigh out approximately 60 g of the formulation. Add proton pump inhibitor (or other acid-labile drug) typically in the amount equivalent to 10 doses (range 1 dose to 30 doses).

Q.s. to 100 mL with distilled water.

Formulation 12: Oral Buffer Complex Without Proton Pump Inhibitor For General Use to Protect Acid Labile Drugs; Protein Free, Multi-Dose Example Primary Essential Buffer:

| | |
|---|---|
| Sodium bicarbonate | 5 g (range 2 g to 10 g) (59.5 mEq) |

Optional: Secondary Essential Buffer

None*
Other ingredients

| | |
|---|---|
| Sucrose | 26 g |
| Maltodextrin | 2 g |
| Cocoa processed with alkali | 1800 mg |
| Corn syrup solids | 6000 mg |
| Soy lecithin | 80 mg |

Note that cocoa is a parietal cell activator.
(*Any Secondary Essential Buffer may be added in higher or lower amounts to adjust pH for desired stability and additive antacid or buffering capacity.)

Thoroughly blend the powder, then store in a container protected from light and moisture, such as in a foil packet. Weigh out approximately 60 g of the formulation. Add proton pump inhibitor (or other acid-labile drug) typically in the amount equivalent to 10 doses (range=1 dose to 30 doses).

Q.s. to 100 mL with distilled water. Different volumes of water may be added to achieve proton pump inhibitor concentrations ranging from 0.8 to 20 mg/mL.

| Formulation 13: Buffer Complex Without Proton Pump Inhibitor For General Use to Protect Acid Labile Drugs; Protein Free, Lactose Free Multidose Example | |
|---|---|
| Proton pump inhibitor: | |
| None (to be added later, e.g. by compounding pharmacist) Primary Essential Buffer(s): | |
| Sodium bicarbonate Other ingredients: | 8 g (range 2 g to 10 g) |
| Sucrose | 26 g |
| Maltodextrin | 2 g |
| Corn syrup solids | 6000 mg |
| Partially hydrogenated soybean oil | 400 mg |
| Dipotassium phosphate | 300 mg |
| Caramel flavor | 270 mg |
| Soy lecithin | 80 mg |
| Sodium silico aluminate | 20 mg |
| Titanium dioxide | 10 mg |

Thoroughly blend the powder, then store in a container protected from light and moisture, such as in a foil packet.

Optional Secondary Essential Buffer:

Tribasic sodium phosphate 1000 mg

Weigh out approximately 60 g of the formulation. Add proton pump inhibitor (or other acid-labile drug) typically in the amount equivalent to 10 doses (range=1 dose to 30 doses). Q.s. to 100 mL with distilled water. Different volumes of water may be added to achieve proton pump inhibitor concentrations ranging from 0.3 to 20 mg/mL.

| Formulation 14: Buffer Complex Without Proton Pump Inhibitor For General Use to Protect Acid Labile Drugs; Protein Free, Multi-Dose Example | |
|---|---|
| Proton pump inhibitor: | |
| None (to be added later, e.g. by compounding pharmacist) Primary Essential Buffer(s): | |
| Dibasic sodium phosphate Other ingredients: | 8 g (range 2 g to 10 g) |
| Sucrose | 26 g |
| Maltodextrin | 2 g |
| Butterscotch flavor | 270 mg |
| Corn syrup solids | 6000 mg |

Thoroughly blend the powder, then store in a container protected from light and moisture, such as in a foil packet.

Weigh out approximately 60 g of the formulation. Add proton pump inhibitor (or other acid-labile drug) typically in the amount equivalent to 10 doses (range=1 dose to 30 doses). Q.s. to 100 mL with distilled water. Different volumes of water may be added to achieve proton pump inhibitor concentrations ranging from 0.8 to 20 mg/mL.

| Formulation 15: Buffer Complex Without Proton Pump Inhibitor For General Use to Protect Acid Labile Drugs; Protein Free, Multi-Dose Example | |
|---|---|
| Proton pump inhibitor: | |
| None (to be added later, e.g. by compounding pharmacist) | |

| Formulation 15: Buffer Complex Without Proton Pump Inhibitor For General Use to Protect Acid Labile Drugs; Protein Free, Multi-Dose Example | |
|---|---|
| Primary Essential Buffer(s): | |
| Sodium bicarbonate Secondary Essential Buffer(s): | 8 g (range 1 g to 10 g) |
| Trisodium phosphate Other ingredients: | 1.5 g (range 0 g to 5 g) |
| Sucrose | 26 g |
| Maltodextrin | 2 g |
| Butterscotch flavor | 270 mg |
| Corn syrup solids | 6000 mg |

Thoroughly blend the powder, then store in a container protected from light and moisture, such as in a foil packet. Weigh out approximately 60 g of the formulation. Add proton pump inhibitor (or other acid-labile drug) typically in the amount equivalent to 10 doses (range=1 dose to 30 doses). Q.s. to 100 mL with distilled water. Different volumes of water may be added to achieve proton pump inhibitor concentrations ranging from 0.8 to 20 mg/mL.

| Formulation 16: One Phase Lansoprazole 30 mg Tablet Lansoprazole has a pKa of 4.1; thus, the Essential pH = 4.1 + 0.7 ≧ 4.8 Examples of buffers that produce a solution with pH 4.8 or greater and produce the Essential Buffering Capacity include, but are not limited to, sodium bicarbonate, sodium carbonate, dibasic sodium phosphate, and dipotassium phosphate. Enough powder for 11 tablets is weighed out: | |
|---|---|
| Proton pump inhibitor: | |
| Lansoprazole powder Primary Essential Buffer(s): | 330 mg |
| Sodium bicarbonate USP | 5500 mg |
| Dibasic sodium phosphate | 2200 mg |

The resultant powder is thoroughly mixed. Then 720 mg of the homogeneous mixture is poured into a tablet reservoir (½ inch diameter) and pressed through a full motion of the press as is known in the art. The resultant tablet contains:

| | |
|---|---|
| Lansoprazole | 30 mg |
| Sodium bicarbonate USP | 500 mg |
| Disodium hydrogen phosphate | 200 mg |

The tablet contains 6 mEq sodium bicarbonate and 1.4 mEq dibasic sodium phosphate. Variations in this tablet may include a tablet containing all dibasic sodium phosphate or all sodium bicarbonate or other buffers from the Essential Buffers list. The amount of Effective Buffer Capacity per tablet may range from as little as about 4 mEq to as much as about 30 mEq.

Additional tablet disintegrants such as croscarmelose sodium, pregelatinized starch, or providone, and tablet binders such as tapioca, gelatin, or PVP may be added. Further, a film coating may be placed on the tablet to reduce the penetration of light and improve ease of swallowing.

Formulation 17: One Phase Omeprazole 20 mg Tablet
Omeprazole has a pKa of 3.9; thus, the Essential
pH = 3.9 + 0.7 ≧ 4.6
Examples of buffers that are soluble at pH 4.6 or greater
include, but are not limited to, sodium bicarbonate, sodium
carbonate, disodium hydrogen phosphate (dibasic
sodium phosphate), and dipotassium phosphate.
Enough powder for 11 tablets is weighed out:

Proton pump inhibitor:

| | |
|---|---|
| Omeprazole powder USP | 220 mg |
| Primary Essential Buffer(s): | |
| Sodium bicarbonate USP | 6500 mg |
| Magnesium oxide powder | 1650 mg |
| Croscarmelose sodium | 300 mg |

The resultant powder is thoroughly mixed. Then 788 mg of the homogeneous mixture is poured into a tablet reservoir (½ inch diameter) and pressed through a fall motion of the press as is known in the art. The resultant tablet contains:

| | |
|---|---|
| Omeprazole USP | 20 mg |
| Sodium bicarbonate USP | 590 mg |
| Magnesium oxide | 150 mg |
| Croscarmelose sodium | 27.27 mg |

The tablet contains 7 mEq sodium bicarbonate and 3.75 mEq magnesium oxide. The amount of Effective Buffer Capacity may range from as little as about 4 mEq to as much as about 30 mEq. The tablet excipients, tablet binders, and film coating of Formulation 16 may also be added.

Formulation 18: One Phase Omeprazole 40 mg Tablet

Enough powder for 11 tablets is weighed out:
Proton pump inhibitor:

| | | |
|---|---|---|
| Omeprazole powder USP | 440 | mg |
| Primary Essential Buffer(s): | | |
| Sodium bicarbonate USP | 6500 | mg |
| Magnesium oxide | 1650 | mg |
| Pregelatinized starch | 500 | mg |

The resultant powder is thoroughly mixed. Then 826 mg of the homogeneous mixture is poured into a tablet reservoir (½ inch diameter) and pressed through a full motion of the press as is known in the art. The resultant tablet contains:

| | |
|---|---|
| Omeprazole USP | 40 mg |
| Sodium bicarbonate USP | 590 mg |
| Magnesium oxide | 150 mg |
| Pregelatinized starch | 45.45 mg |

The tablet contains 7 mEq sodium bicarbonate and 3.75 mEq magnesium oxide. The amount of Effective Buffer Capacity may range from as little as 4 mEq to as much as 30 mEq. The tablet excipients, tablet binders, and film coating of Formulation 16 may also be added.

Esomeprazole magnesium or other proton pump inhibiting agents which are of low solubility (such as the base forms) may be used in place of omeprazole or lansoprazole in the above formulations. The tablet excipients, tablet binders, and film coatings of Formulation 16 may also be added. In addition, powders of any of the formulations disclosed herein may be manufactured by thoroughly mixing the powders as when making tablets and omitting the pressing of the tablets. The powder is packaged in a suitable container protecting the formulation from air moisture and light such as a foil pack or sachet. When added to a volume of water (e.g. 3 to 20 mL) the formulation may be taken orally or administered down a feeding or NG tube, etc. Flavoring agents such as are outlined in the above formulations may be used, for example, carmel flavor 0.1% w/w. For bitter tasting proton pump inhibiting agents such as pantoprazole, omeprazole, esomperazole and rabeprazole, the use of thaumatin in a quantity of 5 to 10 ppm may be useful in masking the bitterness. Sweeteners such as sucrose or aspartame may also be employed. Tablet disintegrants such as croscarmelose sodium and glidants such as magnesium stearate may additionally be used.

Formulation 19: Omeprazole Powder Formulations (single dose)

Proton pump inhibitor:

| | |
|---|---|
| Omeprazole powder USP | 20 mg or 40 mg |
| (or esomeprazole magnesium). | |
| Primary Essential Buffer(s): | |
| Sodium bicarbonate USP powder (60 micron) | 1000 mg |
| Magnesium oxide USP powder | 500 mg |
| Optional Secondary Essential Buffer(s): | |
| Tribasic sodium phosphate | 200 mg* |
| Other ingredients: | |
| Dextrose | 60 mg |
| Xanthan gum (Rhodigel ultra fine) | 15 mg |
| Thaumatin (Flavor enhancer) | 5 to 10 ppm |

Thoroughly blend the powder, reconstitute all of the powder with 5 ml to 20 ml distilled water and administer the suspension enterally to the patient.

Formulation 20: Unflavored Omeprazole Powder (single dose)

| | |
|---|---|
| Omeprazole powder USP | 20 mg or 40 mg |
| Sodium bicarbonate USP | 1500 mg |
| Parietal cell activator: | |
| Calcium chloride | 200 mg |
| Other ingredients: | |
| Dextrose | 60 mg |
| Xanthan gum (Rhodigel ulta fine) | 15 mg |
| Thaumatin (Flavor enhancer) | 5 to 10 ppm |

Thoroughly blend the powder. Reconstitute all of the powder with 5 mL to 20 mL distilled water and administer the suspension enterally to the patient.

Formulation 21: Flavored Omeprazole Powder (single dose)

| | |
|---|---|
| Omeprazole powder USP | 20 mg |
| Dibasic sodium Phosphate duohydrate | 2000 mg |
| Sodium bicarbonate USP | 840 mg to 1680 mg |
| Sucrose | 2.6 g |
| Maltodextrin | 200 mg |
| Cocoa processed with alkali* | 180 mg |

| Formulation 21: Flavored Omeprazole Powder (single dose) | |
|---|---|
| Corn syrup solids | 600 mg |
| Xanthan gum | 15 mg |
| Aspartame | 15 mg |
| Thaumatin | 2 mg |
| Soy lecithin | 10 mg |

*Parietal cell activator

Thoroughly blend the powder. Reconstitute all of the powder with 10 mL to 20 mL distilled water at the time of use.

| Formulation 22: Unflavored Lansoprazole Powder (single dose) | |
|---|---|
| Lansoprazole powder USP | 15 mg or 50 mg |
| Sodium bicarbonate USP | 400 mg to 1500 mg |

Optionally: Tribasic sodium phosphate to adjust pH for longer stability and enhanced buffering capacity (alternatively other Essential Buffers may be employed)

Thoroughly blend the powder. Reconstitute all of the powder with 5 mL to 20 mL distilled water at the time of use.

| Formulation 23: Flavored Lansoprazole Powder (single dose) | |
|---|---|
| Proton pump inhibitor: | |
| Lansoprazole powder USP | 30 mg |
| Primary Essential Buffer(s): | |
| Dibasic Sodium Phosphate USP or Sodium bicarbonate USP | 1500 mg |
| Sucrose | 26 g |
| Maltodextrin | 2 g |
| Cocoa processed with alkali* | 18 mg |
| Corn syrup solids | 600 mg |
| Soy lecithin | 80 mg |

*Parietal cell activator

Thoroughly blend the powder. Reconstitute all of the powder with 5 mL to 20 mL distilled water at the time of use.

| Formulation 24: Unflavored Rabeprazole Powder (single dose) | |
|---|---|
| Proton pump inhibitor: | |
| Rabeprazole sodium powder USP | 20 mg |
| Primary Essential Buffer(s): | |
| Disodium phosphate duohydrate USP | 2000 mg |
| Optional Secondary Essential Buffer(s) | |
| Tribasic sodium phosphate | 100 mg |

Thoroughly blend the powder and reconstitute with distilled water prior to administration. Optionally, thickeners and flavoring agents may be added as stated throughout this application. The anticipated volume for this powder would be 20 mL per dose. This formulation is designed to enhance stability of rabeprazole through the use of the common ion effect whereby sodium causes a "salting out" of rabeprazole sodium. This causes the rabeprazole sodium to remain insoluble thereby increasing its stability.

| Formulation 25: Unflavored Rabeprazole Powder (single dose) | |
|---|---|
| Proton pump inhibitor: | |
| Rabeprazole sodium powder USP | 20 mg |
| Primary Essential Buffer(s): | |
| Sodium bicarbonate USP | 1200 mg |
| Secondary Essential Buffer(s): | |
| Trisodium phosphate USP | 300 mg |
| Optional Secondary Essential Buffer(s): | |

Sodium hydroxide or Tribasic potassium may be added in higher or lower amounts to adjust pH for desired stability and additive antacid or buffering capacity.

Thoroughly blend the powder and reconstitute with 15 mL distilled water at the time of use.

Alternatively, a two part product may be employed comprising one part of about 5 to about 15 mL distilled water with a low concentration of Secondary Essential Buffer (e.g. trisodium phosphate (100 mg) or sodium hydroxide (50 mg)) used to dissolve an enteric-coated tablet of rabeprazole thereby producing a stable solution/suspension. This highly alkaline suspension containing low neutralization capacity and rabeprazole sodium may then be added with a second part containing the Primary Essential Buffer(s) having significant neutralization capacity. If desired other Secondary Essential Buffer(s) may be included with the Primary Essential Buffers. This formulation is designed to enable the use of the commercially available enteric-coated tablet of rabeprazole as the source of the proton pump inhibitor. This tablet requires disintegration prior to use as a liquid formulation. Part 1 (the low concentration of Secondary Essential Buffer) produces rapid dissolution of the delayed-release tablet as well as prolonged stability of rabeprazole sodium in the liquid form. This enables the preparation to be prepared prior to administration and simply added to the Primary Essential Buffer(s) (part 2) prior to use.

| Formulation 26: Unflavored Rabeprazole Powder (single dose) | |
|---|---|
| Proton pump inhibitor: | |
| Rabeprazole sodium powder USP | 20 mg |
| Primary Essential Buffer(s): | |
| Calcium lactate USP | 700 mg |
| Calcium glycerophosphate | 700 mg |
| Secondary Essential Buffer(s): | |
| Calcium hydroxide USP | 15 mg |

(Other Secondary Essential Buffers with cations of sodium or potassium may be added in higher or lower amounts to adjust pH for desirable stability.)

Thoroughly blend the powder. Reconstitute the powder with a liquid part comprising 10 mL glycerol and 10 mL distilled water at the time of use. Alternatively, the liquid for reconstitution may be only water (e.g. distilled) and contain some of the buffer. The liquid for reconstitution may be supplied as a buffered product (to pH 9–11) for dissolving rabeprazole sodium delayed-release tablets (if used as a source of rabeprazole sodium).

| Formulation 27: Unflavored Esomeprazole Powder (single dose) | |
|---|---|
| Proton pump inhibitor: | |
| Esomeprazole magnesium powder USP | 20 mg |
| Primary Essential Buffer(s): | |
| Calcium lactate USP | 800 mg |
| Calcium glycerophosphate | 800 mg |
| Secondary Essential Buffer(s): | |
| Calcium hydroxide USP | 15 mg |

(Other Secondary Essential Buffers with cations of calcium or magnesium may be added in higher or lower amounts to adjust pH for desirable stability.)

Thoroughly blend the powder. Reconstitute the powder with a liquid part comprising of 10 mL distilled water at the time of use. The liquid for reconstitution may be supplied as a buffered product (to pH 8–11) for dissolving esomeprazole magnesium delayed release granules (if used as a source of esomeprazole magnesium).

| Formulation 28: Omeprazole Two Part Tablet | |
|---|---|
| Two part tablets contain an outer buffer phase and inner buffer/Proton pump inhibitor core. Enough for 6 tablets is weighed out. | |
| Inner Core: | |
| Proton pump inhibitor: | |
| Omeprazole powder USP | 120 mg |
| (or esomeprazole magnesium or omeprazole sodium). | |
| Primary Essential Buffer(s): | |
| Sodium bicarbonate USP | 1200 mg |
| Outer Phase: | |
| Sodium bicarbonate USP | 3960 mg |

(Secondary Essential Buffers such as trisodium phosphate, tripotassium phosphate or sodium carbonate or others may be added to enhance neutralization capacity.)

Thoroughly blend the powders for the inner core, then weigh out approximately 220 mg of the resultant blend and add to a die of ⅜" diameter. The powder mixture is then formulated into small tablets by conventional pharmaceutical procedures. Repeat for five additional tablets, then set these small inner tablets aside.

The outside layer surrounding the proton pump inhibitor tablet serves as a pH-buffering zone. Enough sodium bicarbonate for 6 tablets is weighed out with approximately 280 mg per 15 tablet for a total of 1680 mg sodium bicarbonate USP. Then weigh out approximately 280 mg of the resultant blend and add to a die of ½" diameter. Press through a full motion to compact the powder into a tablet. Place the tablet back into the ½ inch die and then place the smaller ⅜" tablet (inner tablet) on top of the ½" tablet and center it. Add approximately 380 mg sodium bicarbonate to the die on top of the ½" tablet and the ⅜" tablet. Press through a full motion to compact the materials into one tablet. The approximate weight of each tablet is 815 mg to 890 mg containing 20 mg omeprazole. Binders such as tapioca or PVP and disintigrants such as pregelatinized starch may be added. The outer lay may also comprise pharmaceutically acceptable tablet exipients. Optional coatings can also be employed, for example, light film coatings and coatings to repel ultraviolet light as is known in the art.

Magnesium oxide or magnesium hydroxide may be substituted for the sodium bicarbonate outer phase. Enough magnesium oxide for 6 tablets is weighed out with approximately 280 mg per tablet for a total of 1680 mg magnesium oxide USP. Then weigh out approximately 280 mg of the resultant blend and add to a die of ½" diameter. Press through a full motion to compact the powder into a tablet. Place the tablet back into the ½ inch die and then place the smaller ⅜" tablet (inner tablet) on top of the ½" tablet and center it. Add approximately 380 mg magnesium oxide to the die on top of the ½" tablet and the ⅜" tablet. Press through a full motion to compact the materials into one tablet. The approximate weight of each tablet is 815 mg to 890 mg containing 20 mg omeprazole. Binders such as tapioca or PVP and disintigrants such as pregelatinized starch, croscarmelose sodium or microcrystalline cellulose (MCC) and colloidal silicone dioxide (CSD) may be added. The outer layer may also comprise pharmaceutically acceptable tablet exipients. Optional coatings can also be employed, for example, light film coatings and coatings to repel ultraviolet light as is known in the art.

The outer phase can alternatively comprise a combination of sodium bicarbonate and magnesium oxide.

| Formulation 29: Lansoprazole Two Part Tablet | |
|---|---|
| Enough for 6 tablets is weighed out. | |
| Inner Core: | |
| Proton pump inhibitor: | |
| Lansoprazole powder USP | 180 mg |
| Primary Essential Buffer: | |
| Sodium bicarbonate USP | 1200 mg |
| Outer Phase: | |
| Sodium bicarbonate USP | 3960 mg |

Thoroughly blend the powders of the inner core, then weigh out approximately 230 mg of the resultant blend and add to a die of ⅜" diameter. The inner and outer tablets are then formed as described in Formulation 28. The approximate weight of each tablet is 825 mg to 900 mg. Binders such as tapioca or PVP and disintigrants such as pregelatinized starch may be added.

| Formulation 30: Pantoprazole Two Part Tablet | |
|---|---|
| Enough for 6 tablets is weighed out. | |
| Inner Core: | |
| Proton pump inhibitor: | |
| Pantoprazole powder USP | 240 mg |
| (or pantoprazole sodium) | |
| Primary Essential Buffer: | |
| Sodium bicarbonate USP | 1200 mg |
| Outer Phase: | |
| Sodium bicarbonate USP | 3960 mg |

Thoroughly blend the powders for the inner core, then weigh out approximately 220 mg of the resultant blend and add to a die of ⅜" diameter. The inner and outer tablets are then formed as described in Formulation 28. The approximate weight of each tablet is 835 mg to 910 mg. Binders such as tapioca or PVP and disintigrants such as pregelatinized starch or croscarmelose sodium may be added.

| Formulation 31: Omeprazole or esomeprazole two part tablet. Enough for 6 tablets is weighed out. | |
|---|---|
| Inner Core: Proton pump inhibitor: | |
| Omeprazole powder USP (or esomeprazole or omeprazole sodium). Primary Essential Buffer: | 120 mg |
| Sodium bicarbonate Outer Phase: | 1200 mg |
| Sodium bicarbonate | 3960 mg |

Thoroughly blend the powders of the inner core, then weigh out approximately 220 mg of the resultant blend and add to a die of ⅜" diameter. The inner and outer tablets are then formed as described in Formulation 28. The approximate weight of each tablet is 815 mg to 890 mg. Binders such as tapioca or PVP and disintigrants have been mentioned and may be added. Secondary Essential Buffers such as trisodium phosphate, tripotassium phosphate or sodium carbonate or others may be added to enhance neutralization capacity.

| Formulation 32: Lansoprazole Two part tablet Enough for 6 tablets is weighed out. | |
|---|---|
| Inner Core: Proton pump inhibitor: | |
| Lansoprazole powder USP Primary Essential Buffer: | 180 mg |
| Sodium bicarbonate Outer Phase: | 1200 mg |
| Sodium bicarbonate | 3960 mg |

Thoroughly blend the powder of the inner core, then weigh out approximately 230 mg of the resultant blend and add to a die of ⅜" diameter. The inner and outer tablets are then formed as described in Formulation 28. The approximate weight of each tablet is 825 mg to 900 mg. Binders such as tapioca or PVP and disintigrants have been mentioned and may be added. Secondary Essential Buffers such as trisodium phosphate, tripotassium phosphate or sodium carbonate or others may be added to enhance neutralization capacity.

| Formulation 33: Pantoprazole Two part tablet Enough for 6 tablets is weighed out. | |
|---|---|
| Inner Core: Proton pump inhibitor: | |
| Pantoprazole sodium powder USP Primary Essential Buffer: | 240 mg |
| Sodium bicarbonate Outer Phase: | 1200 mg |
| Sodium bicarbonate | 3960 mg |

Thoroughly blend the powders of the inner core, then weigh out approximately 220 mg of the resultant blend and add to a die of ⅜" diameter. The inner and outer tablets are then formed as described in Formulation 28. The approximate weight of each tablet is 835 mg to 910 mg. Binders such as tapioca or PVP and disintigrants may also be added. Secondary Essential Buffers, such as trisodium phosphate, tripotassium phosphate, sodium carbonate or others, may be added to enhance neutralization capacity.

| Formulation 34: Omeprazole 20 mg Two-Part Tablet | |
|---|---|
| Inner Core: Proton pump inhibitor: | |
| Omeprazole enteric coated granules (base, or sodium salt or esomeprazole sodium or magnesium) Outer Phase: | 20 mg |
| Sodium bicarbonate powder USP | 1000 mg |

The inner core is created as is known in the art such that the enteric coatings on the granules remain substantially intact. The outer phase is bound to the inner core as described in Formulation 28. Other variations of this tablet include a uniform enteric coating surrounding the proton pump inhibitor of the inner core instead of separate enteric coated granules.

| Formulation 35: Lansoprazole 30 mg Two-Part Tablet | |
|---|---|
| Inner Core: Proton pump inhibitor: | |
| Lansoprazole enteric coated granules Outer Phase: | 30 mg |
| Sodium bicarbonate powder USP | 1000 mg |

This two-part tablet is formulated as per Formulation 34.

| Formulation 36: Rabeprazole 20 mg Two-Part Tablet | |
|---|---|
| Inner Core: Proton pump inhibitor: | |
| Rabeprazole enteric coated granules Outer Phase: | 20 mg |
| Sodium bicarbonate powder USP | 1000 mg |

This two-part tablet is formulated as per Formulation 34.

| Formulation 37: Omeprazole Two Part Tablet Enough for 6 tablets is weighed out | |
|---|---|
| Inner Core: | |
| Omeprazole | 120 mg |
| Sodium bicarbonate power USP | 1200 mg |
| Outer Phase: | |
| Magnesium oxide | 1500 mg |
| Optional - calcium carbonate | 3000 mg |

The omeprazole and sodium bicarbonate of the inner core are homogeneously mixed and formed as in Formulation 28. The outer phase is combined with the inner core as in Formulation 28.

| Formulation 38: Combination Antacid and Enteric Coated Dosage Form | |
| --- | --- |
| Omeprazole enteric coated granules or enteric coated tablet | 20 mg (or an equivalent dose of another proton pump inhibitor) |
| Calcium carbonate | 1000 mg |

The above components are combined with care exerted to ensure that the enteric coating is not crushed or otherwise compromised. The resulting combination is then formed into compressed tablets or placed in capsules as is known in the pharmaceutical art. If enteric coated granules are employed, they are generally, but not required, dispersed throughout the tablet or capsule. If an enteric coated tablet is alternatively utilized, it forms a central core, which is uniformly surrounded by the calcium carbonate in either a compressed tablet or in a larger capsule. In another embodiment, a capsule containing enteric coated granules of proton pump inhibitor can be placed within a larger capsule containing the calcium carbonate.

It should be noted that other buffering agents can be utilized in lieu of or in combination with calcium carbonate. The buffer(s) employed is present in an amount of at least about 5 mEq per dose of the composition with the preferred range been 7.5 to 15 mEq. For example, sodium bicarbonate may be preferred over calcium carbonate and other antacids (such as magnesium or aluminum salts) because in many cases, sodium bicarbonate more quickly lowers gastric pH.

| Formulation 39: Combination Rapid Release and Delayed Released Proton Pump Inhibitor and Antacid | |
| --- | --- |
| Inner core: | |
| Omeprazole enteric coated granules or enteric coated tablet | 10 or 20 mg (or an equivalent dose of another proton pump inhibitor) |
| Outer phase: | |
| Omeprazole powder | 10 or 20 mg (or equivalent dose of another proton pump inhibitor) |
| Calcium Carbonate powder | 1000 mg |

The constituents of the outer phase are uniformly mixed. The inner core is created as is known in the art such that the enteric coatings on the granules or tablet remain substantially intact. The outer phase is bound to the inner core as described herein and as known in the art.

Formulation 40: Soft Chewable Proton Pump Inhibitor—Buffer Dosage Form

Omeprazole 10 or 20 mg (or an equivalent dose of another proton pump inhibitor) is combined with the ingredients of a soft chewable antacid tablet (e.g., Viactiv®), which comprises calcium carbonate 500 or 1000 mg, corn syrup, sugar, chocolate non fat milk, cocoa butter, salt, soy lecithin, glyceryl monostearate, flavoring (e.g., caramel), carrageenan, and sodium phosphate. Vitamins D3 and/or K1 can also be added. The finished chew tablets are administered to patients once to thrice daily for gastric acid related disorders.

For all formulations herein, multiple doses may be proportionally compounded as is known in the art.

The invention has been described in an illustrative manner, and it is to be understood the terminology used is intended to be in the nature of description rather than of limitation. All patents and other references cited herein are incorporated herein by reference in their entirety. Obviously, many modifications, equivalents, and variations of the present invention are possible in light of the above teachings. Therefore, it is to be understood that within the scope of the appended claims, the invention may be practiced other than as specifically described.

I claim:

1. A method of treating a gastric acid related disorder in a subject in need thereof, comprising:
   providing a solid pharmaceutical composition for oral administration to the subject, the composition consisting essentially of: (a) a therapeutically effective amount of at least one acid labile, substituted benzimidazole $H^+$, $K^+$-ATPase proton pump inhibitor; (b) at least one buffering agent in an amount of about 0.1 mEq to about 2.5 mEq per mg proton pump inhibitor; and (c) one or more optional pharmaceutically acceptable excipients; and
   orally administering the pharmaceutical composition to the subject,
   wherein upon oral administration of the pharmaceutical composition to the subject, an initial serum concentration of the proton pump inhibitor greater than about 0.1 $\mu$g/ml is obtained at any time within about 30 minutes after administration of the composition.

2. The method of claim 1, wherein the composition is administered in an amount to achieve an initial serum concentration of the proton pump inhibitor greater than about 0.15 $\mu$g/ml at any time within about 30 minutes after administration of the composition.

3. The method of claim 1, wherein the pharmaceutical composition is in a form selected from the group consisting of a tablet, capsule, powder, suspension tablet, effervescent tablet or capsule, chewable tablet, granules, pellets, and a liquid created by mixing any of the foregoing with an aqueous medium.

4. The method of claim 1, wherein the amount of the proton pump inhibitor absorbed into the serum is therapeutically effective in treating the gastric acid related disorder selected from the group consisting of duodenal ulcer disease, gastric ulcer disease, gastroesophageal reflux disease, erosive esophagitis, poorly responsive symptomatic gastroesophageal reflux disease, pathological gastrointestinal hypersecretory disease, Zollinger Ellison Syndrome, heartburn, esophageal disorder, and acid dyspepsia.

5. The method of claim 1, wherein the proton pump inhibitor is selected from the group consisting of omeprazole, lansoprazole, rabeprazole, esomeprazole, pantoprazole, pariprazole, and leminoprazole, or an enantiomer, isomer, tautomer, ester, amide, derivative, prodrug, free base, or salt thereof.

6. The method of claim 1, wherein the amount of the proton pump inhibitor is about 2 mg to about 300 mg.

7. The method of claim 1, wherein the amount of the proton pump inhibitor is about 10 mg to about 120 mg.

8. The method of claim 1, wherein the amount of the proton pump inhibitor is about 2 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, a 115 mg, or about 120 mg.

9. The method of claim 1, wherein the amount of the buffering agent is about 10 mEq to about 70 mEq.

10. The method of claim 1, wherein the amount of the buffering agent is at least 10 mEq.

11. The method of claim 1, wherein the amount of the buffering agent is about 15 mEq to about 55 mEq.

12. The method of claim 1, wherein the buffering agent comprises a combination of calcium carbonate and sodium bicarbonate.

13. The method of claim 1, wherein the buffering agent comprises a bicarbonate salt of a Group IA metal.

14. The method of claim 1, wherein the buffering agent is selected from the group consisting of a bicarbonate salt of a Group IA metal, an alkali earth metal buffering agent, a calcium buffering agent, a magnesium buffering agent, an aluminum buffering agent, sodium bicarbonate, potassium bicarbonate, magnesium hydroxide, magnesium lactate, magnesium gluconate, magnesium oxide, magnesium aluminate, magnesium carbonate, magnesium silicate, magnesium citrate, aluminum hydroxide, aluminum phosphate, aluminum hydroxide/magnesium carbonate, potassium carbonate, potassium citrate, aluminum hydroxide/sodium bicarbonate coprecipitate, aluminum glycinate, aluminum magnesium hydroxide, sodium citrate, sodium tartrate, sodium acetate, sodium carbonate, sodium polyphosphate, potassium polyphosphate, sodium pyrophosphate, sodium dihydrogen phosphate, potassium pyrophosphate, disodium hydrogenphosphate, dipotassium hydrogenphosphate, trisodium phosphate, tripotassium phosphate, potassium metaphosphate, calcium acetate, calcium glycerophosphate, calcium chloride, calcium hydroxide, calcium lactate, calcium carbonate, calcium gluconate, calcium bicarbonate, calcium citrate, calcium phosphate magnesium phosphate, potassium phosphate, sodium phosphate, trihydroxymethylaminomethane, an amino acid, an acid salt of an amino acid, an alkali salt of an amino acid, and combinations of any of the foregoing.

15. The method of claim 1, wherein the buffering agent comprises sodium bicarbonate.

16. The method of claim 15, wherein the sodium bicarbonate is in an amount from about 250 mg to about 4000 mg.

17. The method of claim 15, wherein the sodium bicarbonate is in an amount from about 1000 mg to about 2000 mg.

18. The method of claim 15, wherein the sodium bicarbonate is in an amount of at least about 400 mg.

19. The method of claim 1, wherein the buffering agent comprises calcium carbonate.

20. The method of claim 19, wherein the calcium carbonate is in an amount from about 250 mg to about 4000 mg.

21. The method of claim 19, wherein the calcium carbonate is in an amount from about 1000 mg to about 2000 mg.

22. The method of claim 19, wherein the calcium carbonate is in an amount of at least about 400 mg.

23. The method of claim 1, wherein the excipient is selected from the group consisting of a pharmaceutically compatible carrier, a binder, a suspending agent, a flavoring agent, a sweetening agent, a disintegrant, a flow aid, a lubricant, an adjuvant, a colorant, a diluent, a moistening agent, a preservative, a parietal cell activator, an antifoaming agent, an antioxidant, a chelating agent, an antifungal agent, an antibacterial agent, e* an isotonic agent, and combinations of any of the foregoing.

24. The method of claim 1, wherein the excipient is one or more flavoring agents selected from the group consisting of aspartame, thaumatin, sucrose, dextrose, or a chocolate, a cocoa, a cola, a peppermint, a spearmint, a watermelon, an apple, a caramel, a meat, a root beer, a maple, a cherry, a coffee, a mint, a licorice, a nut, a butter, a butterscotch, a butter pecan, or a peanut butter flavoring, and combinations of any of the foregoing.

25. The method of claim 1, wherein the composition is administered once or twice a day.

26. A method of treating a gastric acid related disorder in a subject in need thereof, comprising:
orally administering to the subject a single dose of a solution or suspension of a pharmaceutical composition, the composition consisting essentially of: (a) a therapeutically effective amount of at least one acid labile, substituted benzimidazole $H^+$, $K^+$-ATPase proton pump inhibitor; (b) at least one buffering agent in an amount of about 0.1 mEq to about 2.5 mEq per mg proton pump inhibitor; and (c) one or more optional pharmaceutically acceptable excipients wherein an initial serum concentration of the proton pump inhibitor greater than about 0.1 $\mu$g/ml is obtained at any time within about 30 minutes after administration of the composition, and wherein the administering step does not require further administration of the buffering agent (s) beyond that administered in the single dose.

27. The method of claim 26, wherein the composition is administered in an amount to achieve an initial serum concentration of the proton pump inhibitor greater than about 0.15 $\mu$g/ml at any time within about 30 minutes after administration of the composition.

28. The method of claim 26, wherein the subject is fasting.

29. The method of claim 26, wherein the proton pump inhibitor is selected from the group consisting of omeprazole, lansoprazole, rabeprazole, esomeprazole, pantoprazole, pariprazole, and leminoprazole, or an enantiomer, isomer, tautomer, ester, amide, derivative, prodrug, free base, or salt thereof.

30. The method of claim 26, wherein the amount of the proton pump inhibitor is about 2 mg to about 300 mg.

31. The method of claim 26, wherein the amount of the proton pump inhibitor is about 10 mg to about 120 mg.

32. The method of claim 26, wherein the amount of the proton pump inhibitor is about 2 mg, about 5 mg, about 10 mg, about 15 mg, about 20 mg, about 25 mg, about 30 mg, about 35 mg, about 40 mg, about 45 mg, about 50 mg, about 55 mg, about 60 rug, about 65 mg, about 70 mg, about 75 mg, about 80 mg, about 85 mg, about 90 mg, about 95 rug, about 100 mg, about 105 mg, about 110 mg, about 15 mg, or about 120 mg.

33. The method of claim 26, wherein the amount of the buffering agent is about 10 mEq to about 70 mEq.

34. The method of claim 26, wherein the amount of the buffering agent is at least 10 mEq.

35. The method of claim 26, wherein the amount of the buffering agent is about 15 mEq to about 55 mEq.

36. The method of claim 26, wherein the buffering agent comprises a combination of calcium carbonate and sodium bicarbonate.

37. The method of claim 26, wherein the buffering agent comprises a bicarbonate salt of a Group IA metal.

38. The method of claim 26, wherein the buffering agent is selected from the group consisting of a bicarbonate salt of a Group IA metal, an alkali earth metal buffering agent, a calcium buffering agent, a magnesium buffering agent, an aluminum buffering agent, sodium bicarbonate, potassium bicarbonate, magnesium hydroxide, magnesium lactate, magnesium gluconate, magnesium oxide, magnesium aluminate, magnesium carbonate, magnesium silicate, magnesium citrate, aluminum hydroxide, aluminum phosphate, aluminum hydroxide/magnesium carbonate, potassium carbonate, potassium citrate, aluminum hydroxide/sodium bicarbonate coprecipitate, aluminum glycinate, aluminum magnesium hydroxide, sodium citrate, sodium tartrate, sodium acetate, sodium carbonate, sodium (polyphosphate, sodium dihydrogen phosphate, potassium polyphosphate, sodium pyrophosphate, potassium pyrophosphate, disodium hydrogenphosphate, dipotassium hydrogenphosphate, trisodium phosphate, tripotassium phosphate, potassium metaphosphate, calcium acetate, calcium glycerophosphate, calcium chloride, calcium hydroxide, calcium lactate, calcium carbonate, calcium gluconate, calcium bicarbonate, calcium citrate, calcium phosphate magnesium phosphate, potassium phosphate, sodium phosphate, trihydroxymethylaminomethane, ail amino acid, an acid salt of an amino acid, an alkali salt of an amino acid, and combinations of any of the foregoing.

39. The method of claim 26, wherein the buffering agent comprises sodium bicarbonate.

40. The method of claim 39, wherein the sodium bicarbonate is in an amount from about 250 mg to about 4000 mg.

41. The method of claim 39, wherein the sodium bicarbonate is in an amount from about 1000 mg to about 2000 mg.

42. The method of claim 39, wherein the sodium bicarbonate is in an amount of at least about 400 mg.

43. The method of claim 39, wherein the buffering agent comprises calcium carbonate.

44. The method of claim 43, wherein the calcium carbonate is in an amount from about 250 mg to about 4000 mg.

45. The method of claim 43, wherein the calcium carbonate is in an amount from about 1000 mg to about 2000 mg.

46. The method of claim 43, wherein the calcium carbonate is in an amount of at least about 400 mg.

47. The method of claim 26, wherein the excipient is selected from the group consisting of a pharmaceutically compatible carrier, a binder, a suspending agent, a flavoring agent, a sweetening agent, a disintegrant, a flow aid, a lubricant, an adjuvant, a colorant, a diluent, a moistening agent, a preservative, a parietal cell activator, an antifoaming agent, an antioxidant, a chelating agent, an antifungal agent, an antibacterial agent, or an isotonic agent, and combinations of any of the foregoing.

48. The method of claim 26, wherein the subject is an adult human.

49. The method of claim 26, wherein the disorder is selected from the group consisting of duodenal ulcer disease, gastric ulcer disease, gastroesophageal reflux disease, erosive esophagitis, poorly responsive symptomatic gastroesophageal reflux disease, pathological gastrointestinal hypersecretory disease, Zollinger Ellison Syndrome, heartburn, esophageal disorder, and acid dyspepsia.

50. The method of claim 26, wherein the excipient is one or more flavoring agents selected from the group consisting of aspartame, thaumatin, sucrose, dextrose, or a chocolate, a cocoa, a cola, a peppermint, a spearmint, a watermelon, an apple, a caramel, a meat, a root beer, a maple, a cherry, a coffee, a mint, a licorice, a nut, a butter, a butterscotch, a butter pecan, or a peanut butter flavoring, and combinations of any of the foregoing.

51. The method of claim 26, wherein the composition is administered once or twice a day.

* * * * *

(12) EX PARTE REEXAMINATION CERTIFICATE (5894th)
United States Patent
Phillips

(10) Number: US 6,699,885 C1
(45) Certificate Issued: *Sep. 18, 2007

(54) SUBSTITUTED BENZIMIDAZOLE DOSAGE FORMS AND METHODS OF USING SAME

(75) Inventor: Jeffrey O. Phillips, Ashland, MO (US)

(73) Assignee: Curators of the University of Missouri, Columbia, MO (US)

Reexamination Request:
No. 90/007,686, Aug. 22, 2005

Reexamination Certificate for:
Patent No.: 6,699,885
Issued: Mar. 2, 2004
Appl. No.: 10/054,350
Filed: Jan. 19, 2002

( * ) Notice: This patent is subject to a terminal disclaimer.

Related U.S. Application Data

(63) Continuation of application No. 09/901,942, filed on Jul. 2, 2001, now Pat. No. 6,645,988, which is a continuation-in-part of application No. 09/481,207, filed on Jan. 11, 2000, now Pat. No. 6,489,346, which is a continuation-in-part of application No. 09/183,422, filed on Oct. 30, 1998, now abandoned, which is a continuation-in-part of application No. 08/680,376, filed on Jul. 15, 1996, now Pat. No. 5,840,737.

(60) Provisional application No. 60/009,608, filed on Jan. 4, 1996.

(51) Int. Cl.

| | |
|---|---|
| *A61K 47/02* | (2006.01) |
| *A61K 9/28* | (2006.01) |
| *A61K 9/20* | (2006.01) |
| *A61K 9/46* | (2006.01) |
| *A61K 9/24* | (2006.01) |
| *A61K 45/06* | (2006.01) |
| *A61K 33/00* | (2006.01) |
| *A61K 45/00* | (2006.01) |
| *A61K 9/00* | (2006.01) |
| *A61K 31/00* | (2006.01) |
| *A61K 31/4427* | (2006.01) |
| *A61K 31/4439* | (2006.01) |

(52) U.S. Cl. .................. 514/338; 514/395; 424/717
(58) Field of Classification Search ................. None
See application file for complete search history.

(56) References Cited

U.S. PATENT DOCUMENTS

| | | | | |
|---|---|---|---|---|
| 5,244,670 | A | * 9/1993 | Upson et al. | ............... 424/439 |
| 5,254,682 | A | * 10/1993 | Dhanoa et al. | ............. 540/451 |
| 5,447,918 | A | 9/1995 | McCullough | |
| 5,690,960 | A | * 11/1997 | Bengtsson et al. | .......... 424/480 |
| 5,840,737 | A | 11/1998 | Phillips | |
| 6,183,776 | B1 | 2/2001 | Depui | |
| 6,489,346 | B1 | 12/2002 | Phillips | |
| 6,699,885 | B2 | 3/2004 | Phillips | |
| 6,780,882 | B2 | 8/2004 | Phillips | |

FOREIGN PATENT DOCUMENTS

EP        0584588        8/1993

OTHER PUBLICATIONS

ZEGERID. Product Information. 2006.*
PRILOSEC. Product Information. (Date not available).*
Ansel HC. Pharmaceutical dosage forms and drug delivery systems. 1995. p. 77.*
Phillips et al. Crit. Care Med. 1996, 24(11): 1793–1800.*
CREST. Guidelines for the management of enteral tube feeding in adults. Apr. 2004.*
The Carroll Abstract M. Carroll and W. Trudeau, *Nasogastric Administration of Omeprazole for Control of Gastric pH*, Proceedings of the 10$^{th}$ World Congress Gastroenterology, Oct. 3, 1994.
M. Horowitz, et al., *The Effect of Omeprazole on Gastric Emptying in Patients with Duodenal Ulcer Disease*, 18 Br. J. Clin Pharmac. 791–794 (1984).
Martindale The Extra Pharmacopeia, Twenty–ninth edition, Edited by James E.F. Reynolds, London, The Pharmaceutical press 1989.

* cited by examiner

*Primary Examiner*—Evelyn Mei Huang

(57) ABSTRACT

Disclosed herein are methods, kits, combinations, and compositions for treating gastric acid disorders employing pharmaceutical compositions comprising a proton pump inhibiting agent (PPI) and a buffering agent in a pharmaceutically acceptable carrier.

US 6,699,885 C1

EX PARTE
REEXAMINATION CERTIFICATE
ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 26 are determined to be patentable as amended.

Claims 2–25 and 27–51, dependent on an amended claim, are determined to be patentable.

New claims 52 and 53 are added and determined to be patentable.

1. A method of treating a gastric acid related disorder in a subject in need thereof, comprising:
   providing a solid pharmaceutical composition for oral administration to the subject, the composition consisting essentially of: (a) a therapeutically effective amount of at least one acid labile, substituted benzimidazole H+, K+-ATPase proton pump inhibitor; (b) at least one buffering agent in an amount of about 0.1 mEq to about 2.5 mEq per mg of proton pump inhibitor; and (c) one or more optional pharmaceutically acceptable excipients, *wherein at least some of the proton pump inhibitor is not enteric coated and the solid pharmaceutical composition has a total buffering agent to total proton pump inhibitor weight ratio of greater than 20:1*; and
   orally administering the pharmaceutical composition to the subject,
   wherein upon oral administration of the pharmaceutical composition to the subject, an initial serum concentration of the proton pump inhibitor greater than about 0.1 µg/ml is obtained at any time within about 30 minutes after administration of the composition.

26. A method of treating a gastric acid related disorder in a subject in need thereof, comprising:
   [orally administering to the subject a single dose of a solution or suspension of a pharmaceutical composition, the composition consisting essentially of:] *providing a pharmaceutical composition consisting essentially of* (a) a therapeutically effective amount of at least one acid labile, substituted benzimidazole H+, K+-ATPase proton pump inhibitor *in powder form*; (b) at least one buffering agent *in powder form and* in an amount of about 0.1 mEq to about 2.5 mEq per mg of proton pump inhibitor; and (c) one or more optional pharmaceutically acceptable excipients, wherein at least some of the proton pump inhibitor is not enteric coated and the solid pharmaceutical composition has a total buffering agent to total proton pump inhibitor weight ratio of greater than 20:1;
   *mixing the pharmaceutical composition with a liquid to form a solution or suspension; and*
   *orally administering a single dose of the solution or suspension to the subject,* wherein an initial serum concentration of the proton pump inhibitor greater than about 0.1 µg/ml is obtained at any time within about 30 minutes after administration of the [composition,] *solution or suspension* and wherein the administration step does not require further administration of the buffering agent(s) beyond that administered in the single dose.

52. *The method of claim 1 wherein the proton pump inhibitor is selected from omeprazole, lansoprazole, rabeprazole, esomeprazole, pantoprazole or an enantiomer, isomer, free-base or salt thereof.*

53. *The method of claim 26 wherein the proton pump inhibitor is selected from omeprazole, lansoprazole, rabeprazole, esomeprazole, pantoprazole or an enantiomer, isomer, free-base or salt thereof.*

\* \* \* \* \*